US010501467B2

(12) United States Patent
Zhou et al.

(10) Patent No.: US 10,501,467 B2
(45) Date of Patent: *Dec. 10, 2019

(54) FUSED TETRA OR PENTA-CYCLIC DIHYDRODIAZEPINOCARBAZOLONES AS PARP INHIBITORS

(71) Applicant: BeiGene, Ltd., Camana Bay, Grand Cayman (KY)

(72) Inventors: Changyou Zhou, Princeton, NJ (US); Bo Ren, Beijing (CN); Hexiang Wang, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/135,512

(22) Filed: Sep. 19, 2018

(65) Prior Publication Data

US 2019/0016731 A1    Jan. 17, 2019

Related U.S. Application Data

(63) Continuation of application No. 15/479,958, filed on Apr. 5, 2017, now Pat. No. 10,112,952, which is a continuation of application No. 14/988,484, filed on Jan. 5, 2016, now Pat. No. 9,617,273, which is a continuation of application No. 14/369,374, filed as application No. PCT/CN2011/085148 on Dec. 31, 2011, now Pat. No. 9,260,440.

(51) Int. Cl.
| | | |
|---|---|---|
| A61K 31/55 | (2006.01) | |
| C07D 487/06 | (2006.01) | |
| C07D 471/16 | (2006.01) | |
| C07D 471/22 | (2006.01) | |
| C07D 487/14 | (2006.01) | |
| C07D 487/04 | (2006.01) | |
| A61K 31/551 | (2006.01) | |
| A61P 29/00 | (2006.01) | |
| A61P 35/00 | (2006.01) | |
| A61P 37/00 | (2006.01) | |

(52) U.S. Cl.
CPC .......... *C07D 487/06* (2013.01); *A61K 31/551* (2013.01); *A61P 29/00* (2018.01); *A61P 35/00* (2018.01); *A61P 37/00* (2018.01); *C07D 471/16* (2013.01); *C07D 471/22* (2013.01); *C07D 487/04* (2013.01); *C07D 487/14* (2013.01)

(58) Field of Classification Search
CPC .................................................... A61K 31/55
See application file for complete search history.

(56) References Cited

U.S. PATENT DOCUMENTS

| 9,260,440 | B2 | 2/2016 | Zhou et al. |
| 9,617,273 | B2 | 4/2017 | Zhou et al. |
| 10,112,952 | B2 | 10/2018 | Zhou et al. |
| 2015/0175617 | A1 | 6/2015 | Zhou et al. |
| 2016/0159811 | A1 | 6/2016 | Zhou et al. |
| 2016/0222012 | A1 | 8/2016 | Ruan |
| 2017/0305921 | A1 | 10/2017 | Zhou et al. |
| 2019/0177325 | A1 | 6/2019 | Wang et al. |

FOREIGN PATENT DOCUMENTS

| JP | 2002-534523 | 10/2002 |
| WO | WO 2000/042040 | 7/2000 |
| WO | WO 2002/044183 | 6/2002 |
| WO | WO 2004/063198 | 7/2004 |
| WO | WO 2010/017055 | 2/2010 |
| WO | WO 2013/097225 | 7/2013 |
| WO | WO 2015/035606 | 3/2015 |
| WO | WO 2016/000619 | 1/2016 |
| WO | WO 2017/032289 | 3/2017 |
| WO | WO 2018/059437 | 4/2018 |
| WO | WO 2018/157794 | 9/2018 |
| WO | WO 2019/015561 | 1/2019 |

OTHER PUBLICATIONS

Supplementary European Search Report for European Application No. 11878508.8, dated Sep. 22, 2015, 3 pages.
International Preliminary Report on Patentability for International Application No. PCT/CN2011/085148, dated Jul. 1, 2014, 7 pages.
International Search Report and Written Opinion for International Application No. PCT/CN2011/085148, dated Sep. 27, 2012, 12 pages.
International Search Report and Written Opinion for International Application No. PCT/CN2016/096200, dated Nov. 11, 2016, 12 pages.
International Search Report and Written Opinion for International Application No. PCT/CN2017/103660, dated Jan. 9, 2018, 11 pages.
International Search Report and Written Opinion for International Application No. PCT/CN2018/077433, dated Jun. 5, 2018, 11 pages.
International Search Report and Written Opinion for International Application No. PCT/CN2018/095911, dated Oct. 26, 2018, 9 pages.
Chen, A., "PARP inhibitors: its role in treatment of cancer," Chinese Journal of Cancer, 2011, vol. 30, Issue 7, pp. 463-471.
Underhill, C. et al., "A review of PARP inhibitors: from bench to bedside," Annals of Oncology, Advance Access published Jul. 19, 2010, doi:10.1093/annonc/mdq322, Retrieved from the Internet: <URL: http://annonc.oxfordjournals.org/>. Retrieved from the Internet on Jun. 14, 2016, 12 pages.
STN International, RN: 1858211-28-5, STN Registry, Feb. 2, 2016, 2 pages.
Extended European Search Report for European Application No. 16838548.2, dated Dec. 19, 2018, 8 pages.
Morissette, S. L., "High-throughput crystallization: polymorphs, salts, co-crystals and solvates of pharmaceutical solids," Advanced Drug Delivery Reviews, vol. 56, No. 3, Feb. 2004, pp. 275-300.

(Continued)

*Primary Examiner* — Bruck Kifle
(74) *Attorney, Agent, or Firm* — Cooley LLP

(57) ABSTRACT

Provided are certain fused tetra or penta-cyclic compounds and salts thereof, compositions thereof, and methods of use thereof.

17 Claims, No Drawings

(56) References Cited

OTHER PUBLICATIONS

Fujiwara, M. et al., "First-principles and direct design approaches for the control of pharmaceutical crystallization," Journal of Process Control, vol. 15, No. 5, Aug. 2005, pp. 493-504.
Variankaval, N. et al., "From form to function: Crystallization of active pharmaceutical ingredients," AlChE Journal, vol. 54, No. 7, Jul. 2008, pp. 1682-1688.
Caira, M. R., "Crystalline polymorphism of organic compounds," Topics in Current Chemistry, vol. 198, 1998, pp. 163-208.

FUSED TETRA OR PENTA-CYCLIC DIHYDRODIAZEPINOCARBAZOLONES AS PARP INHIBITORS

CROSS-REFERENCE TO RELATED APPLICATION

This application is a continuation of U.S. application Ser. No. 15/479,958 filed on Apr. 5, 2017 with the title "FUSED TETRA OR PENTA-CYCLIC DIHYDRODIAZEPINOCARBAZOLONES AS PARP INHIBITORS," which is a continuation of U.S. patent application Ser. No. 14/988,484 filed on Jan. 5, 2016 with the title "FUSED TETRA OR PENTA-CYCLIC DIHYDRODIAZEPINOCARBAZOLONES AS PARP INHIBITORS," now issued as U.S. Pat. No. 9,617,273 on Apr. 11, 2017, which is a continuation of U.S. patent application Ser. No. 14/369,374 filed on Mar. 6, 2015 with the title "FUSED TETRA OR PENTA-CYCLIC DIHYDRODIAZEPINOCARBAZOLONES AS PARP INHIBITORS," now issued as U.S. Pat. No. 9,260,440 on Feb. 16, 2016, which is a U.S. national stage application of International Application No. PCT/CN2011/085148, which was filed on Dec. 31, 2011 with the title "FUSED TETRA OR PENTA-CYCLIC DIHYDRODIAZEPINOCARBAZOLONES AS PARP INHIBITORS," the content of each of which are hereby incorporated by reference in its entirety for all purposes.

Disclosed herein are fused tetra or penta-cyclic compounds which can inhibit the activity of poly (ADP-ribose) polymerases (PARPs), pharmaceutical compositions comprising at least one of the compounds, and the use thereof in treating certain diseases.

Poly(ADP-ribose) polymerases (PARPs), previously known as poly(ADP-ribose) synthases or poly(ADP-ribose) transferases, are a family of proteins that contain PARP catalytic domain (BMC Genomics, 2005 Oct. 4; 6: 139.). Approximately 17 members of PARPs have been discovered so far, including PARP-1, PARP-2, PARP-3, PARP-4(Vault-PARP), PARP-5a (Tankyrase-1), PARP5b (Tankyrase-2), PARP-6, PARP-7 (tiPARP),PARP-8, PARP-9 (BAL), PARP-10, PARP-11, PARP-12, PARP-13 (ZAP), PARP-14 (CoaSt6), PARP-15, and PARP-16. The catalytic activity of PARPs can be to transfer the ADP-ribose moiety from nicotinamide adenine dinucleotide (NAD$^+$) to glutamic acid residues of a number of target proteins, and to form long branches of ADP-ribose polymers. However, some of the PARP families have been reported to catalyze only mono-ADP-ribosylation of targets while activities of others have yet to be reported (*Mol. Cell.* 2008 Oct. 10; 32(1): 57-69.). A number of the PARP enzymes have been reported to show important functional roles in, for example, DNA repair, transcriptional regulation, mitotic progression, genomic integrity, telomere stability, cell death, and Wnt signaling pathway.

PARP-1 may be the most abundant and most well studied member of the family, and PARP-2 may be its closest relative. PARP can be activated by damaged DNA fragments and, once activated, catalyzes the attachment of poly-ADP-ribose units to a variety of nuclear proteins, including histones and PARP itself. The resultant foci of poly(ADP-ribose) has been reported to halt transcription and recruit repair enzymes to the site of DNA damage. The pivotal role of PARP in the repair of DNA strand breaks has been reported as well established. PARP-1 knockout cells can show increased sensitivity to, for example, alkylating agents, topoisomerase (topo) I inhibitors and γ-irradiation. PARP inhibitors have been reported to sensitize tumor cells to radiation treatment (including ionizing radiation and other DNA damaging treatments) and anticancer drugs (including platinum drugs, temozolomide, and topoisomerase I inhibitors). PARP inhibitors have also been reported to be effective in radiosensitizing (hypoxic) tumor cells and in preventing tumor cells from recovering from potentially lethal and sublethal damages of DNA after radiation therapy, presumably by their ability to prevent broken DNA strand from rejoining and by affecting several DNA damage signaling pathways.

PARP inhibitors have been suggested to effectively destroy tumors defective in the BRCA1 or BRCA2 genes through the concept of synthetic lethality. While tumors with wild type BRCA genes can be insensitive to PARP inhibitors, the presence of BRCA1 or BRCA2 deficiency leads to significantly increased sensitivity of those genes to PARP inhibitors. It can be suggested that PARP inhibitors may cause an increase in DNA single-strand breaks (SSBs), which are converted during replication to toxic DNA double-strand breaks (DSBs) that cannot be repaired by homology recombination repair in BRCA1/2 defective cells. The synthetic lethality may have also been reported for PARP inhibitors, and ATM, ATR, RAD51 deficiency, and other homology recombination repair defects. PARP inhibitors can be useful for treatment of cancers with DNA repair deficiencies.

Activation of PARP may also have a role in mediating cell death. Excessive activation of PARP may have been indicated in ischemia-reperfusion injuries, and in neurological injuries that can occur during stroke, trauma and Parkinson's disease. The overactivation of PARP may lead to rapid consumption of NAD$^+$ to form ADP-ribose polymers. Because the biosynthesis of NAD$^+$ can be an ATP consuming process, the cellular level of ATP could be subsequently depleted and the ischemic cells could die from necrosis. Inhibition of PARP can be expected to reduce cell death by preserving cellular NAD$^+$ and ATP level and by preventing the activation of certain inflammation pathways that could have contributed to further cellular damage via an immune response.

It has been reported that PARP activation can play a key role in both NMDA- and NO-induced neurotoxicity. The reports were based on cortical cultures and hippocampal slices wherein prevention of toxicity can be directly correlated with PARP inhibition potency. The potential role of PARP inhibitors in treating neurodegenerative diseases and head trauma has been hypothesized.

Studies have reported that PARP inhibitors can be used for treatment and prevention of autoimmune disease such as Type I diabetes and diabetic complications (*Pharmaceutical Research* (2005)52: 60-71).

PARP-3 appears to be a newly characterized member of the PARP family. A recent study has reported the role of PARP-3 in genome integrity and mitotic progression (*PNAS* |Feb. 15, 2011|vol. 108|no. 7|2783-2788). PARP-3 deficiency can lead to reduced cellular response to DNA double-strand breaks. PARP-3 deficiency when combined with PARP-1/2 inhibitors can result in lowered cell survival in response to x-irradiation. PARP-3 can be required for mitotic spindle integrity during mitosis and telomere stability. Therefore inhibition of PARP-3 can also potentially lead to antitumor activity.

Tankyrase-1 (TRF 1-interacting ankyrin-related ADP-ribosepolymerase 1) is initially identified as a component of the human telomeric complex. Tankyrase-2 may share overall sequence identity of 83% and sequence similarity of 90% with Tankyrase-1. Mouse genetic studies reportedly suggest substantial functional overlaps between tankyrase-1 and tankyrase-2. Tankyrase-1 has reportedly been shown to be a positive regulator of telomere length, allowing elongation of the telomeres by telomerase. Inhibition of tankyrases can sensitize cells to telomerase inhibitors. Tankyrase-1 can be also required for sister telomere dissociation during mitosis. Inhibition of Tankyrase-1 by RNAi can induce mitotic arrest. Inhibition of tankyrases potentially may lead to antitumor activity.

Tankyrases have reportedly been implicated in the regulation of Wnt pathway. Wnt pathway can be negatively regulated by proteolysis of the downstream effector β-catenin by the β-catenin destruction complex, comprising adenomatous polyposis coli (APC), axin and glycogen synthase kinase 3α/β (GSK3α/β). Inappropriate activation of the Wnt pathway has been reported in many cancers. Notably, truncating mutations of the tumor suppressor APC can be the most prevalent genetic alterations in colorectal carcinomas. APC mutation may lead to defective β-catenin destruction complex, accumulation of nuclear β-catenin, and/or active transcription of Wnt pathway-responsive genes. Tankyrase inhibitors have been reported to stabilize the β-catenin destruction complex by increasing axin levels. Axin, a key component of β-catenin destruction complex, can be degraded through PARylation and ubiquitination. Inhibition of tankyrases can lead to reduced degradation of axin and/or increased level of axin. Tankyrase inhibitors have been reported to inhibit colony formation by APC-deficient colon cancer cells. Therefore, tankyrase inhibitors can be potentially useful for treatment of cancers with activated Wnt pathways.

Provided herein are compounds and/or pharmaceutically acceptable salts thereof, pharmaceutical compositions comprising at least one of those compounds and pharmaceutically acceptable salts thereof, and use thereof in inhibiting PARP activity for treating diseases, such as cancer. For example, the compounds and compositions as described herein can be useful in treating cancers with defective DNA repair pathways, and/or can be useful in enhancing the effectiveness of chemotherapy and radiotherapy.

Certain small molecules have been reported to be PARP inhibitors. For example, PCT Publication Nos. WO 2000/42040 and 2004/800713 report tricyclic indole derivatives as PARP inhibitors. PCT Publication Nos. WO 2002/44183 and 2004/105700 report tricyclic diazepinoindole derivatives as PARP inhibitors; PCT Publication No. WO 2011/130661 and GB patent 2462361 report dihydropyridophthalazinone derivatives as PARP inhibitors; other cyclic compounds reported as PARP inhibitors can be found in the following patents: U.S. Pat. Nos. 7,915,280; 7,235,557; USRE041150; U.S. Pat. No. 6,887,996; and EP1339402B1.

PCT Publication No. WO 2004/4014294, published on Feb. 19, 2004 reports 4,7-disubstituted indole derivatives as PARP inhibitors. Other cyclic compounds as PARP inhibitors are also reported in U.S. Pat. No. 6,906,096. PCT Publication No. WO 2009/063244, published on May 22, 2009, discloses pyridazinone derivatives as PARP inhibitors. GB Patent No. 2462361, published on Oct. 2, 2010 discloses dihydropyridophthalazinone derivatives as PARP inhibitors. U.S. Pat. No. 7,429,578, published on Sep. 30, 2008, reports tricyclic derivatives as PARP inhibitors. Other cyclic compounds as PARP inhibitors are also reported in the following patents: EPI 140936B1; U.S. Pat. Nos. 6,495,541; 6,799,298. U.S. Pat. No. 6,423,705, published on Jul. 23, 2003, reports a combination therapy using PARP inhibitors. Other combination therapies using PARP inhibitors are also reported in the following patent publications: US 2009/0312280A1; WO 2007113647A1. U.S. Pat. No. 6,967,198, published on Nov. 22, 2005, reports tricyclic compounds as protein kinase inhibitors for enhancing efficacy of antineoplastic agents and radiation therapy. U.S. Pat. No. 7,462,713, published on Dec. 9, 2008, also reports tricyclic compounds as protein kinase inhibitors for enhancing efficacy of antineoplastic agents and radiation therapy. EP patent No. 1585749, published on Aug. 13, 2008, reports diazepinoindole derivatives as antineoplastic agents and radiation therapy.

Disclosed herein are compounds that can be poly(ADP-ribosyl)transferase (PARPs) inhibitors, and can be useful, for example, in treating cancers, stoke, head trauma, and neurodegenerative diseases. As cancer therapeutics, the compounds/pharmaceutically acceptable salts as described herein may be used in combination with DNA-damaging cytotoxic agents, for example, cisplatin, topotecan, irinotecan, or temozolomide, and/or radiation.

Provided is at least one compound selected from compounds of Formula (I):

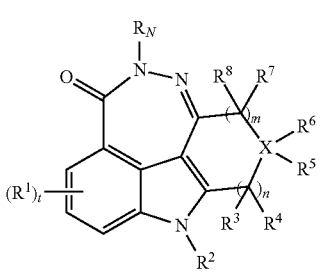

stereoisomers thereof, and pharmaceutically acceptable salts thereof, wherein:

$R_N$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, or heteroaryl is independently optionally substituted with at least one substituent $R^{12}$;

X is selected from the group consisting of C, N, O, and S;

m and n, which may be the same or different, are each an integer of f 0, 1, 2, or 3;

t is an integer of 0, 1, 2, or 3;

$R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^3$, $R^4$, $R^5$, $R^6$, $R^7$ and $R^8$, which may be the same or different, are each independently selected from hydrogen, halogen, —$NR^9R^{10}$, —$OR^9$, oxo, —$COR^9$, —$CO_2R^9$, —$CONR^9R^{10}$, —$NR^9CONR^{10}R^{11}$, —$NR^9CO_2R^{10}$, —$NR^9SO_2R^{10}$, —$SO_2R^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) they are attached, form a 3- to 8-membered saturated, partially or fully unsaturated ring having 0, 1 or 2 heteroatoms independently selected from —$NR^{13}$—, —O—, —S—, —SO— or —$SO_2$-, and said ring is optionally substituted with at least one substituent $R^{12}$, provided that when X is O, $R^5$ and $R^6$ are absent, when X is N, $R^6$ is absent, when X is S, $R^5$ and $R^6$ are absent, or at least one of $R^5$ and $R^6$ is oxo, when one of $R^3$ and $R^4$ is oxo, the other is absent, when one of $R^7$ and $R^8$ is oxo, the other is absent, and when X is C and one of $R^5$ and $R^6$ is oxo, the other is absent;

$R^9$, $R^{10}$, and $R^{11}$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, or heteroaryl is independently optionally substituted with at least one substituent $R^{12}$;

$R^{12}$ is selected from CN, halogen, haloalkyl, $NO_2$, —NR'R", —OR', oxo, —COR', —$CO_2R'$, —CONR'R", —NR'CONR"R'", —$NR'CO_2R"$, —$NR'SO_2R"$, —$SO_2R'$, alkyl, alkenyl, alkynyl, cycloalkyl, heterocyclyl, aryl, and heteroaryl, wherein R', R", and R'" are independently selected from hydrogen, haloalkyl, alkyl, arylalkyl, alkenyl, alkynyl, cycloalkyl, heterocyclyl, aryl, and heteroaryl, or (R' and R"), and/or (R" and R'") together with the atoms to which they are attached, form a 3- to 8-membered saturated, partially or fully unsaturated ring having 0, 1 or 2 additional heteroatoms independently selected from —$NR^{13}$—, —O—, —S—, —SO— and —$SO_2$-.

$R^{13}$ is selected from hydrogen, alkyl, cycloalkyl, aryl, heteroaryl, and heterocyclyl.

Also provided is a pharmaceutical composition comprising at least one pharmaceutically acceptable carrier and at least one compound selected from compounds of Formula (I) and pharmaceutically acceptable salts thereof as described herein.

Also provided is a method of inhibiting PARP comprising contacting the PARP with an amount of at least one compound selected from compounds of Formula (I) and pharmaceutically acceptable salts thereof as described herein effective to inhibit the PARP.

Also provided is a method of treating at least one disease responsive to inhibition of PARP comprising administering to a subject in recognized need of such treating for the at least one disease an amount of at least one compound selected from compounds of Formula (I) and pharmaceutically acceptable salts thereof as described herein effective to treat the at least one disease, wherein the at least one disease is selected from, for example, cancer (such as leukemia, colon cancer, glioblastomas, lymphomas, melanomas, carcinomas of the breast, and cervical carcinomas),cytotoxic cancer, ischemia reperfusion injury (such as those associated with, but not limited to, heart failure, myocardial infarction, stroke, other neural trauma, and organ transplantation), reperfusion (such as the reperfusion of the eye, kidney, gut and skeletal muscle), inflammatory diseases (such as arthritis, gout, inflammatory bowel disease, CNS inflammation, multiple sclerosis, allergic encephalitis, sepsis, septic shock, hemmorhagic shock, pulmonary fibrosis, and uveitis), immunological diseases or disorders (such as rheumatoid arthritis and septic shock), degenerative disease (such as diabetes and Parkinsons disease), hypoglycemia, retroviral infection, liver toxicity following acetominophen overdose, cardiac and kidney toxicities from doxorubicin and platinum based antineoplastic agents, skin damage secondary to sulfur mustards.

Also provided is a use of at least one compound selected from compounds of Formula (I) and pharmaceutically acceptable salts thereof as described herein in manufacture of a medicament for inhibiting PARP.

Also provided is a use of at least one compound selected from compounds of Formula (I) and pharmaceutically acceptable salts thereof as described herein in the manufacture of a medicament for treating at least one disease selected from, for example, cancer (such as leukemia, colon cancer, glioblastomas, lymphomas, melanomas, carcinomas of the breast, and cervical carcinomas), cytotoxic cancer, ischemia reperfusion injury (such as those associated with, but not limited to, heart failure, myocardial infarction, stroke, other neural trauma, and organ transplantation), reperfusion (such as the reperfusion of the eye, kidney, gut and skeletal muscle), inflammatory diseases (such as arthritis, gout, inflammatory bowel disease, CNS inflammation, multiple sclerosis, allergic encephalitis, sepsis, septic shock, hemmorhagic shock, pulmonary fibrosis, and uveitis), immunological diseases or disorders (such as rheumatoid arthritis and septic shock), degenerative disease (such as diabetes and Parkinsons disease), hypoglycemia, retroviral infection, liver toxicity following acetominophen overdose, cardiac and kidney toxicities from doxorubicin and platinum based antineoplastic agents, skin damage secondary to sulfur mustards.

As used herein, the following words, phrases and symbols are generally intended to have the meanings as set forth below, except to the extent that the context in which they are used indicates otherwise. The following abbreviations and terms have the indicated meanings throughout: The term "alkyl" herein refers to a hydrocarbon group selected from linear and branched saturated hydrocarbon groups comprising from 1 to 18, such as from 1 to 12, further such as from 1 to 6, carbon atoms. Examples of the alkyl group can be selected from methyl, ethyl,1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group can be selected from 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$) and 3,3-dimethyl-2-butyl (—$CH(CH_3)C(CH_3)_3$ groups.

The term "alkenyl" herein refers to a hydrocarbon group selected from linear and branched hydrocarbon groups comprising at least one C═C double bond and from 2 to 18, such as from 2 to 6, carbon atoms. Examples of the alkenyl group may be selected from ethenyl or vinyl (—CH═$CH_2$), prop-1-enyl (—CH═$CHCH_3$), prop-2-enyl (—$CH_2CH$═$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as from 2 to 6, carbon atoms. Examples of the alkynyl group include ethynyl (—C≡CH), 1-propynyl (—C≡CCH$_3$), 2-propynyl (propargyl, —CH$_2$C≡CH), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as 3 to 8, further such as 3 to 6, 3 to 5, or 3 to 4 carbon atoms. Even further for example, the cycloalkyl group may be selected from monocyclic group comprising from 3 to 12, such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "Aryl" herein refers to a group selected from: 5- and 6-membered carbocyclic aromatic rings, for example, phenyl;
bicyclic ring systems such as 7 to 12 membered bicyclic ring systems wherein at least one ring is carbocyclic and aromatic, selected, for example, from naphthalene, indane, and 1,2,3,4-tetrahydroquinoline; and
tricyclic ring systems such as 10 to 15 membered tricyclic ring systems wherein at least one ring is carbocyclic and aromatic, for example, fluorene.

For example, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "arylalkyl" herein refers to an alkyl group as defined above substituted by an aryl group as defined above.

The term "halogen" or "halo" herein refers to F, Cl, Br or I.

The term "heteroaryl" herein refers to a group selected from:
5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;
8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

Compounds described herein may contain an asymmetric center and may thus exist as enantiomers. Where the compounds described herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." *J. Chromatogr.*, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)_n$—COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "pharmaceutically acceptable salts thereof" include salts of at least one compound of Formulas I, II (including II-1, II-2 or II-3) or III, and salts of the stereoisomers of at least one compound of Formulas I, II (including II-1, II-2 or 11-3) or III, such as salts of enantiomers, and/or salts of diastereomers.

"Treating", "treat", or "treatment" or "alleviation" refers to administering at least one compound and/or at least one pharmaceutically acceptable salt thereof disclosed herein to a subject in recognized need thereof that has, for example, cancer and/or inflammatory disease, or has a symptom of, for example, cancer and/or inflammatory disease, or has a predisposition toward, for example, cancer and/or inflammatory disease, with the purpose to cure, heal, alleviate, relieve, alter, remedy, ameliorate, improve, or affect, for example, cancer and/or inflammatory disease, the symptoms of, for example, cancer and/or inflammatory disease, or the predisposition toward, for example, cancer and/or inflammatory disease.

The term "effective amount" refers to an amount of at least one compound, stereoisomers thereof, and pharmaceutically acceptable salts thereof disclosed herein effective to "treat," as defined above, a disease or disorder in a subject. In the case of cancer, the effective amount may cause any of the changes observable or measurable in a subject as described in the definition of "treating," "treat," "treatment" and "alleviation" above. For example, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of PARP. For cancer therapy, efficacy in vivo can, for example, be measured by assessing the duration of survival, time to disease progression (TTP), the response rates (RR), duration of response, and/or quality of life. Effective amounts may vary, as recognized by those skilled in the art, depending on route of administration, excipient usage, and co-usage with other agents.

The term "inhibition" indicates a decrease in the baseline activity of a biological activity or process. "Inhibition of PARP" refers to a decrease in the activity of PARP as a direct or indirect response to the presence of at least one compound and/or at least one pharmaceutically acceptable salt disclosed herein, relative to the activity of PARP in the absence of the at least one compound and/or the at least one pharmaceutically acceptable salt thereof. The decrease in activity is not bound by theory and may be due to the direct interaction of the at least one compound, stereoisomers thereof, and pharmaceutically acceptable salts thereof disclosed herein with PARP, or due to the interaction of the at least one compound and/or at least one pharmaceutically acceptable salt disclosed herein, with one or more other factors that in turn affect PARP activity. For example, the presence of at least one compound, stereoisomers thereof, and pharmaceutically acceptable salts thereof disclosed herein, may decrease PARP activity by directly binding to the PARP, by causing (directly or indirectly) another factor to decrease PARP activity, or by (directly or indirectly) decreasing the amount of PARP present in the cell or organism.

The term "at least one substituent" disclosed herein includes, for example, from 1 to 4, such as from 1 to 3, further as 1 or 2, substituents. For example, "at least one substituent $R^{12}$" disclosed herein includes from 1 to 4, such as from 1 to 3, further as 1 or 2, substituents selected from the list of $R^{12}$ as described herein.

In the first aspect, provided is at least one compound selected from compounds of Formula

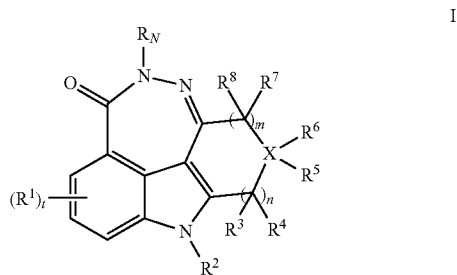

I stereoisomers thereof, and pharmaceutically acceptable salts thereof,
wherein:
$R_N$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

X is selected from the group consisting of C, N, O, and S;
m and n, which may be the same or different, are each an integer of f 0, 1, 2, or 3;
t is an integer of 0, 1, 2, or 3;
$R^1$, at each occurrence, is independently selected from halogen, CN, NO$_2$, OR$^9$, NR$^9$R$^{10}$, NR$^9$COR$^{10}$, NR$^9$SO$_2$R$^{10}$, CONR$^9$R$^{10}$, COOR$^9$, SO$_2$R$^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^2$ is selected from the group consisting of hydrogen, COR$^9$, CONR$^9$R$^{10}$, CO$_2$R$^9$, SO$_2$R$^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^3$, $R^4$, $R^5$, $R^6$, $R^7$ and $R^8$, which may be the same or different, are each independently selected from absence, hydrogen, halogen, —NR$^9$R$^{10}$, —OR$^9$, oxo, —COR$^9$, —CO$_2$R$^9$, —CONR$^9$R$^{10}$, —NR$^9$CONR$^{10}$R$^{11}$, —NR$^9$CO$_2$R$^{10}$, —NR$^9$SO$_2$R$^{10}$, —SO$_2$R$^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) they are attached, form a 3- to 8-membered saturated, partially or fully unsaturated ring having 0, 1 or 2 heteroatoms independently selected from —NR$^3$—, —O—, —S—, —SO— or —SO$_2$-, and said ring is optionally substituted with at least one substituent R$^{12}$, provided that
when X is O, R$^5$ and R$^6$ are absent,
when X is N, R$^6$ is absent,
when X is S, R$^5$ and R$^6$ are absent, or at least one of R$^5$ and R$^6$ is OXO,
when one of R$^3$ and R$^4$ is oxo, the other is absent,
when one of R$^7$ and R$^8$ is oxo, the other is absent, and
when X is C and one of R$^5$ and R$^6$ is Oxo, the other is absent;

R$^9$, R$^{10}$, and R$^{11}$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, or heteroaryl is independently optionally substituted with at least one substituent R$^{12}$;

R$^{12}$ is selected from CN, halogen, haloalkyl, NO$_2$, —NR'R", —OR', oxo, —COR', —CO$_2$R', —CONR'R", —NR'CONR"R'", —NR'CO$_2$R", —NR'SO$_2$R", —SO$_2$R', alkyl, alkenyl, alkynyl, cycloalkyl, heterocyclyl, aryl, and heteroaryl, wherein R', R", and R'" are independently selected from hydrogen, haloalkyl, alkyl, arylalkyl, alkenyl, alkynyl, cycloalkyl, heterocyclyl, aryl, and heteroaryl, or (R' and R"), and/or (R" and R'") together with the atoms to which they are attached, form a 3- to 8-membered saturated, partially or fully unsaturated ring having 0, 1 or 2 additional heteroatoms independently selected from —NR$^{13}$—, —O—, —S—, —SO— and —SO$_2$-.

R$^{13}$ is selected from hydrogen, alkyl, cycloalkyl, aryl, heteroaryl, and heterocyclyl.

In some embodiments, X in Formula (I) is C. In some embodiments, X in Formula (I) is N.

In some embodiments, m and n in Formula (I) are both an integer of 1. In some embodiments, n in Formula (I) is 1 and m in Formula (I) is 2; in other embodiments, n in Formula (I) is 2 and m in Formula (I) is 1.

In some embodiments, t in Formula (I) is 0. In some embodiments, t in Formula (I) is 1 and R$^1$ in Formula (I) is selected from halogen, CN, NO$_2$, OR$^9$, NR$^9$R$^{10}$, NR$^9$COR$^{10}$, NR$^9$SO$_2$R$^{10}$, CONR$^9$R$^{10}$, COOR$^9$, SO$_2$R$^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, or heteroaryl is independently optionally substituted with at least one substituent R$^{12}$ as defined above. In some further embodiments, t in Formula (I) is 1, and R$^1$ in Formula (I) is halogen (such as F, Cl and Br, further such as F) or alkyl (such as C$_{1-12}$alkyl, further such as C$_{1-6}$alkyl). In some further embodiments, t in Formula (I) is 1 and R$^1$ in Formula (I) is halogen (such as F).

In some embodiments, RN in Formula (I) is an alkyl group optionally substituted with hydroxy or alkoxyl. In some further embodiments, R$_N$ in Formula (I) is a C$_{1-12}$alkyl group optionally substituted with hydroxy or with C$_{1-12}$alkoxyl. In some further embodiments, RN in Formula (I) is a C$_{1-6}$alkyl group optionally substituted with hydroxy or with C$_{1-6}$alkoxyl.

In some embodiments, R$^2$ in Formula (I) is hydrogen or alkyl (such as C$_{1-12}$alkyl, further such as C$_{1-6}$alkyl) optionally substituted with at least one substituent R$^{12}$ as defined for Formula (I). In some embodiments, R$^2$ in Formula (I) is alkyl (such as C$_{1-12}$alkyl, further such as C$_{1-6}$alkyl) optionally substituted with at least one substituent R$^{12}$, wherein R$^{12}$ is selected from —NR'R", —OR', heterocyclyl, and aryl, wherein R', and R" are independently selected from hydrogen, haloalkyl, alkyl, and arylalkyl, or R' and R" together with the atom to which they are attached, form a 3- to 8-membered saturated, partially or fully unsaturated ring having 0, 1 or 2 additional heteroatoms independently selected from —NR$^{13}$—, —O—, —S—, —SO— and —SO$_2$-. In some further embodiments, R$^2$ in Formula (I) is an alkyl group (such as C$_{1-12}$alkyl, further such as C$_{1-6}$alkyl) optionally substituted with at least one substituent R$^{12}$, wherein R$^{12}$ is selected from —NR'R", —OR', heterocyclyl, and aryl (such as phenyl), wherein R' and R" are independently selected from hydrogen, haloalkyl (such as halo C$_{1-12}$alkyl, further such as haloC$_{1-6}$alkyl), alkyl (such as C$_{1-12}$alkyl, further such as C$_{1-6}$alkyl), and arylalkyl (such as phenylC$_{1-12}$alkyl, further such as phenylC$_{1-6}$alkyl)), or R' and R" together with the atom to which they are attached, form a 3- to 8-membered saturated, partially or fully unsaturated ring having 0, 1 or 2 additional heteroatoms independently selected from —NR$^{13}$—, —O—, —S—, —SO— and —SO$_2$— (such as a 5- or 6-membered saturated ring having 0 or 1 additional heteroatom which is O, further such as 5-membered saturated ring, 6-membered saturated ring, or 6-membered saturated ring having one oxygen heteroatom). In some further embodiments, R$^2$ in Formula (I) is alkyl (such as C$_{1-12}$alkyl, further such as C$_{1-6}$alkyl) optionally substituted with at least one substituent selected from an aryl group (such as phenyl), 3-, 4-, 5-, 6-, 7-, and 8-membered heterocyclyl group containing one nitrogen heteroatom and/or one oxygen heteroatom, —OR', and —NR'R", wherein R' and R" are independently selected from hydrogen, haloalkyl (such as haloC$_{1-12}$alkyl, further such as haloC$_{1-6}$alkyl), alkyl (such as C$_{1-12}$alkyl, further such as C$_{1-6}$alkyl), and arylalkyl (such as phenylC$_{1-6}$alkyl). In some further embodiments, R$^2$ in Formula (I) is alkyl (such as C$_{1-12}$alkyl, further such as C$_{1-6}$alkyl) optionally substituted with at least one substituent selected from an aryl group (such as phenyl); 3-, 4-, 5-, 6-, 7-, and 8-membered heterocyclyl group containing one nitrogen heteroatom and/or one oxygen heteroatom selected from pyrrolidinyl, piperidinyl, morpholino, and oxiranyl; —OR'; and —NR'R", wherein R' and R" are independently selected from the hydrogen, haloalkyl (such as haloC$_{1-6}$alkyl), alkyl (such as C$_{1-12}$alkyl, further such as C$_{1-6}$alkyl), and arylalkyl (such as phenylC$_{1-6}$alkyl, further such as phenylmethyl).

In some embodiments, R$^5$ in Formula (I) is selected from hydrogen, alkyl, cycloalkyl, aryl, —COR$^9$, and —COOR$^9$, wherein each of the alkyl, cycloalkyl, and aryl is independently optionally substituted with at least one substituent R$^{12}$, and R$^9$ is alkyl or cycloalkyl optionally substituted with at least one substituent R$^{12}$, and R$^{12}$ is defined as for Formula (I). In some embodiments, R$^5$ in Formula (I) is selected from hydrogen, alkyl, cycloalkyl, aryl, —COR$^9$, and —COOR$^9$, wherein each of the alkyl, cycloalkyl, or aryl is independently optionally substituted with at least one substituent R$^{12}$, and R$^9$ is alkyl or cycloalkyl optionally substituted with at least one substituent R$^{12}$, and R$^{12}$ is selected from NR'R", aryl, and NR'CO$_2$R", wherein R' and R" are independently selected from hydrogen, haoloalkyl and alkyl. In some further embodiments, R$^5$ in Formula (I) is selected from hydrogen; alkyl (such as C$_{1-12}$alkyl, further such as C$_{1-6}$alkyl) optionally substituted with at least one substituent selected from NR'R" and aryl (such as phenyl); cycloalkyl (such as C$_3$, C$_4$, C$_5$, C$_6$, C$_7$, C$_8$cycloalkyl); aryl (such as phenyl) optionally substituted with NR'R"; and —COR$^9$, wherein R$^9$ is cycloalkyl (such as C$_3$, C$_4$, C$_5$, C$_6$, C$_7$, C$_8$cycloalkyl), or alkyl (such as C$_{1-12}$alkyl, further such as C$_{1-6}$alkyl), each of the cycloalkly and alkyl is optionally substituted with at least one substituent selected from NR'R", aryl (such as phenyl), and —NR'CO$_2$R", wherein R' and R" are independently selected from hydrogen, haloalkyl (such as halo$C_{1-6}$alkyl), and alkyl (such as $C_{1-6}$alkyl). In some further embodiments, $R^5$ in Formula (I) is selected from hydrogen; $C_{1-6}$alkyl (such as methyl, ethyl, propyl, isopropyl, butyl, or 3,3-dimethylbutyl) optionally substituted with NR'R"; cyclohexyl; phenyl optionally substituted with NR'R"; and —$COR^9$, wherein $R^9$ is cyclopropyl, or $C_{1-6}$alkyl (such as methyl, ethyl, propyl, isopropyl, or butyl), each of the cyclopropyl and $C_{1-6}$alkyl is optionally substituted with at least one substituent selected from NR'R", aryl (such as phenyl) and —NR'$CO_2$R", wherein R' and R" are independently selected from hydrogen and $C_{1-6}$alkyl (such as methyl, ethyl, propyl, isopropyl, butyl, or tert-butyl).

In some embodiments, $R^4$ and $R^5$ in Formula (I), together with the atoms to which they are attached, form a 3-, 4-, 5-, 6-, 7- or 8-membered saturated, partially or fully unsaturated ring having 0, 1 or 2 heteroatoms independently selected from —$NR^{13}$—, —O—, —S—, —SO— and —$SO_2$-, and said ring is optionally substituted with at least one substituent $R^{12}$ as defined for Formula (I). In some embodiments, $R^4$ and $R^5$ in Formula (I), together with the atoms to which they are attached, form a 5-membered saturated ring having one nitrogen heteroatom.

In some embodiments, at least one pair of ($R^3$ and $R^4$), ($R^5$ and $R^6$), and ($R^7$ and $R^8$) in Formula (I) are alkyl (such as $C_{1-12}$alkyl, further such as $C_{1-6}$alkyl, further such as methyl). In some embodiments, $R^3$ and $R^4$ in Formula (I), which may be the same or different, are each independently selected from hydrogen, alkyl (such as $C_{1-12}$alkyl, further such as $C_{1-6}$alkyl) and OH.

In the second aspect, the at least one compound selected from compounds of Formula (I), stereoisomers thereof, and pharmaceutically acceptable salts thereof is selected from the compounds of Formula (II) below:

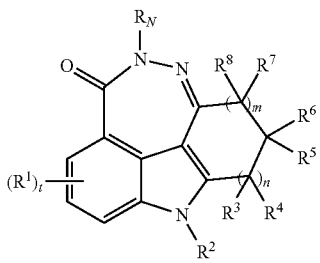

II stereoisomers thereof, and pharmaceutically acceptable salts thereof,
wherein:
$R_N$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;
m and n, which may be the same or different, are each an integer of f 0, 1, 2, or 3;
t is an integer of 0, 1, 2, or 3;
$R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^3$, $R^4$, $R^5$, $R^6$, $R^7$ and $R^8$, which may be the same or different, are each independently selected from hydrogen, halogen, —$NR^9R^{10}$, —$OR^9$, oxo, —$COR^9$, —$CO_2R^9$, —$CONR^9R^{10}$, —$NR^9CONR^{10}R^{11}$, —$NR^9CO_2R^{10}$, —$NR^9SO_2R^{10}$, —$SO_2R^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) to which they are attached, form a 3- to 8-membered saturated, partially or fully unsaturated ring having 0, 1 or 2 heteroatoms independently selected from —$NR^{13}$—, —O—, —S—, —SO— and —$SO_2$-, and said ring is optionally substituted with at least one substituent $R^{12}$, provided that
  when one of $R^3$ and $R^4$ is oxo, the other is absent,
  when one of $R^7$ and $R^8$ is oxo, the other is absent, and
  when one of $R^5$ and $R^6$ is Oxo, the other is absent;
$R^9$, $R^{10}$, and $R^{11}$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;
$R^{12}$ is selected from CN, halogen, haloalkyl, $NO_2$, —NR'R", —OR', oxo, —COR', —$CO_2R'$, —CONR'R", —NR'CONR"R'", —NR'$CO_2R"$, —NR'$SO_2R"$, —$SO_2R'$, alkyl, alkenyl, alkynyl, cycloalkyl, heterocyclyl, aryl, and heteroaryl, wherein R', R", and R'" are independently selected from hydrogen, haloalkyl, alkyl, arylalkyl, alkenyl, alkynyl, cycloalkyl, heterocyclyl, aryl, and heteroaryl, or (R' and R"), and/or (R" and R'") together with the atoms to which they are attached, form a 3- to 8-membered saturated, partially or fully unsaturated ring having 0, 1 or 2 additional heteroatoms independently selected from —$NR^{13}$—, —O—, —S—, —SO— or —$SO_2$-.
$R^{13}$ is selected from hydrogen, alkyl, cycloalkyl, aryl, heteroaryl, and heterocyclyl.

In some embodiments, m and n in Formula (II) are both an integer of 1. In some embodiments, n in Formula (II) is 1 and m in Formula (II) is 2; in other embodiments, n in Formula (II) is 2 and m in Formula (II) is 1.

In some embodiments, t in Formula (II) is 0. In some embodiments, t in Formula (II) is 1 and R' in Formula (II) is selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$ as defined above. In some further embodiments, t in Formula (II) is 1, and $R^1$ in Formula (II) is halogen (such as F, Cl and Br, further such as F) or alkyl (such as $C_{1-12}$alkyl, further such as $C_{1-6}$alkyl). In some further embodiments, t in Formula (II) is 1, and $R^1$ in Formula (II) is halogen (such as F).

In some embodiments, RN in Formula (II) is an alkyl group optionally substituted with at least one substituent selected from hydroxy and alkoxyl. In some further embodiments, RN in Formula (II) is a $C_{1-12}$alkyl group optionally substituted with at least one substituent selected from hydroxy and $C_{1-12}$alkoxyl. In some further embodiments, RN in Formula (II) is a $C_{1-6}$alkyl group optionally substituted with at least one substituent selected from hydroxy and $C_{1-6}$alkoxyl.

In some embodiments, $R^2$ in Formula (II) is hydrogen or alkyl (such as $C_{1-12}$alkyl, further such as $C_{1-6}$alkyl) optionally substituted with at least one substituent $R^{12}$ as defined for Formula (II). In some embodiments, $R^2$ in Formula (II) is alkyl (such as $C_{1-12}$alkyl, further such as $C_1$-6alkyl) optionally substituted with at least one substituent $R^{12}$, wherein $R^{12}$ is selected from —NR'R", —OR', heterocyclyl, and aryl, wherein R', and R" are independently selected from hydrogen, haloalkyl, alkyl, and arylalkyl, or R' and R" together with the atom to which they are attached, form a 3- to 8-membered saturated, partially or fully unsaturated ring having 0, 1 or 2 additional heteroatoms independently selected from —NR$^{13}$—, —O—, —S—, —SO— and —SO$_2$-. In some further embodiments, $R^2$ in Formula (II) is alkyl (such as $C_{1-12}$alkyl, further such as $C_{1-6}$alkyl) optionally substituted with at least one substituent $R^{12}$, wherein $R^{12}$ is selected from —NR'R", —OR$^1$, heterocyclyl, and aryl (such as phenyl), wherein R' and R" are independently selected from hydrogen, haloalkyl (such as halo$C_{1-12}$alkyl, further such as halo$C_{1-6}$alkyl), alkyl (such as $C_{1-12}$alkyl, further such as $C_{1-6}$alkyl), and arylalkyl (such as phenyl$C_{1-12}$alkyl, further such as phenyl$C_{1-6}$alkyl)), or R' and R" together with the atom to which they are attached, form a 3- to 8-membered saturated, partially or fully unsaturated ring having 0, 1 or 2 additional heteroatoms independently selected from —NR$^{13}$—, —O—, —S—, —SO— and —SO$_2$— (such as a 5- or 6-membered saturated ring having 0 or 1 additional heteroatom which is O, further such as 5-membered saturated ring, 6-membered saturated ring, or 6-membered saturated ring having one oxygen heteroatom). In some further embodiments, $R^2$ in Formula (II) is alkyl (such as $C_{1-12}$alkyl, further such as $C_{1-6}$alkyl) optionally substituted with at least one substituent selected from aryl (such as phenyl), 3-, 4-, 5-, 6-, 7-, and 8-membered heterocyclyl containing one nitrogen heteroatom and/or one oxygen heteroatom, —OR', and —NR'R", wherein R' and R" are independently selected from hydrogen, haloalkyl (such as halo$C_{1-12}$alkyl, further such as halo$C_{1-6}$alkyl), alkyl (such as $C_{1-12}$alkyl, further such as $C_{1-6}$alkyl), and arylalkyl (such as phenyl$C_{1-6}$alkyl). In some further embodiments, $R^2$ in Formula (II) is alkyl (such as $C_{1-12}$alkyl, further such as $C_{1-6}$alkyl) optionally substituted with at least one substituent selected from aryl (such as phenyl); 3-, 4-, 5-, 6-, 7-, and 8-membered heterocyclyl group containing one nitrogen heteroatom and/or one oxygen heteroatom selected from pyrrolidinyl, piperidinyl, morpholino, and oxiranyl; —OR'; and —NR'R", wherein R' and R" are independently selected from hydrogen, haloalkyl (such as halo$C_{1-6}$alkyl), alkyl (such as $C_{1-12}$alkyl, further such as $C_{1-6}$alkyl), and arylalkyl (such as phenyl$C_{1-6}$alkyl, further such as phenylmethyl).

In some embodiments, $R^5$ in Formula (II) is selected from hydrogen, alkyl, cycloalkyl, aryl, —COR$^9$, and —COOR$^9$, wherein each of the alkyl, cycloalkyl, and aryl is independently optionally substituted with at least one substituent $R^{12}$, and $R^9$ is alkyl or cycloalkyl optionally substituted with at least one substituent $R^{12}$, and $R^{12}$ is defined as for Formula (II). In some embodiments, $R^5$ in Formula (II) is selected from hydrogen, alkyl, cycloalkyl, aryl, —COR$^9$, and —COOR$^9$, wherein each of the alkyl, cycloalkyl, and aryl is independently optionally substituted with at least one substituent $R^{12}$, and $R^9$ is alkyl or cycloalkyl optionally substituted with at least one substituent $R^{12}$, and $R^{12}$ is selected from NR'R", aryl, and NR'CO$_2$R", wherein R' and R" are independently selected from hydrogen, haoloalkyl and alkyl. In some further embodiments, $R^5$ in Formula (II) is selected from hydrogen; alkyl (such as $C_{1-12}$alkyl, further such as $C_{1-6}$alkyl) optionally substituted with at least one substituent selected from NR'R" and aryl (such as phenyl); cycloalkyl (such as $C_3$, $C_4$, $C_5$, $C_6$, $C_7$, $C_8$cycloalkyl); aryl (such as phenyl) optionally substituted with NR'R"; and —COR$^9$, wherein $R^9$ is cycloalkyl (such as $C_3$, $C_4$, $C_5$, $C_6$, $C_7$, $C_8$cycloalkyl), or alkyl (such as $C_{1-12}$alkyl, further such as $C_{1-6}$alkyl), each of the cycloalkyl and alkyl is optionally substituted with at least one substituent selected from NR'R", aryl (such as phenyl), and —NR'CO$_2$R", wherein R' and R" are independently selected from hydrogen, haloalkyl (such as halo$C_{1-6}$alkyl), and alkyl (such as $C_{1-6}$alkyl). In some further embodiments, $R^5$ in Formula (II) is selected from hydrogen; $C_{1-6}$alkyl (such as methyl, ethyl, propyl, isopropyl, butyl, or 3,3-dimethylbutyl) optionally substituted with NR'R"; cyclohexyl; phenyl optionally substituted with NR'R"; and —COR$^9$, wherein $R^9$ is cyclopropyl, or $C_1$-6alkyl (such as methyl, ethyl, propyl, isopropyl, or butyl), each of the cyclopropyl and $C_{1-6}$alkyl is optionally substituted with at least one substituent selected from NR'R", aryl (such as phenyl), and —NR'CO$_2$R", wherein R' and R" are independently selected from hydrogen and $C_{1-6}$alkyl (such as methyl, ethyl, propyl, isopropyl, butyl, or tert-butyl).

In some embodiments, $R^4$ and $R^5$ in Formula (II), together with the atom(s) to which they are attached, form a 3-, 4-, 5-, 6-, 7- or 8-membered saturated, partially or fully unsaturated ring having 0, 1 or 2 heteroatoms independently selected from —NR$^{13}$—, —O—, —S—, —SO— and —SO$_2$-, and said ring is optionally substituted with at least one substituent $R^{12}$ as defined for Formula (II). In some further embodiments, $R^4$ and $R^5$ in Formula (II), together with the atom(s) to which they are attached, form a 5-membered saturated ring having one nitrogen heteroatom.

In some embodiments, at least one pair of ($R^3$ and $R^4$), ($R^5$ and $R^6$), and ($R^7$ and $R^8$) in Formula (II) are alkyl (such as $C_{1-12}$alkyl, further such as $C_{1-6}$alkyl, further such as methyl). In some embodiments, $R^3$ and $R^4$ in Formula (II), which may be the same different, are each independently selected from hydrogen, alkyl (such as $C_{1-12}$alkyl, further such as $C_{1-6}$alkyl) and OH.

In the third aspect, the at least one compound selected from compounds of Formula (I), stereoisomers thereof, and pharmaceutically acceptable salts thereof is selected from the compounds of Formula (III) below:

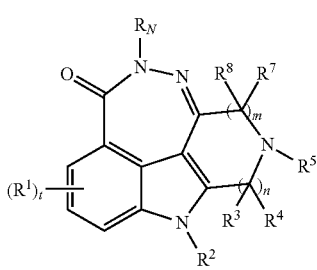

III stereoisomers thereof, and pharmaceutically acceptable salts thereof,
wherein:
$R_N$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

m and n, which may be the same or different, are each an integer of 0, 1, 2, or 3;

t is an integer of 0, 1, 2, or 3;

$R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^3$, $R^4$, $R^5$, $R^7$ and $R^8$, which may be the same or different, are each independently selected from hydrogen, halogen, —$NR^9R^{10}$, —$OR^9$, oxo, —$COR^9$, —$CO_2R^9$, —$CONR^9R^{10}$, —$NR^9CONR^{10}R^{11}$, —$NR^9CO_2R^{10}$, —$NR^9SO_2R^{10}$, —$SO_2R^9$, alkyl, alkenyl, cycloalkyl, aryl, heteroaryl, alkynyl, and heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^7$), and/or ($R^7$ and $R^8$), together with the atom(s) they are attached, form a 3- to 8-membered saturated, partially or fully unsaturated ring having 0, 1 or 2 heteroatoms independently selected from —$NR^{13}$—, —O—, —S—, —SO—, and —$SO_2$-, and said ring is optionally substituted with at least one substituent $R^{12}$, provided that when one of $R^3$ and $R^4$ is oxo, the other is absent, and when one of $R^7$ and $R^8$ is oxo, the other is absent; $R^9$, $R^{10}$, and $R^{11}$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^{12}$ is selected from CN, halogen, haloalkyl, $NO_2$, —NR'R", —OR', oxo, —COR', —$CO_2R'$, —CONR'R", —NR'CONR"R"', —$NR'CO_2R"$, —$NR'SO_2R"$, —$SO_2R'$, alkyl, alkenyl, alkynyl, cycloalkyl, heterocyclyl, aryl, and heteroaryl, wherein R', R", and R"' are independently selected from hydrogen, haloalkyl, alkyl, arylalkyl, alkenyl, alkynyl, cycloalkyl, heterocyclyl, aryl, and heteroaryl, or (R' and R"), and/or (R" and R"') together with the atoms to which they are attached, form a 3- to 8-membered saturated, partially or fully unsaturated ring having 0, 1 or 2 additional heteroatoms independently selected from —$NR^{13}$—, —O—, —S—, —SO— or —$SO_2$-; and $R^{13}$ is selected from hydrogen, alkyl, cycloalkyl, aryl, heteroaryl, and heterocyclyl.

In some embodiments, m and n in Formula (III) are both an integer of 1. In some embodiments, n in Formula (III) is 1, and m in Formula (III) is 2; in other embodiments, n in Formula (III) is 2, and m in Formula (III) is 1.

In some embodiments, t in Formula (III) is 0. In some embodiments, t in Formula (III) is 1, and $R^1$ in Formula (III) is selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$ as defined above. In some further embodiments, t in Formula (III) is 1, and R' in Formula (III) is halogen (such as F, Cl and Br, further such as F) or alkyl (such as $C_{1-12}$alkyl, further such as $C_{1-6}$alkyl). In some further embodiments, t in Formula (III) is 1, and $R^1$ in Formula (III) is halogen (such as F).

In some embodiments, RN in Formula (III) is alkyl optionally substituted with at least one substituent selected from hydroxy and alkoxyl. In some further embodiments, RN in Formula (III) is a $C_{1-12}$alkyl optionally substituted with at least one substituent selected from hydroxy and $C_{1-12}$alkoxyl. In some further embodiments, RN in Formula (III) is a $C_{1-6}$alkyl group optionally substituted with at least one substituent selected from hydroxy and $C_{1-6}$alkoxyl.

In some embodiments, $R^2$ in Formula (III) is hydrogen or alkyl (such as $C_{1-12}$alkyl, further such as $C_{1-6}$alkyl) optionally substituted with at least one substituent $R^{12}$ as defined for Formula (III). In some embodiments, $R^2$ in Formula (III) is alkyl (such as $C_{1-12}$alkyl, further such as $C_{1-6}$alkyl) optionally substituted with at least one substituent $R^{12}$, wherein $R^{12}$ is selected from —NR'R", —OR', heterocyclyl, and aryl, wherein R' and R" are each independently selected from hydrogen, haloalkyl, alkyl, and arylalkyl, or R' and R" together with the atom to which they are attached, form a 3- to 8-membered saturated, partially or fully unsaturated ring having 0, 1 or 2 additional heteroatoms independently selected from —$NR^{13}$—, —O—, —S—, —SO—, and —$SO_2$-. In some further embodiments, $R^2$ in Formula (III) is alkyl (such as $C_{1-12}$alkyl, further such as $C_{1-6}$alkyl) optionally substituted with at least one substituent $R^{12}$, wherein $R^{12}$ is selected from —NR'R", —OR', heterocyclyl, and aryl (such as phenyl), wherein R' and R" are independently selected from hydrogen, haloalkyl (such as halo$C_{1-12}$alkyl, further such as halo$C_{1-6}$alkyl), alkyl (such as $C_{1-12}$alkyl, further such as $C_{1-6}$alkyl), and arylalkyl (such as phenyl$C_{1-12}$alkyl, further such as phenyl$C_{1-6}$alkyl)), or R' and R" together with the atom to which they are attached, form a 3- to 8-membered saturated, partially or fully unsaturated ring having 0, 1 or 2 additional heteroatoms independently selected from —$NR^{13}$-, —O—, —S—, —SO— or —$SO_2$— (such as a 5- or 6-membered saturated ring having 0 or 1 additional heteroatom which is O, further such as 5-membered saturated ring, 6-membered saturated ring, or 6-membered saturated ring having one oxygen heteroatom). In some further embodiments, $R^2$ in Formula (III) is alkyl (such as $C_{1-12}$alkyl, further such as $C_{1-6}$alkyl) optionally substituted with at least one substituent selected from aryl (such as phenyl), 3-, 4-, 5-, 6-, 7-, and 8-membered heterocyclyl group containing one nitrogen heteroatom and/or one oxygen heteroatom, —OR', and —NR'R", wherein R' and R" are independently selected from hydrogen, haloalkyl (such as halo$C_{1-12}$alkyl, further such as halo$C_{1-6}$alkyl), alkyl (such as $C_{1-12}$alkyl, further such as $C_{1-6}$alkyl), and arylalkyl (such as phenyl$C_{1-6}$alkyl). In some further embodiments, $R^2$ in Formula (III) is an alkyl (such as $C_{1-12}$alkyl, further such as $C_{1-6}$alkyl) optionally substituted with at least one substituent selected from aryl (such as phenyl); 3-, 4-, 5-, 6-, 7-, and 8-membered heterocyclyl group containing one nitrogen heteroatom and/or one oxygen heteroatom selected from pyrrolidinyl, piperidinyl, morpholino, and oxiranyl; —OR'; and —NR'R", wherein R' and R" are independently selected from hydrogen, haloalkyl (such as halo$C_{1-6}$alkyl), alkyl (such as $C_{1-12}$alkyl, further such as $C_{1-6}$alkyl), and arylalkyl (such as phenyl$C_{1-6}$alkyl, further such as phenylmethyl).

In some embodiments, $R^5$ in Formula (III) is selected from hydrogen, alkyl, cycloalkyl, aryl, —$COR^9$, and —$COOR^9$, wherein each of the alkyl, cycloalkyl, and aryl is independently optionally substituted with at least one substituent $R^{12}$, and $R^9$ is alkyl or cycloalkyl optionally substituted with at least one substituent $R^{12}$, and $R^{12}$ is defined as for Formula (III). In some embodiments, $R^5$ in Formula (III) is selected from hydrogen, alkyl, cycloalkyl, aryl, —$COR^9$, and —$COOR^9$, wherein each of the alkyl, cycloalkyl, or aryl is independently optionally substituted with at least one substituent $R^{12}$, and $R^9$ is alkyl or cycloalkyl optionally substituted with at least one substituent $R^{12}$, and $R^{12}$ is selected from NR'R", aryl, and $NR'CO_2R"$, wherein R' and R" are independently selected from hydrogen, haoloalkyl and alkyl. In some further embodiments, $R^5$ in Formula (III) is selected from hydrogen; alkyl (such as $C_{1-12}$alkyl, further such as $C_{1-6}$alkyl) optionally substituted with at least one substituent selected from NR'R" and aryl (such as phenyl); cycloalkyl (such as $C_3$, $C_4$, $C_5$, $C_6$, $C_7$, $C_8$ cycloalkyl); aryl (such as phenyl) optionally substituted with NR'R"; and —$COR^9$, wherein $R^9$ is cycloalkyl (such as $C_3$, $C_4$, $C_5$, $C_6$, $C_7$, $C_8$cycloalkyl), or alkyl (such as $C_{1-12}$alkyl, further such as $C_{1-6}$alkyl), each of the cycloalkyl and alkyl is optionally substituted with at least one substituent selected from NR'R", aryl (such as phenyl), and —$NR'CO_2R"$, wherein R' and R" are independently selected from hydrogen, haloalkyl (such as haloC$_{1-6}$alkyl), and alkyl (such as $C_{1-6}$alkyl). In some further embodiments, $R^5$ in Formula (III) is selected from hydrogen; $C_{1-6}$alkyl (such as methyl, ethyl, propyl, isopropyl, butyl, or 3,3-dimethylbutyl) optionally substituted with NR'R"; cyclohexyl; phenyl optionally substituted with NR'R"; and —$COR^9$, wherein $R^9$ is cyclopropyl, or $C_{1-6}$alkyl (such as methyl, ethyl, propyl, isopropyl, or butyl), each of the cycclopropyl and $C_{1-6}$alkyl is optionally substituted with at least one substituent selected from NR'R", aryl (such as phenyl), and —$NR'CO_2R"$, wherein R' and R" are independently selected from hydrogen and $C_{1-6}$alkyl (such as methyl, ethyl, propyl, isopropyl, butyl, or tert-butyl).

In some embodiments, $R^4$ and $R^5$ in Formula (III), together with the atom(s) to which they are attached, form a 3-, 4-, 5-, 6-, 7- or 8-membered saturated, partially or fully unsaturated ring having 0, 1 or 2 additional heteroatoms independently selected from —$NR^{13}$—, —O—, —S—, —SO— or —$SO_2$-, and said ring is optionally substituted with at least one substituent $R^{12}$ as defined for Formula (III). In some further embodiments, $R^4$ and $R^5$ in Formula (III), together with the atom(s) to which they are attached, form a 5-membered saturated ring having one nitrogen heteroatom.

In some embodiments, $R^3$ and $R^4$ in Formula (III), which may be the same or different, are each independently selected from hydrogen, alkyl (such as $C_{1-12}$alkyl, further such as $C_{1-6}$alkyl), and OH.

Also provided herein is at least one compound selected from the following compounds, stereoisomers thereof, and pharmaceutically acceptable salts thereof,

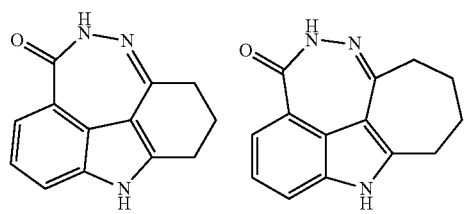

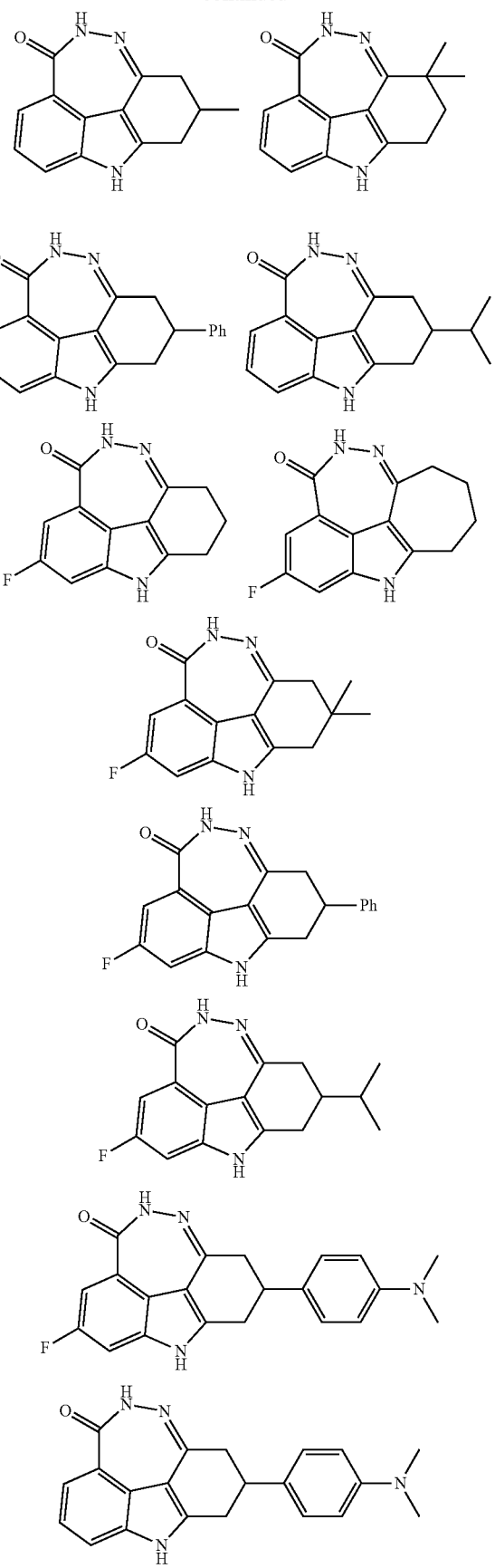

23
-continued
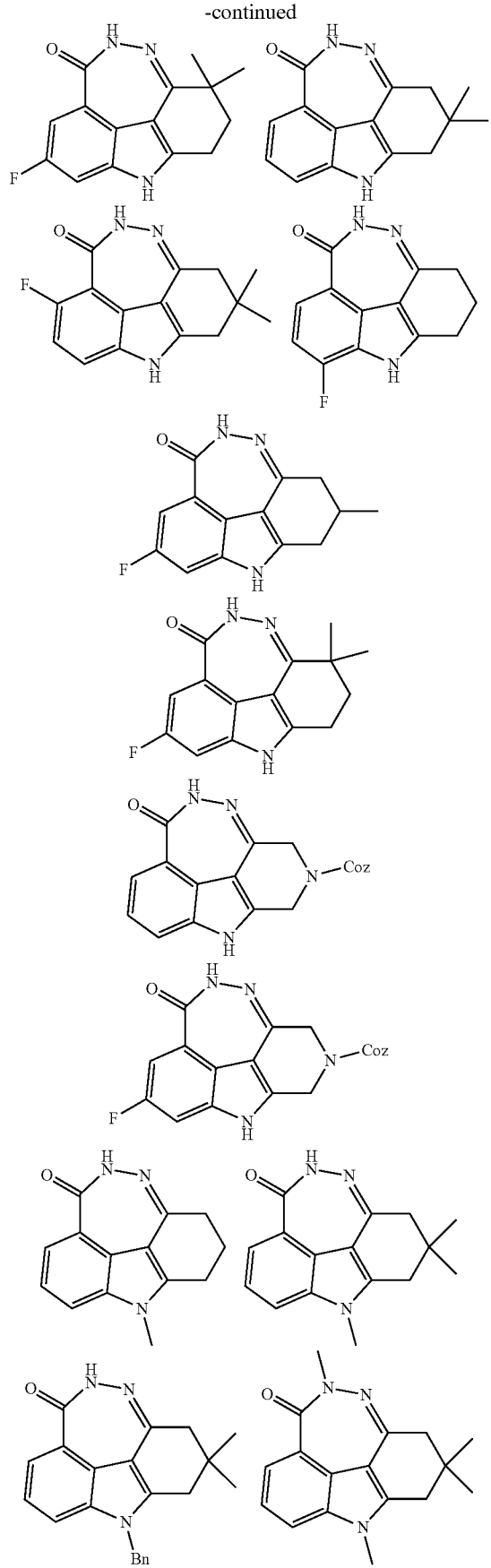
24
-continued
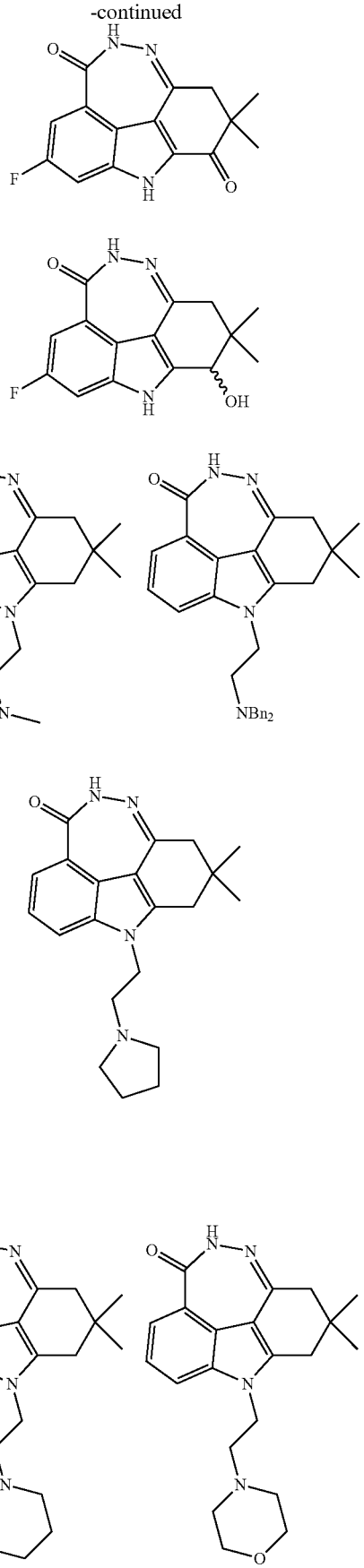

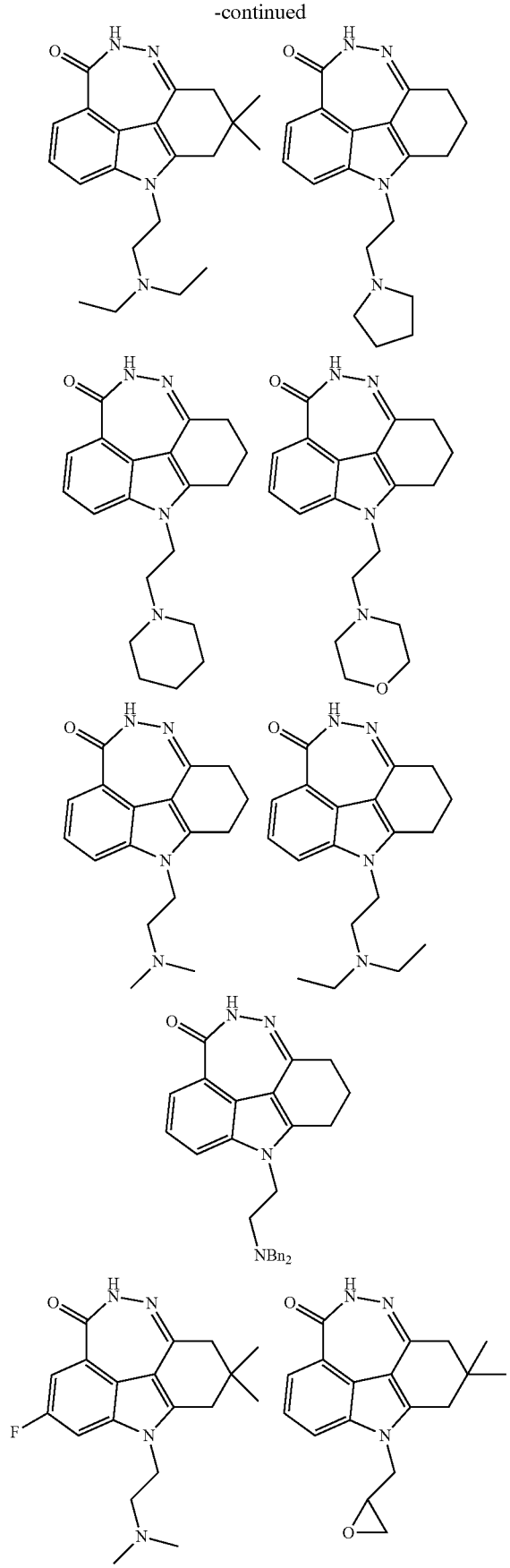
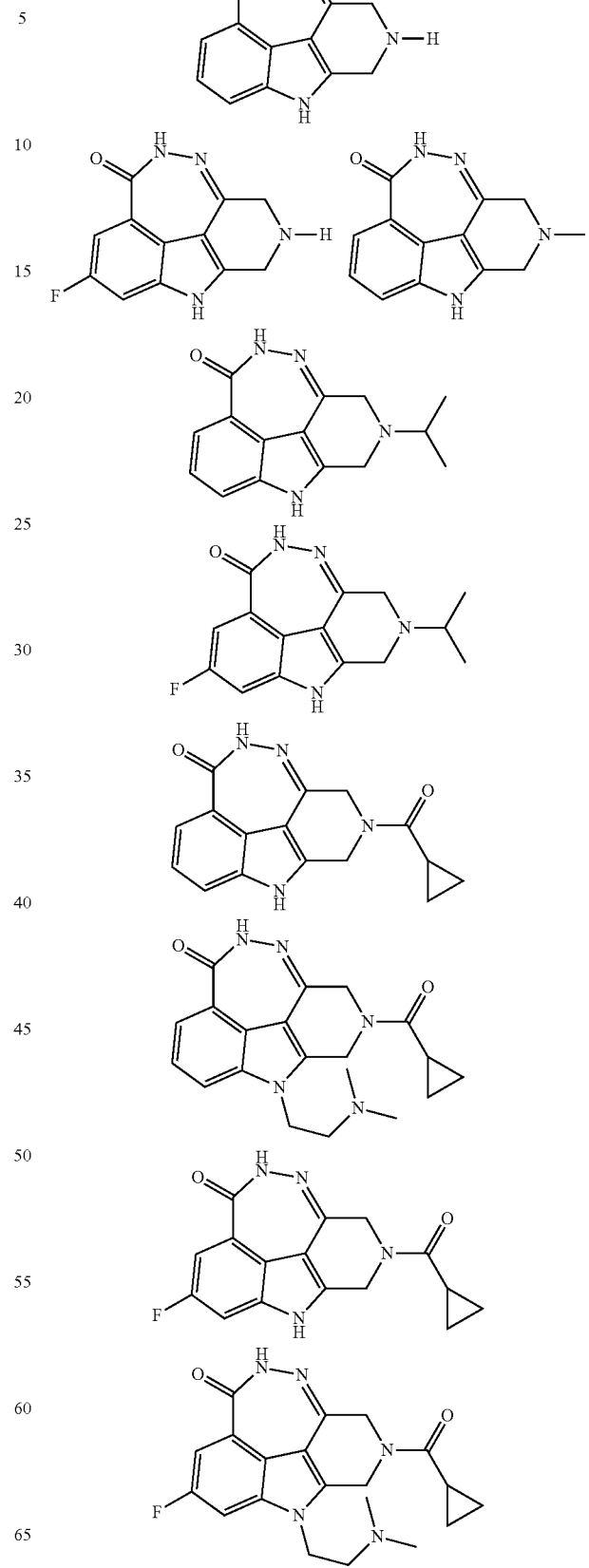

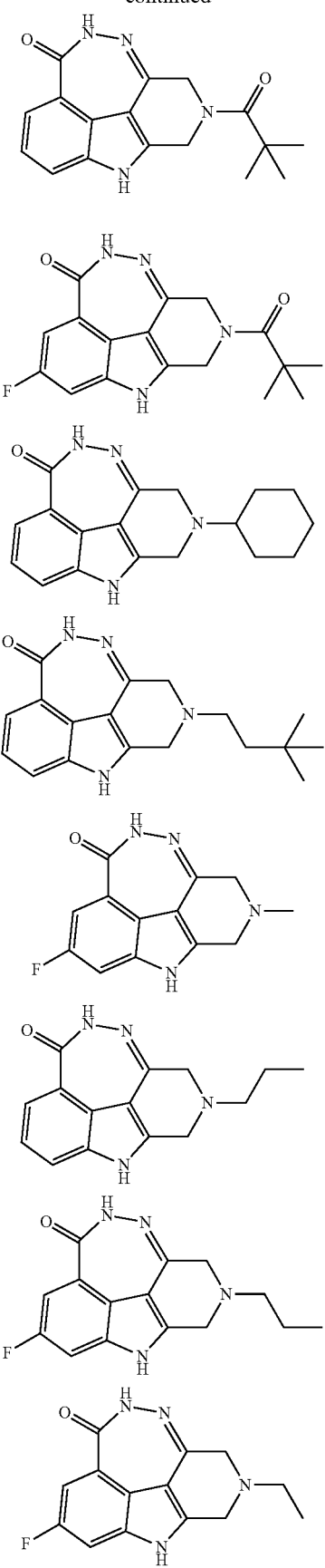
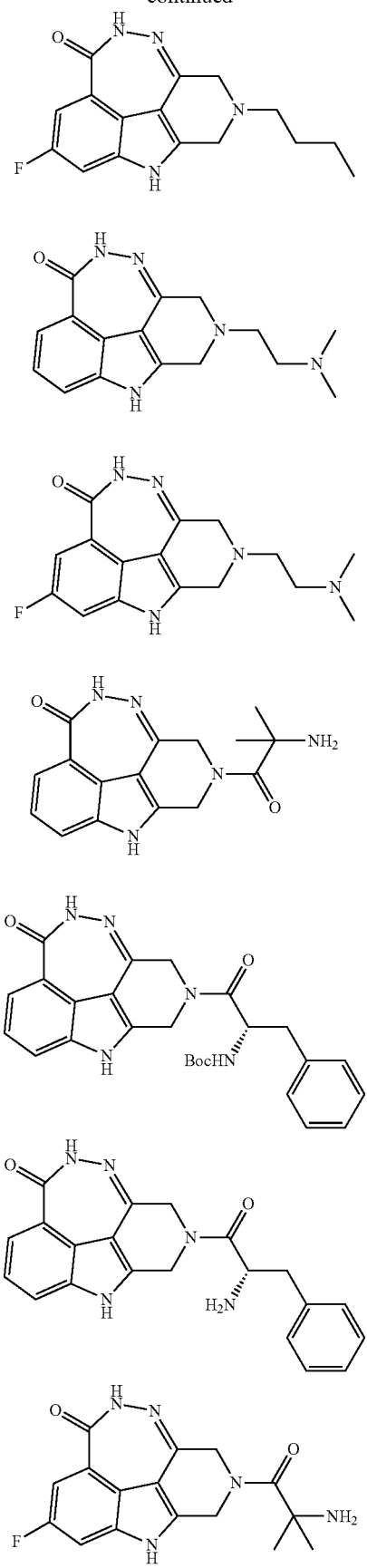

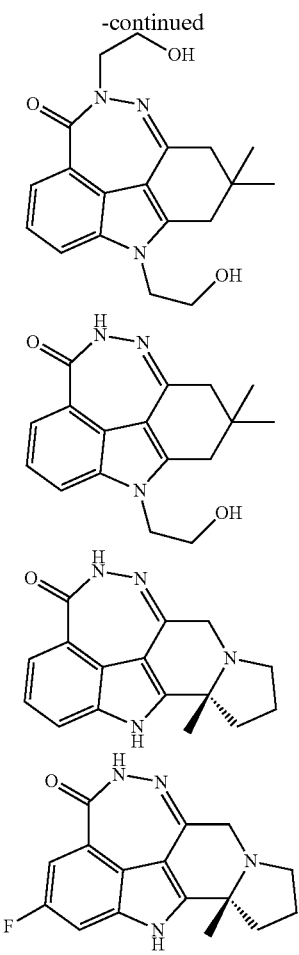

Also provided herein is a method of inhibiting the activity of PARP. The method comprises contacting the PARP with at least one compound, at least one stereoisomer thereof, and/or at least one pharmaceutically acceptable salt thereof described herein in an amount effective to inhibit the activity of the PARP.

Also provided herein is a method of treating at least one disease responsive to inhibition of PARP comprising administering to a subject, such as a mammal or human, in recognized need of such treating for the at least one disease an amount of at least one compound, at least one stereoisomer thereof, and/or at least one pharmaceutically acceptable salt thereof described herein.

The at least one disease can be selected from, for example, ovarian cancer, carcinomas of the breast, colon cancer, leukemia, glioblastomas, lymphomas, melanomas, cervical carcinomas and other cytotoxic cancers.

The at least one compound, at least one stereoisomer thereof, and/or at least one pharmaceutically acceptable salt thereof disclosed herein may be employed alone or in combination with radiation and chemotherapy by, for example, increasing apoptosis of cancer cells, limiting tumor growth, decreasing metastasis, and prolonging the survival of tumor-bearing mammals.

In some embodiments, the at least one compound, at least one stereoisomer thereof, and/or at least one pharmaceutically acceptable salt thereof disclosed herein can be used in combination with at least one additional therapeutic agent, such as at least one additional chemotherapeutic agent.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-α and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG 1571 (SU 5271, Sugen); alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CBI-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gamma1I and calicheamicin omega1I (Angew Chem. Intl. Ed. Engl. (1994) 33: 183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle Formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY 117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, such as those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the at least one compound, at least one stereoisomer thereof, and/or at least one pharmaceutically acceptable salt thereof disclosed herein may, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Also provided herein is a composition comprising at least one compound, at least one stereoisomer thereof, and/or at least one pharmaceutically acceptable salt thereof disclosed herein, and at least one pharmaceutically acceptable carrier.

The composition comprising at least one compound, at least one stereoisomer thereof, and/or at least one pharmaceutically acceptable salt disclosed herein can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The at least one compound, at least one stereoisomer thereof, and/or at least one pharmaceutically acceptable salt thereof disclosed herein can be administered orally in solid dosage forms, such as capsules, tablets, troches, dragées, granules and powders, or in liquid dosage forms, such as elixirs, syrups, emulsions, dispersions, and suspensions. The at least one compound, at least one stereoisomer thereof, and/or at least one pharmaceutically acceptable salt thereof disclosed herein can also be administered parenterally, in sterile liquid dosage forms, such as dispersions, suspensions or solutions. Other dosages forms that can also be used to administer the at least one compound, at least one stereoisomer thereof, and/or at least one pharmaceutically acceptable salt thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound, at least one stereoisomer thereof, and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients.

Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

Suitable in vitro assays can be used to preliminarily evaluate the efficacy of the at least one compound, at least one stereoisomer thereof, and/or at least one pharmaceutically acceptable salt thereof disclosed herein, in inhibiting the activity of PARP. The at least one compound, at least one stereoisomer thereof, and/or at least one pharmaceutically acceptable salt thereof disclosed herein can further be examined for efficacy in treating cancer by in vivo assays. For example, the at least one compound, at least one stereoisomer thereof, and/or the at least one pharmaceutically acceptable salts thereof disclosed herein can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the at least one compound, at least one stereoisomer thereof, and/or at least one pharmaceutically acceptable salt thereof tested. Based on the results, an appropriate dosage range and administration route for animals, such as humans, can also be determined.

For administration by inhalation, the at least one compound, at least one stereoisomer thereof, and at least one pharmaceutically acceptable salt thereof disclosed herein may be conveniently delivered in the form of an aerosol spray presentation from pressurized packs or nebulisers. The at least one compound, at least one stereoisomer thereof, and/or at least one pharmaceutically acceptable salt thereof disclosed herein may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of at least one compound, at least one stereoisomer thereof, and/or at least one pharmaceutically acceptable salt thereof disclosed herein in at least one suitable propellant, selected, for example, from fluorocarbons and hydrocarbons.

For ocular administration, an ophthalmic preparation may be formulated with an appropriate weight percentage of a solution or suspension of the at least one compound, at least one stereoisomer thereof, and/or at least one pharmaceutically acceptable salt thereof disclosed herein in an appropriate ophthalmic vehicle, such that the at least one compound, stereoisomers thereof, and pharmaceutically acceptable salts thereof disclosed herein is maintained in contact with the ocular surface for a sufficient time period to allow the compound to penetrate the corneal and internal regions of the eye.

Useful pharmaceutical dosage-forms for administration of the at least one compound, at least one stereoisomer thereof, and/or at least one pharmaceutically acceptable salt thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain desired results.

In some embodiments, a large number of unit capsules can be prepared by filling standard two-piece hard gelatin capsules each with, for example, 100 milligrams of the at least one compound, stereoisomers thereof, and pharmaceutically acceptable salts thereof disclosed herein in powder, 150 milligrams of lactose, 50 milligrams of cellulose, and 6 milligrams magnesium stearate.

In some embodiments, a mixture of the at least one compound, at least one stereoisomer thereof, and/or at least one pharmaceutically acceptable salt thereof disclosed herein in a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the at least one compound, at least one stereoisomer thereof, and/or at least one pharmaceutically acceptable salt thereof disclosed herein, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound, at least one stereoisomer thereof, and/or at least one pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided at least one compound, at least one stereoisomer thereof, and/or at least one pharmaceutically acceptable salt thereof disclosed herein, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the at least one compound, at least one stereoisomer thereof, and/or at least one pharmaceutically acceptable salt thereof disclosed herein are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The at least one compound, stereoisomers thereof, and pharmaceutically acceptable salts thereof disclosed herein can be administered as the sole active ingredient or in combination with at least one second active ingredient, selected, for example, from other active ingredients known to be useful for treating cancers in a patient.

General Synthetic Schemes

The compounds disclosed herein, and/or the pharmaceutically acceptable salts thereof, can be synthesized from commercially available starting materials taken together with the disclosure herein. The following schemes illustrate methods for preparation of some of the compounds disclosed herein.

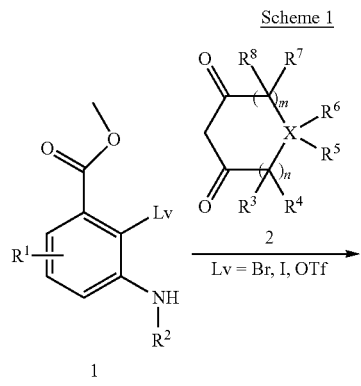

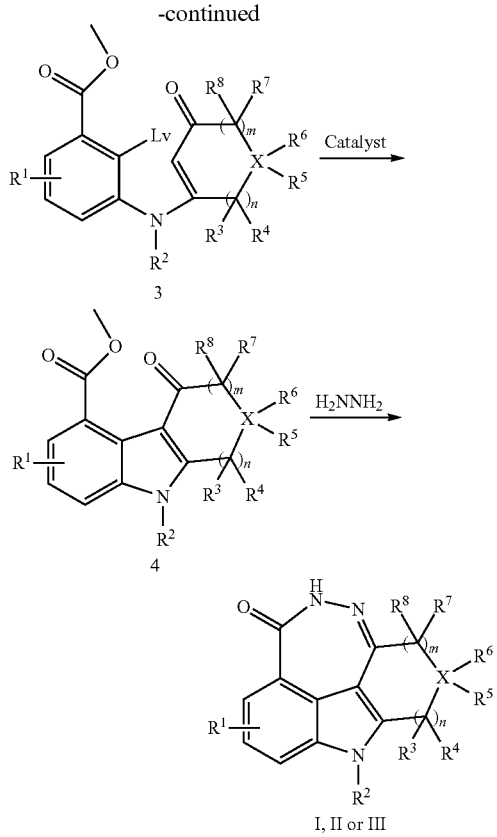

In this scheme, an alkyl 3-amino-2-Lv-benzoate (Lv=leaving group, such as Br, I, OTf) of formula 1 is reacted with a cyclic 1,3-carbonyls of formula 2 to provide an enaminone of formula 3. The subsequent cyclization under a catalyst, such as palladium, gives an alkyl oxocarbazole carboxylate of formula 4 which is subsequently cyclized with hydrazine to provide the diazepinocarbazolone derivative of Formula (I), (II) or (III).

The first step of this scheme can be conducted in Dean-Stark apparatus in a solvent such as toluene under reflux. The resulting enaminone of formula 3 is purified on a flash column.

The second step of this sequence can be conducted using a palladium/phosphine catalyst at elevated temperature in acetonitrile or DMF and this intramolecular Heck reaction (Bozell, J. J., Hegedus, L. S. J. Org. Chem. 1981, 46, 2561; Maruyama, J., Yamashida, H., Watanabe, T., Arai, S., Nishida, A. Tetrahedron 2009, 65, 1327, incorporated herein by reference) can be usually completed in about 5-24 hours. The alkyl oxocarbazole carboxylate of formula 4 can be then isolated using standard conditions for the workup and it may be purified by either chromatographic methods or by recrystallization.

The third step of the synthesis of the novel compounds of Formula (I) is an intermolecular cyclization reaction of a compound of formula 4 to provide the diazepinocarbazolone derivative of Formula (I), (II) or (III) as shown Scheme 1. This cyclization reaction can be typically conducted using 1-2 equivalents of hydrous hydrazine and the appropriate alcohol as solvent. The cyclization reaction can be typically conducted at a temperature ranging from 50° C. to the refluxing temperature of the alcohol and it can be completed, for instance, in 0.25 to 4 hours.

The synthesis of some of the compounds of Formula (III) can be described in Scheme 2. The compound of formula a which is also a compound of Formula (III), can be prepared according to Scheme 1.

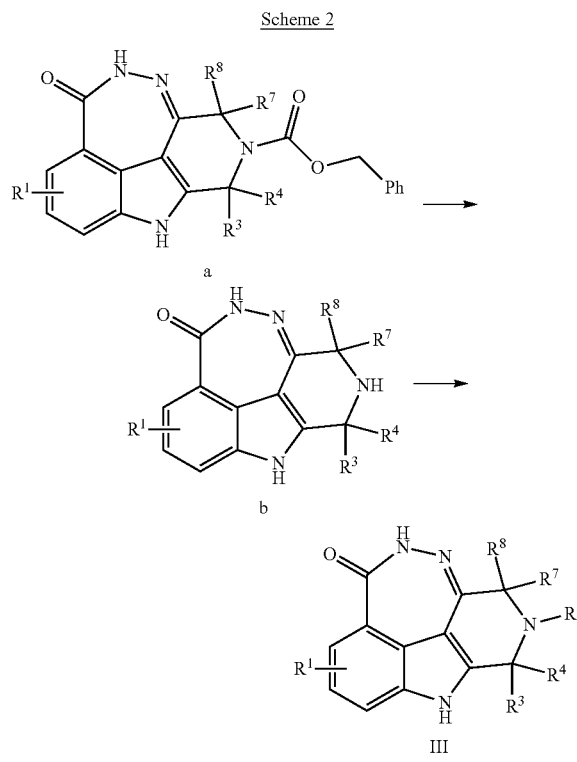

Scheme 2

The compound of formula a is de-protected to give a compound of formula b (which is also a compound of Formula (III)). Further reaction of the compound of formula b with electrophile such as alkyl halide, aryl halides, acids, acyl chlorides, sulfonyl chlorides, aldehyde, ketone, etc, gives some of the compounds of Formula (III) under the corresponding alkylation, coupling, or reductive alkylation conditions.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using pre-packed silica gel cartridges.

$^1$H NMR spectra were recorded on a Varian instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by Chemdraw version 12.0.

In the following examples, the abbreviations below are used:

AcOH Acetic acid
Aq Aqueous
Brine Saturated aqueous sodium chloride solution
$CH_2Cl_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
G grams
h or hr hour
HATU 2-(1H-7-Azabenzotriazol-1-yl)-1,1,3,3-tetramethyl uronium hexafluorophosphate Methanaminium
HCl Hydrochloric acid
HPLC High-performance liquid chromatography
IPA 2-propanol
i-PrOH Isopropyl alcohol
Mg milligrams
mL milliliters
Mmol millimole
MeCN Acetonitrile
MeOH Methanol
Min minutes
ms or MS Mass pectrum
$Na_2SO_4$ Sodium sulfate
Rt Retention time
Rt or rt Room temperature
TFA Trifluoroacetic acid
THF tetrahydrofuran
TLC thin layer chromatography
μL microliters In the following examples, the abbreviations below are used:

Example 1: Synthesis of Compounds 1-19

Compound 1: 2,3,5,10-tetrahydro-[1,2]diazepino[3,4,5,6-def]carbazol-6(1H)-one

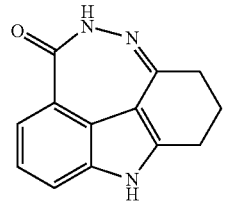 [SMILES: O=C1NN=C2CCCc3[nH]c4cccc1c4c32]

Step 1: Methyl 2-bromo-3-((3-oxocyclohex-1-en-1-yl)amino)benzoate

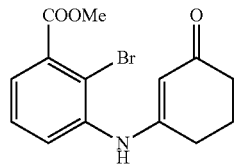 [SMILES: COC(=O)c1cccc(NC2=CC(=O)CCC2)c1Br]

Methyl 3-amino-2-bromobenzoate (2.39 g, 10.0 mmol) and cyclohexane-1,3-dione (1.12 g, 10.0 mmol) were dissolved in 10 mL of acetic acid at 25° C., under nitrogen. The mixture was stirred at 80° C. for 8 hours. The resultant solid was purified by chromatography column on silica gel (elution with hexane/ethyl acetate) to afford 2.46 g (76%) of methyl 2-bromo-3-((3-oxocyclohex-1-en-1-yl)amino)benzoate as a tan foam. $^1$H NMR (CDCl$_3$-d1) δ 7.53-7.55 (m, 2H), 7.37 (dd, 1H, J=7.2, 8.4 Hz), 6.34 (br s, 1H), 5.57 (s, 1H), 3.95 (s, 3H), 2.56-2.59 (m, 2H), 2.40-2.42 (m, 2H), and 2.08-2.11 (m, 2H).MS (ESI) m/e [M+1]$^+$ 324.0.

Step 2: Methyl 4-oxo-2,3,4,9-tetrahydro-H-carbazole-5-carboxylate

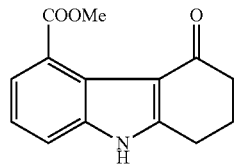 [SMILES: COC(=O)c1cccc2[nH]c3c(c12)C(=O)CCC3]

A mixture of methyl 2-bromo-3-(3-oxocyclohex-1-enylamino)benzoate (0.97 g, 3.0 mmol), palladium acetate (0.14 g, 0.6 mmol), tri-o-tolylphosphine (0.73 g, 2.4 mmol), and triethylamine (0.38 g, 3.6 mmol) in acetonitrile (10 mL) was heated in a sealed tubule flushed with nitrogen at 100° C. for 20 h. The cooled reaction mixture was diluted with DCM (3×50 mL) and water (10 mL). The organic layer was separated, washed with water, dried (Na$_2$SO$_4$), and concentrated. The remaining residue was chromatographed on silica gel, eluted with gradient 0-100% EtOAc in hexane to afford the title compound (0.61 g, 84%). $^1$H NMR (CDCl$_3$-d1) δ 9.47 (s, 1H), 7.36-7.40 (m, 2H), 7.22 (t, 1H, J=7.8 Hz), 2.90-2.92 (m, 2H), 2.51-2.54 (m, 2H), and 2.14-2.16 (m, 2H).MS (ESI) m/e [M+1]$^+$ 244.0.

Step 3: 2,3,5,10-Tetrahydro-[1,2]diazepino[3 4,5,6-def]carbazol-6(1H)-one

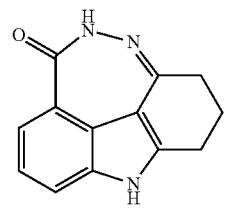

A solution of compound methyl 4-oxo-2,3,4,9-tetrahydro-1H-carbazole-5-carboxylate (73 mg, 0.3 mmol), acetic acid (0.15 mL, 2.6 mmol), and hydrazine hydrate (0.86 mL, 1.5 mmol) in methanol (4 mL) was heated at reflux. After 8 h, the solid was collected by hot filtration and washed with water, EtOAc, and dichloromethane, to give the target compound (42 mg, 62%). $^1$H NMR (DMSO-d6) δ 11.70 (s, 1H), 9.79 (s, 1H), 7.36-7.38 (m, 2H), 7.05 (t, 1H, J=7.8 Hz), 2.77-2.79 (m, 2H), 2.35-2.37 (m, 2H), and 1.92-1.93 (m, 2H).MS (ESI) m/e [M+1]$^+$ 226.0.

The following examples, Compounds 2 through 19, were prepared according to the procedure for Compound 1 by using the corresponding substituted or unsubstituted methyl 3-amino-2-bromobenzoate and cyclic 1,3-dione under appropriate conditions that could be recognized by one skilled in the art.

| Compound No. | Name | $^1$H NMR data LC/MS m/z (M + 1) | Structure |
|---|---|---|---|
| 2 | 5,6,7,8-tetrahydro-4H-1,9,10-triazaindeno[2,1,7-kla]heptalen-11(10H)-one | (DMSO-d$_6$) δ 11.74 (s, 1H), 9.79 (s, 1H), 7.46 (d, 1H, J = 7.8 Hz), 7.38 (d, 1H, J = 7.8 Hz), 7.07 (t, 1H, J = 7.8 Hz), 2.98-3.01 (m, 2H), 2.59-2.61 (m, 2H), 1.89-1.94 (m, 2H), and 1.70-1.84 (m, 2H) MS (ESI) m/e [M + 1]$^+$ 240.0. | 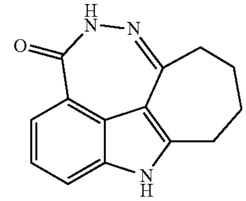 [SMILES: O=C1NN=C2CCCCc3[nH]c4cccc1c4c32] |

-continued

| Compound No. | Name | ¹H NMR data LC/MS m/z (M + 1) | Structure |
|---|---|---|---|
| 3 | 2-methyl-2,3,5,10-tetrahydro-[1,2]diazepino[3,4,5,6-def]carbazol-6(1H)-one | (DMSO-d$_6$) δ 11.70 (s, 1H), 9.81 (s, 1H), 7.40-7.42 (m, 2H), 7.08 (t, 1H, J = 7.8 Hz), 2.88-2.92 (m, 1H), 2.40-2.42 (m, 2H), 2.14-2.19 (m, 2H), and 1.10 (d, 3H, J = 6.0 Hz). MS (ESI) m/e [M + 1]$^+$ 240.0. | 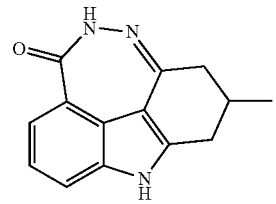 [SMILES: CC1CC2=NNC(=O)c3cccc4[nH]c(c2c34)C1] |
| 4 | 3,3-dimethyl-2,3,5,10-tetrahydro-[1,2]diazepino[3,4,5,6-def]carbazol-6(1H)-one | (DMSO-d$_6$) δ 11.70 (s, 1H), 9.89 (s, 1H), 7.39-7.41 (m, 2H), 7.08 (t, 1H, J = 7.8 Hz), 2.82-2.84 (m, 1H), 1.79-1.81 (m, 2H) and 1.16 (s, 6H). MS (ESI) m/e [M + 1]$^+$ 254.0. | 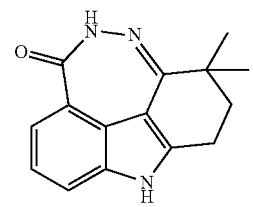 [SMILES: CC1(C)CCc2[nH]c3cccc4c3c2C1=NNC4=O] |
| 5 | 2-phenyl-2,3,5,10-tetrahydro-[1,2]diazepino[3,4,5,6-def]carbazol-6(1H)-one | (DMSO-d$_6$) δ 11.74 (s, 1H), 9.84 (s, 1H), 7.21-7.42 (m, 7H), 7.07 (t, 1H, J = 7.8 Hz), 3.24-3.28 (m, 2H), 3.01-3.08 (m, 1H), and 2.70-2.75 (m, 2H). MS (ESI) m/e [M + 1]$^+$ 302.0. | 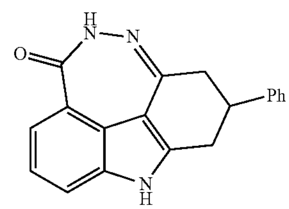 [SMILES: O=C1NN=C2CC(c3ccccc3)Cc3[nH]c4cccc1c4c32] |
| 6 | 2-isopropyl-2,3,5,10-tetrahydro-[1,2]diazepino[3,4,5,6-def]carbazol-6(1H)-one | (DMSO-d$_6$) δ 11.70 (s, 1H), 9.82 (s, 1H), 7.42 (m, 2H), 7.09 (t, 1H, J = 7.8 Hz), 2.84-2.87 (m, 1H), 2.59-2.64 (m, 1H), 2.42-2.49 (m, 1H), 2.20-2.24 (m, 1H), 1.82-1.85 (m, 1H), 1.69-1.72 (m, 1H), and 0.98 (6H, d, J = 7.2 Hz). MS (ESI) m/e [M + 1]$^+$ 268. | 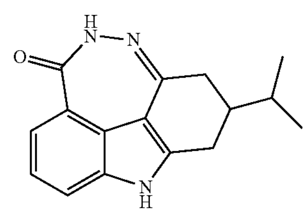 [SMILES: CC(C)C1CC2=NNC(=O)c3cccc4[nH]c(c2c34)C1] |
| 7 | 8-fluoro-2,3,5,10-tetrahydro-[1,2]diazepino[3,4,5,6-def]carbazol-6(1H)-one | (DMSO-d$_6$) δ 11.83 (s, 1H), 10.03 (s, 1H), 7.23 (dd, 1H, J = 10.8, 1.8 Hz), 7.12 (dd, 1H, J = 11.4, 1.8 Hz), 2.76-2.78 (m, 2H), 2.35-2.37 (m, 2H), 1.91-1.93 (m, 2H). MS (ESI) m/e [M + 1]$^+$ 244. | 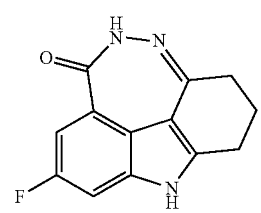 [SMILES: O=C1NN=C2CCCc3[nH]c4cc(F)cc1c4c32] |
| 8 | 2-fluoro-5,6,7,8-tetrahydro-4H-4,9,10-tiazaindeno[2,1,7-kla]heptalen-11(10H)-one | (DMSO-d$_6$) δ 11.84 (s, 1H), 10.02 (s, 1H), 7.17-7.22 (m, 2H), 2.95-2.97 (m, 2H), 2.56-2.58 (m, 2H), 1.77-1.88 (m, 4H). MS (ESI) m/z [M + 1]$^+$ 258. | 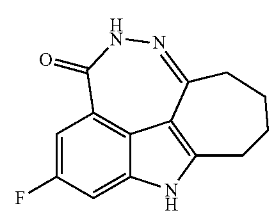 [SMILES: O=C1NN=C2CCCCc3[nH]c4cc(F)cc1c4c32] |
| 9 | 8-fluoro-2,2-dimethyl-2,3,5,10-tetrahydro-[1,2]diazepino[3,4,5,6-def]carbazol-6(1H)-one | (DMSO-d$_6$) δ 11.84 (s, 1H), 10.08 (s, 1H), 7.29 (dd, 1H, J = 10.8, 1.8 Hz), 7.18 (dd, 1H, J = 11.4, 1.8 Hz), 2.63-2.67 (m, 2H), 2.25-2.26 (m, 2H), 1.86 (s, 6H). MS (ESI) m/e [M + 1]$^+$ 272. | 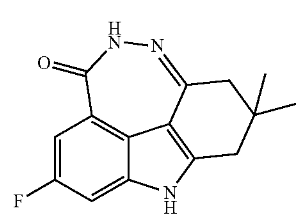 [SMILES: CC1(C)CC2=NNC(=O)c3cc(F)cc4[nH]c(c2c34)C1] |

-continued

| Compound No. | Name | ¹H NMR data LC/MS m/z (M + 1) | Structure |
|---|---|---|---|
| 10 | 8-fluoro-2-phenyl-2,3,5,10-tetrahydro-[1,2]diazepino[3,4,5,6-def]carbazol-6(1H)-one | (DMSO-d$_6$) δ 11.92 (s, 1H), 10.11 (s, 1H), 7.18-7.40 (m, 7H), 3.31-3.32 (m, 1H), 3.05-3.07 (m, 2H), 2.74-2.77 (m, 1H), 2.55-2.56 (m, 1H). MS (ESI) m/e [M + 1]$^+$ 320. | 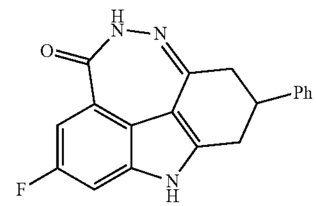 [SMILES: O=C1NN=C2CC(c3ccccc3)Cc3[nH]c4cc(F)cc1c4c32] |
| 11 | 8-fluoro-2-isopropyl-2,3,5,10-tetrahydro-[1,2]diazepino[3,4,5,6-def]carbazol-6(1H)-one | (DMSO-d$_6$) δ 11.82 (s, 1H), 10.04 (s, 1H), 7.15-7.29 (m, 2H), 2.82-2.85 (m, 1H), 2.57-2.61 (m, 1H), 2.41-2.44 (m, 1H), 2.19-2.44 (m, 1H), 1.82-1.83 (m, 1H), 1.69-1.71 (m, 1H), 0.97 (d, 6H, J = 9.0 Hz) MS (ESI) m/e [M + 1]$^+$ 286. | 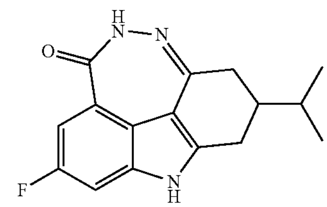 [SMILES: CC(C)C1CC2=NNC(=O)c3cc(F)cc4[nH]c(c2c34)C1] |
| 12 | 2-(4-(dimethylamino)phenyl)-8-fluoro-2,3,5,10-tetrahydro-[1,2]diazepino[3,4,5,6-def]carbazol-6(1H)-one | (DMSO-d$_6$) δ 11.89 (s, 1H), 10.09 (s, 1H), 7.29 (dd, 1H, J = 9.0, 1.8 Hz), 7.17-7.19 (m, 3H), 6.69 (d, 2H, J = 8.4 Hz), 3.19-3.21 (m, 1H), 2.98-3.00 (m, 2H), 2.86 (s, 6H), 2.66-2.69 (m, 1H), 2.48-2.51 (m, 1H). MS (ESI) m/e [M + 1]$^+$ 363. | 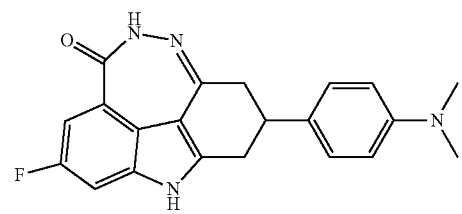 [SMILES: CN(C)c1ccc(C2CC3=NNC(=O)c4cc(F)cc5[nH]c(c3c45)C2)cc1] |
| 13 | 2-(4-(dimethylamino)phenyl)-2,3,5,10-tetrahydro-[1,2]diazepino[3,4,5,6-def]carbazol-6(1H)-one | (DMSO-d$_6$) δ 11.76 (s, 1H), 9.84 (s, 3H), 7.42 (d, 2H, J = 7.8 Hz), 7.03-7.17 (m, 3H), 6.69 (d, 2H, J = 7.8 Hz), 3.16-3.17 (m, 1H), 2.99-3.01 (m, 2H), 2.70 (s, 6H), 2.65-2.68 (m, 1H), 2.48-2.50 (m, 1H). MS (ESI) m/e [M + 1]$^+$ 345. | 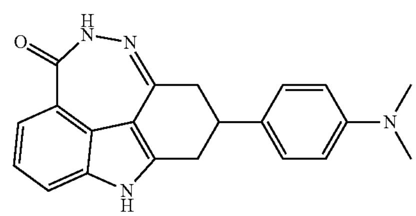 [SMILES: CN(C)c1ccc(C2CC3=NNC(=O)c4cccc5[nH]c(c3c45)C2)cc1] |
| 14 | 8-fluoro-3,3-dimethyl-2,3,5,10-tetrahydro-[1,2]diazepino[3,4,5,6-def]carbazol-6(1H)-one | (DMSO-d$_6$) δ 11.7 (s, 1H), 10.1 (s, 1H), 7.26 (dd, 1H, J = 9.6, 2.4 Hz), 7.16 (dd, 1H, J = 10.2, 2.4 Hz), 2.81-2.83 (m, 2H), 1.74-1.81 (m, 2H), and 1.16 (s, 6H). MS (ESI) m/e [M + 1]$^+$ 272. | 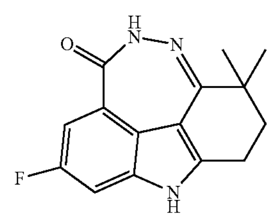 [SMILES: CC1(C)CCc2[nH]c3cc(F)cc4c3c2C1=NNC4=O] |
| 15 | 2,2-dimethyl-2,3,5,10-tetrahydro-[1,2]diazepino[3,4,5,6-def]carbazol-6(1H)-one | (DMSO-d$_6$) δ 11.69 (s, 1H), 9.84 (s, 1H), 7.42 (d, 2H, J = 7.8 Hz), 7.09 (t, 1H, J = 7.8 Hz), 2.67 (s, 2H), 2.23 (s, 2H), 1.05 (s, 6H). MS (ESI) m/e [M + 1]$^-$ 254. | 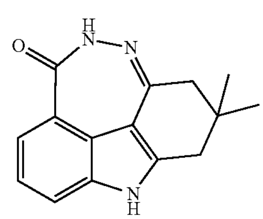 [SMILES: CC1(C)CC2=NNC(=O)c3cccc4[nH]c(c2c34)C1] |
| 16 | 7-fluoro-2,2-dimethyl-2,3,5,10-tetrahydro-[1,2]diazepino[3,4,5,6-def]carbazol-6(1H)-one | (DMSO-d$_6$) δ 11.75 (s, 1H), 9.60 (s, 1H), 7.41 (dd, 1H, J = 9.0, 3.0 Hz), 6.87 (dd, 1H, J = 120, 3.0 Hz), 2.65 (s, 2H), 2.21 (s, 2H), 1.05 (s, 6H). MS (ESI) m/e [M + 1]$^+$ 272. | 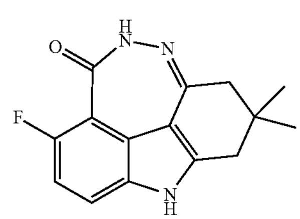 [SMILES: CC1(C)CC2=NNC(=O)c3c(F)ccc4[nH]c(c2c34)C1] |

| Compound No. | Name | ¹H NMR data LC/MS m/z (M + 1) | Structure |
|---|---|---|---|
| 17 | 9-fluoro-2,3,5,10-tetrahydro-[1,2]diazepino[3,4,5,6-def]carbazol-6(1H)-one | (DMSO-d$_6$) δ 12.26 (s, 1H), 9.93 (s, 1H), 7.43 (dd, 1H, J = 8.4, 4.8 Hz), 6.96 (dd, 1H, J = 13.3, 8.4 Hz), 2.82-2.85 (m, 2H), 2.41-2.43 (m, 2H), 1.97-1.99 (m, 2H). MS (ESI) m/e [M + 1]⁻ 244. | 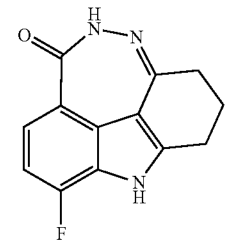 [SMILES: O=C1NN=C2CCCc3[nH]c4c(F)ccc1c4c32] |
| 18 | 8-fluoro-2-methyl-2,3,5,10-tetrahydro-[1,2]diazepino[3,4,5,6-def]carbazol-6(1H)-one | (DMSO-d$_6$) δ 12.1 (s, 1H), 10.0 (s, 1H), 7.26 (dd, 1H, J = 9.6, 2.4 Hz), 7.16 (dd, 1H, J = 10.2, 2.4 Hz), 2.87-2.91 (m, 1H), 2.40-2.43 (m, 2H), 2.15-2.19 (m, 2H), and 1.10 (d, 3H, J = 6.0 Hz). MS (ESI) m/e [M + 1]⁺ 258. | 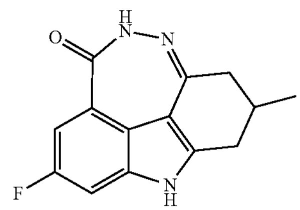 [SMILES: CC1CC2=NNC(=O)c3cc(F)cc4[nH]c(c2c34)C1] |
| 19 | 8-fluoro-3,3-dimethyl-2,3,5,10-tetrahydro-[1,2]diazepino[3,4,5,6-def]carbazol-6(1H)-one | (DMSO-d$_6$) δ 11.7 (s, 1H), 10.1 (s, 1H), 7.26 (dd, 1H, J = 9.6, 2.4 Hz), 7.16 (dd, 1H, J = 10.2, 2.4 Hz), 2.81-2.83 (m, 2H), 1.74-1.81 (m, 2H), and 1.16 (s, 6H). MS (ESI) m/e [M + 1]⁺ 272. | 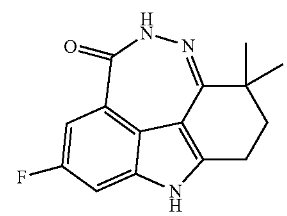 [SMILES: CC1(C)CCc2[nH]c3cc(F)cc4c3c2C1=NNC4=O] |

Example 2: Synthesis of Compounds 20-21

Compound 20 Benzyl 8-oxo-3,4,8,9-tetrahydro-2,4,9,10-tetraazacyclohepta[def]fluorene-2(1H)-carboxylate

Step 1: Benzyl 3-((2-bromo-3-(methoxycarbonyl)phenol)amino)-5-oxo-5 6-dihydropyridine-1(2H)-carboxylate

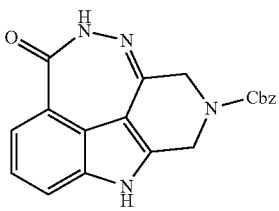 [SMILES: O=C1NN=C2CN(C(=O)OCc3ccccc3)Cc3[nH]c4cccc1c4c32]

Methyl 3-amino-2-bromobenzoate (0.25 g, 1.1 mmol) and benzyl 3,5-dioxopiperidine-1-carboxylate (0.13 g, 0.55 mmol) were dissolved in 10 mL of acetic acid at 25° C., under nitrogen. The mixture was stirred for 8 hours at 70° C. The resultant solid was purified by chromatography column on silica gel (elution with hexane/ethyl acetate) to afford 0.13 g (51%) of benzyl 3-((2-bromo-3-(methoxycarbonyl)phenyl)amino)-5-oxo-5,6-dihydropyridine-1(2H)-carboxylate as a tan foam. ¹H NMR (CDCl$_3$-d1) δ 7.53-7.58 (m, 3H), 7.42-7.48 (m, 5H), 5.56 (s, 1H), 5.16 (s, 2H), 4.46 (s, 2H), 4.13 (s, 2H), 3.93 (s, 3H). MS (ESI) m/e [M+1]⁺ 459.0.

Step 2: 2-Benzyl 5-methyl 4-oxo-3,4-dihydro-1H-pyrido[3,4-b]indole-2,5(9H)-dicarboxylate

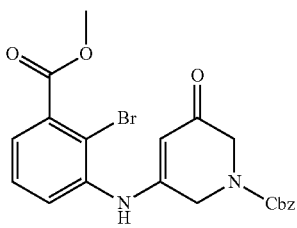 [SMILES: COC(=O)c1cccc(NC2=CC(=O)CN(C(=O)OCc3ccccc3)C2)c1Br]

A mixture of benzyl 3-((2-bromo-3-(methoxycarbonyl)phenyl)amino)-5-oxo-5,6-dihydropyridine-1(2H)-carboxylate (0.13 g, 0.28 mmol), palladium acetate (0.013 g, 0.06 mmol), tri-o-tolylphosphine (0.72 g, 0.19 mmol), and triethylamine (0.36 g, 0.36 mmol) in acetonitrile (2 mL) was heated in a sealed tubule flushed with nitrogen at 100° C. for 9 h. The cooled reaction mixture was diluted with DCM (3×50 mL) and water (10 mL). The organic layer was separated, washed with water, dried (Na$_2$SO$_4$), and concentrated. The remaining residue was chromatographed on silica gel, eluted with gradient 0-100% EtOAc in hexane to give the title compound (0.076 g, 72%). $^1$H NMR (CDCl$_3$-d1) δ 9.62 (s, 1H), 7.24-7.50 (m, 8H), 5.18 (s, 2H), 4.88 (s, 2H), 4.27 (s, 2H), 3.98 (s, 3H). MS (ESI) m/e [M+1]$^+$ 379.0.

Step 3: Benzyl 8-oxo-3,4,8,9-tetrahydro-2,4,9,10-tetraazacyclohepta[def]fluorene-2(1H)-carboxylate

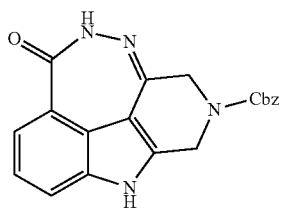 [SMILES: O=C1NN=C2CN(C(=O)OCc3ccccc3)Cc3[nH]c4cccc1c4c32]

A solution of compound 2-benzyl 5-methyl 4-oxo-3,4-dihydro-1H-pyrido[3,4-b]indole-2,5(9H)-dicarboxylate (70 mg, 0.18 mmol), acetic acid (0.15 mL, 2.6 mmol), and hydrazine hydrate (0.86 mL, 1.5 mmol) in methanol (4 mL) was heated at reflux. After 8 h, the solid was collected by hot filtration and washed with water, EtOAc, and dichloromethane, to give the target compound (61 mg, 94%). $^1$H NMR DMSO-d$_6$) δ 11.8 (s, 1H), 10.1 (s, 1H), 7.54 (d, 1H, J=8.4 Hz), 7.48 (d, 1H, J=7.2 Hz), 7.38 (m, 4H), 7.32 (m, 1H), 7.18 (dd, 1H, J=8.4, 7.2 Hz), 5.15 (s, 2H), 4.82 (m, 2H), 4.28 (m, 2H).MS (ESI) m/e [M+1]$^+$ 361.

Compound 21

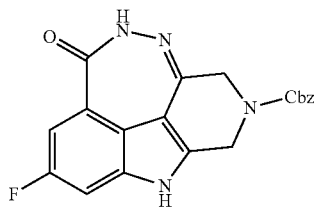 [SMILES: O=C1NN=C2CN(C(=O)OCc3ccccc3)Cc3[nH]c4cc(F)cc1c4c32]

Benzyl 6-fluoro-8-oxo-3,4,8,9-tetrahydro-2,4,9,10-tetraazacyclohepta[def]fluorene-2(1H)-carboxylate Compound 21 was prepared from methyl 2-bromo-5-fluoro-3-aminobenzoate and benzyl 3,5-dioxopiperidine-1-carboxylate according to the procedures for Compound 20 under appropriate conditions recognized by one of ordinary skill in the art. $^1$H NMR (DMSO-d6) δ 11.9 (s, 1H), 10.3 (s, 1H), 7.33-7.45 (m, 6H), 7.23 (dd, 1H, J=10.2, 1.8 Hz), 5.15 (s, 2H), 4.79-4.83 (m, 2H), 4.28-4.30 (m, 2H).MS (ESI) m/e [M+1]$^+$ 379.

Example 3: Synthesis of Compounds 22-25

Compound 22: 10-Methyl-2,3,5,10-tetrahydro-[1,2]diazepino[3,4,5,6-def]carbazol-6(1H)-one

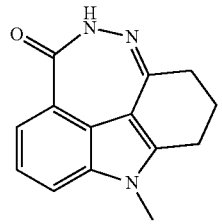 [SMILES: Cn1c2c3c4c(cccc41)C(=O)NN=C3CCC2]

Step 1: Methyl 9-methyl-4-oxo-2,3,4,9-tetrahydro-1H-carbazole-5-carboxylate

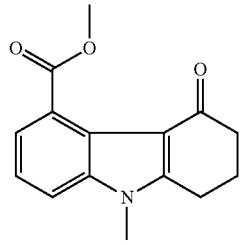 [SMILES: COC(=O)c1cccc2c1c1c(n2C)CCCC1=O]

To a solution of methyl 4-oxo-2,3,4,9-tetrahydro-1H-carbazole-5-carboxylate (0.27 g, 1 mmol) in THF (5 ml) at 0° C. under N$_2$ was added potassium t-butoxide (0.12 g, 1.05 mmol). The reaction mixture was stirred for 30 minutes followed by the addition of methyl iodide (0.76 g, 5.0 mmol). After 3 hours, the reaction mixture was concentrated to a residue and partitioned between EtOAc (40 ml) and 1N HCl (5 ml). The layers were shaken and separated. The organic layer was washed with 1N HCl (2×80 ml) and brine (2×10 ml), dried over Na$_2$SO$_4$, filtered, and concentrated to give a solid (0.46 g). The solid was used in the next step without further purified. $^1$H NMR (DMSO-d6) δ 7.35-7.39 (m, 2H), 7.29 (t, 1H, J=7.2 Hz), 4.01 (s, 3H), 3.72 (s, 3H), 2.93-2.95 (m, 2H), 2.54-2.56 (m, 2H), and 2.23-2.26 (m, 2H).MS (ESI) m/e [M+1]$^+$ 258.0

Step 2: 10-Methyl-2,3,5,10-tetrahydro-[1,2]diazepino [3,4,5,6-def]carbazol-6(1H)-one

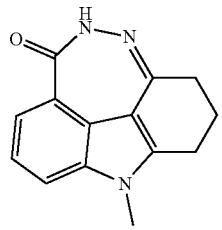 [SMILES: Cn1c2c3c4c(cccc41)C(=O)NN=C3CCC2]

The desired product was prepared using a procedure similar to step 3 for Compound 1. $^1$H NMR (DMSO-d6) 9.88 (s, 1H), 7.55 (d, 1H, J=7.8 Hz,), 7.45 (d, 1H, J=7.8 Hz,), 7.15 (t, 1H, J=7.8 Hz), 3.70 (s, 3H), 2.77-2.79 (m, 2H), 2.35-2.37 (m, 2H), and 1.92-1.93 (m, 2H). MS (ESI) m/e [M+1]⁺ 240.0

Compound 23: 2,2,10-trimethyl-2,3,5,10-tetrahydro-[1,2]diazepino[3,4,5,6-def]carbazol-6(1H)-one

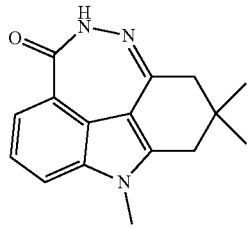 [SMILES: Cn1c2c3c4c(cccc41)C(=O)NN=C3CC(C)(C)C2]

Compound 23 was prepared from methyl 2,2-dimethyl-4-oxo-2,3,4,9-tetrahydro-1H-carbazole-5-carboxylate and methyl iodide according to the procedures for Compound 22 under appropriate conditions recognized by one of ordinary skill in the art. ¹H NMR (DMSO-d6) δ 9.86 (s, 1H), 7.42-7.53 (m, 2H), 7.12 (t, 1H, J=7.8 Hz), 3.66 (s, 3H), 2.67 (s, 2H), 2.20 (s, 2H), and 1.04 (s, 6H). MS (ESI) m/e [M+1]⁺ 268.

Compound 24: 10-Benzyl-2,3,5,10-tetrahydro-[1,2]diazepino[3,4,5,6-def]carbazol-6(1H)-one

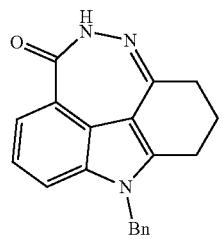 [SMILES: O=C1NN=C2CCCc3c2c2c1cccc2n3Cc1ccccc1]

Compound 24 was prepared from methyl 2,2-dimethyl-4-oxo-2,3,4,9-tetrahydro-1H-carbazole-5-carboxylate and benzyl chloride according to the procedures for Compound 22 under appropriate conditions recognized by one of ordinary skill in the art. ¹H NMR (DMSO-d6) δ 9.96 (s, 1H), 7.56 (d, 1H, J=8.4 Hz), 7.47 (d, 1H, J=7.8 Hz), 7.11-7.33 (m, 6H), 5.45 (s, 2H), 2.82-2.84 (m, 2H), 2.41-2.43 (m, 2H), and 1.97-2.00 (m, 2H). MS (ESI) m/e [M+1]⁺ 316.

Compound 25: 2,2,5,10-tetramethyl-2,3,5,10-tetrahydro-[1,2]diazepino[3,4,5,6-def]carbazol-6(1H)-one

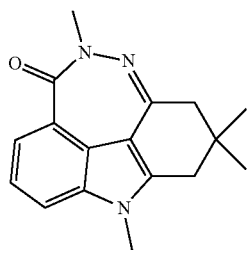 [SMILES: CN1N=C2CC(C)(C)Cc3c2c2c(cccc2n3C)C1=O]

The desired product was prepared using a procedure similar to step 1 of Example 22. Subsequently, 2,2-dimethyl-2,3,5,10-tetrahydro-[1,2]diazepino[3,4,5,6-def]carbazol-6(1H)-one (0.02 g, 0.08 mmol) was reacted with NaH (2.4 mg, 0.1 mmol) and methyl iodide (0.06 g, 0.4 mmol) in DMF (2 ml) to give the desired product (20 mg, 95%) as yellow solid. ¹H NMR (DMSO-d6) δ 7.51-7.55 (m, 2H), 7.16 (t, 1H, J=7.8 Hz), 3.69 (s, 3H), 3.42 (s, 3H), 2.72 (s, 2H), 2.27 (s, 2H), and 1.09 (s, 6H). MS (ESI) m/e [M+1]⁺ 282.

Example 4: Synthesis of Compound 26

Compound 26: 8-Fluoro-2,2-dimethyl-2,3-dihydro-[1,2]diazepino[3,4,5,6-def]carbazole-1,6(5H,10H)-dione

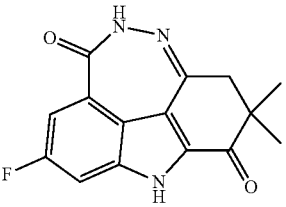 [SMILES: CC1(C)CC2=NNC(=O)c3cc(F)cc4[nH]c(c2c34)C1=O]

To a solution of carbamate 8-fluoro-2,2-dimethyl-2,3,5,10-tetrahydro-[1,2]diazepino[3,4,5,6-def]carbazol-6(1H)-one (0.5 g, 1.8 mmol) in anhydrous dioxane (25 mL) was added SeO₂ (0.32 g, 2.7 mmol). The mixture was refluxed for 40 h and filtered through Celite. The solid material was thoroughly washed with Et₂O. The filtrate was concentrated, and the residue was chromatographed to give product (200 mg, 38%) as a solid. ¹H NMR (DMSO-d6) δ 12.70 (s, 1H), 10.90 (s, 1H), 7.41 (dd, 1H, J=10.2, 1.8 Hz), 7.09 (dd, 1H, J=9.6, 1.8 Hz), 2.87 (s, 2H), 1.23 (s, 6H). MS (ESI) m/e [M+1]⁺ 286.

Example 5: Synthesis of Compound 27

Compound 27: 8-fluoro-1-hydroxy-2,2-dimethyl-2,3,5,10-tetrahydro-[1,2]diazepino[3,4,5,6-def]carbazol-6(1H)-one

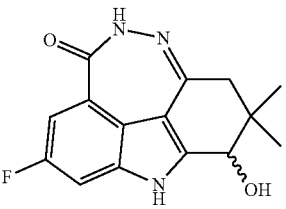 [SMILES: CC1(C)CC2=NNC(=O)c3cc(F)cc4[nH]c(c2c34)C1O]

To a solution of 8-fluoro-2,2-dimethyl-2,3-dihydro-[1,2]diazepino[3,4,5,6-def]carbazole-1,6(5H,10H)-dione (50 mg, 0.18 mmol) in 10 mL of MeOH, was added NaBH₄ (0.18 mmol) at 0° C. The mixture was stirred for additional 30 min. The solution was poured into ice water, and extracted with EtOAc (5 mL×3). The organic layers were combined, washed with H₂O (5 mL×3) and brine (5 mL×3), dried over Na₂SO₄, and filtered. The filtrate was concentrated, and the residue was chromatographed to give the crude product which was then purified on Pre-HPLC to give the product (5 mg) as a yellow solid. ¹H NMR (DMSO-d₆) δ 11.9 (s, 1H), 10.1 (s, 1H), 7.23 (dd, 1H, J=9.2, 2.0 Hz), 7.17 (dd, 1H, J=10.8, 2.4 Hz), 5.68 (d, 1H, J=6.0 Hz), 5.49 (d, 1H, J=6.0 Hz), 2.31 (s, 2H), 1.00 (s, 3H), and 0.88 (s, 3H). MS (ESI) m/e [M+1]⁺ 288.

Example 6: Synthesis of Compounds 28-39

Compound 28: 10-(2-(dimethylamino)ethyl)-2,2-dimethyl-2,3,5,10-tetrahydro-[1,2]diazepino[3,4,5,6-def]carbazol-6(1H)-one

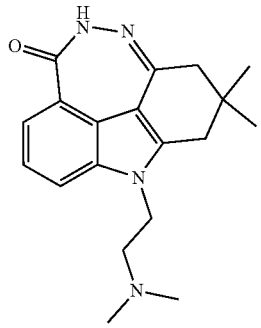 [SMILES: CN(C)CCn1c2c3c4c(cccc41)C(=O)NN=C3CC(C)(C)C2]

To a cooled solution (0° C.) of 2,2-dimethyl-2,3,5,10-tetrahydro-[1,2]diazepino[3,4,5,6-def]carbazol-6(1H)-one (94 mg, 0.37 mmol) and DMF (10 mL) was added slowly K₂CO₃ (205 mg, 1.48 mmol), then N,N-dimethylamino-2-chloroethane (53 mg, 0.37 mmol) was added. The resulting solution was stirred at 70° C. for 4h. The solution was allowed to cool and water was added (10 mL). The mixture was extracted with ethyl acetate (2×20 mL). The organic layers were combined, dried over Na₂SO₄, and filtered. The filtrate was concentrated, and the residue was chromatographed to give the product (90 mg, 75%) as a yellow solid. ¹H NMR (DMSO-d6) δ 9.91 (s, 1H), 7.58 (d, 1H, J=7.8 Hz), 7.47 (d, 1H, J=7.8 Hz), 7.16 (t, 1H, J=7.8 Hz), 4.23 (m, 2H), 2.74 (s, 2H), 2.51 (m, 2H), 2.25 (s, 2H), 2.18 (s, 6H), and 1.07 (s, 6H). MS (ESI) m/e [M+1]⁺ 325.

Compounds 29-39 were synthesized according to the procedures for Compound 28 by using the corresponding starting material under appropriate conditions recognized by one of ordinary skill in the art.

| Compound No. | Name | 1H-NMR data LC/MS m/z (M + 1) | Structure |
| --- | --- | --- | --- |
| 29 | 10-(2-(dibenzylamino)ethyl)-2,2-dimethyl-2,3,5,10-tetrahydro-[1,2]diazepino[3,4,5,6-def]carbazol-6(1H)-one | (DMSO-d₆) δ 9.87 (s, 1H), 7.40 (d, 1H, J = 7.2 Hz), 7.31 (d, 1H, J = 7.6 Hz), 7.13-7.22 (m, 10 H), 7.00 (dd, 1H, J = 7.2, 7.6 Hz), 4.15-4.18 (m, 2H), 3.61 (br s, 4H), 2.56-2.59 (m, 2H), 2.24 (s, 2H), 2.11 (s, 2H), and 0.87 (s, 6H). MS (ESI) m/e [M + 1]⁺ 477.0. | 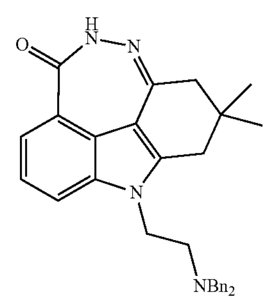 |
| 30 | 2,2-dimethyl-10-(2-(pyrrolidin-1-yl)ethyl)-2,3,5,10-tetrahydro-[1,2]diazepino[3,4,5,6-def]carbazol-6(1H)-one | (DMSO-d₆) δ 9.91 (s, 1H), 7.58 (d, 1H, J = 7.8 Hz), 7.47 (d, 1H, J = 7.2 Hz), 7.17 (dd, 1H, J = 7.2, 7.8 Hz), 4.23-4.26 (m, 2H), 2.69-2.74 (m, 4H), 2.45 (br s, 4H), 2.25 (br s, 2H), 1.64-1.65 (m, 4H), and 1.07 (s, 6H). MS (ESI) m/e [M + 1]⁺ 351.0. | 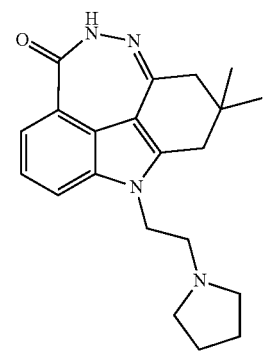 [SMILES: CC1(C)CC2=NNC(=O)c3cccc4c3c2c(n4CCN2CCCC2)C1] |

| Compound No. | Name | 1H-NMR data LC/MS m/z (M + 1) | Structure |
|---|---|---|---|
| 31 | 2,2-dimethyl-10-(2-(piperidin-1-yl)ethyl)-2,3,5,10-tetrahydro-[1,2]diazepino[3,4,5,6-def]carbazol-6(1H)-one | (DMSO-d$_6$) δ 9.89 (s, 1H), 7.57 (d, 1H, J = 8.4 Hz), 7.47 (d, 1H, J = 7.8 Hz), 7.17 (dd, 1H, J = 8.4, 7.8 Hz), 4.20-4.22 (m, 2H), 2.89 (br s, 2H), 2.50 (br s, 2H), 2.35 (br s, 4H), 2.25 (br s, 2H), 1.35-1.46 (m, 6H), and 1.07 (s, 6H). MS (ESI) m/e [M + 1]$^+$ 365.0. | 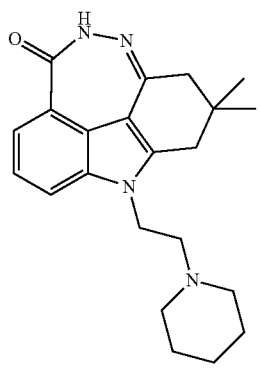 [SMILES: CC1(C)CC2=NNC(=O)c3cccc4c3c2c(n4CCN2CCCCC2)C1] |
| 32 | 2,2-dimethyl-10-(2-morpholinoethyl)-2,3,5,10-tetrahydro-[1,2]diazepino[3,4,5,6-def]carbazol-6(1H)-one | (DMSO-d$_6$) δ 9.91 (s, 1H), 7.59 (d, 1H, J = 8.4 Hz), 7.47 (d, 1H, J = 7.8 Hz), 7.16 (dd, 1H, J = 8.4, 7.8 Hz), 4.24-4.26 (m, 2H), 3.53-3.54 (m, 4H), 2.77 (br s, 2H), 2.57-2.59 (m, 2H), 2.42 (br s, 4H), 2.25 (br s, 2H), and 1.08 (s, 6H). MS (ESI) m/e [M + 1]$^+$ 367.0. | 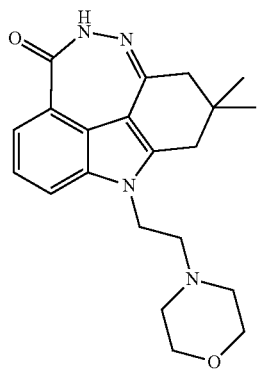 [SMILES: CC1(C)CC2=NNC(=O)c3cccc4c3c2c(n4CCN2CCOCC2)C1] |
| 33 | 10-(2-(diethylamino)ethyl)-2,2-dimethyl-2,3,5,10-tetrahydro-[1,2]diazepino[3,4,5,6-def]carbazol-6(1H)-one | (DMSO-d$_6$) δ 9.89 (s, 1H), 7.56 (d, 1H, J = 7.8 Hz), 7.46 (d, 1H, J = 7.8 Hz), 7.15 (t, 1H, J = 7.8 Hz), 4.15-4.17 (m, 2H), 2.76 (s, 2H), 2.62-2.64 (m, 2H), 2.43-2.46 (m, 4H), 2.25 (s, 2H), 1.07 (s, 6H), and 0.81 (t, 6H, J = 7.2 Hz). MS (ESI) m/e [M + 1]$^+$ 353.0. | 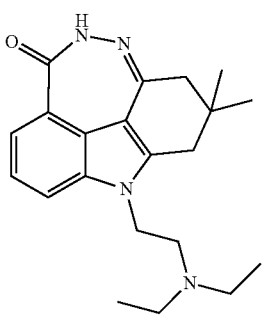 [SMILES: CCN(CC)CCn1c2c3c4c(cccc41)C(=O)NN=C3CC(C)(C)C2] |
| 34 | 10-(2-(pyrrolidin-1-yl)ethyl)-2,3,5,10-tetrahydro-[1,2]diazepino[3,4,5,6-def]carbazol-6(1H)-one | (DMSO-d$_6$) δ 9.91 (s, 1H), 7.57 (d, 1H, J = 7.8 Hz), 7.46 (d, 1H, J = 7.8 Hz), 7.16 (t, 1H, J = 7.8 Hz), 4.25-4.27 (m, 2H), 2.87-2.89 (m, 2H), 2.72 (br s, 2H), 2.41-2.47 (m, 6H), 1.98-2.00 (m, 2H), and 1.66 (br s, 4H). MS (ESI) m/e [M + 1]$^+$ 323.0. | 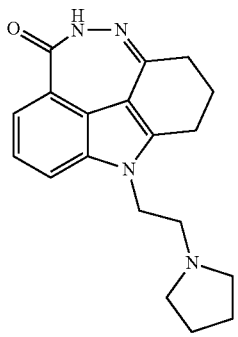 [SMILES: O=C1NN=C2CCCc3c2c2c1cccc2n3CCN1CCCC1] |

-continued

| Compound No. | Name | 1H-NMR data LC/MS m/z (M + 1) | Structure |
|---|---|---|---|
| 35 | 10-(2-(piperidin-1-yl)ethyl)-2,3,5,10-tetrahydro-[1,2]diazepino[3,4,5,6-def]carbazol-6(1H)-one | (DMSO-$d_6$) δ 9.89 (s, 1H), 7.57 (d, 1H, J = 7.8 Hz), 7.46 (d, 1H, J = 7.8 Hz), 7.16 (t, 1H, J = 7.8 Hz), 4.23-4.25 (m, 2H), 2.89-2.91 (m, 2H), 2.51-2.55 (m, 2H), 2.36-2.43 (m, 6H), 1.98-2.00 (m, 2H), and 1.36-1.45 (m, 6H). MS (ESI) m/e [M + 1]$^+$ 337.0. | 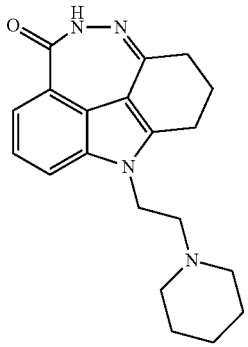 [SMILES: O=C1NN=C2CCCc3c2c2c1cccc2n3CCN1CCCCC1] |
| 36 | 10-(2-morpholinoethyl)-2,3,5,10-tetrahydro-[1,2]diazepino[3,4,5,6-def]carbazol-6(1H)-one. | (DMSO-$d_6$) δ 9.90 (s, 1H), 7.59 (d, 1H, J = 7.8 Hz), 7.47 (d, 1H, J = 7.8 Hz), 7.16 (t, 1H, J = 7.8 Hz), 4.25-4.27 (m, 2H), 3.52-3.54 (m, 4H), 2.89-2.91 (m, 2H), 2.58-2.60 (m, 2H), 2.41-2.43 (m, 6H), and 1.99-2.01 (m, 2H). MS (ESI) m/e [M + 1]$^+$ 339.0. | 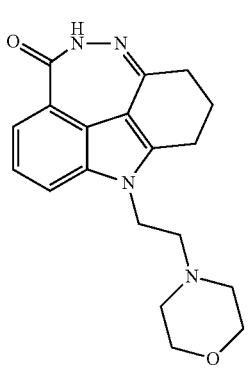 [SMILES: O=C1NN=C2CCCc3c2c2c1cccc2n3CCN1CCOCC1] |
| 37 | 10-(2-(dimethylamino)ethyl)-2,3,5,10-tetrahydro-[1,2]diazepino[3,4,5,6-def]carbazol-6(1H)-one | (DMSO-$d_6$) δ 9.91 (s, 1H), 7.58 (d, 1H, J = 8.4 Hz), 7.47 (d, 1H, J = 7.8 Hz), 7.16 (dd, 1H, J = 8.4, 7.8 Hz), 4.22-4.25 (m, 2H), 2.88-2.90 (m, 2H), 2.41-2.47 (m, 4H), 2.19 (s, 6H), and 1.92-2.00 (m, 2H). MS: (ESI) m/e [M + 1]$^+$ 297.0. | 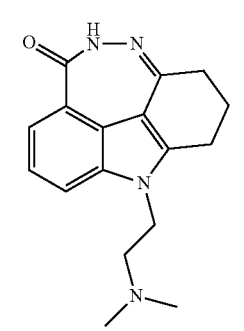 [SMILES: CN(C)CCn1c2c3c4c(cccc41)C(=O)NN=C3CCC2] |
| 38 | 10-(2-(diethylamino)ethyl)-2,3,5,10-tetrahydro-[1,2]diazepino[3,4,5,6-def]carbazol-6(1H)-one | (DMSO-$d_6$) δ 9.88 (s, 1H), 7.56 (d, 1H, J = 7.2 Hz), 7.45 (d, 1H, J = 7.2 Hz), 7.15 (t, 1H, J = 7.2 Hz), 4.16-4.18 (m, 2H), 2.89-2.91 (m, 2H), 2.63-2.65 (m, 2H), 2.40-2.45 (m, 6H), 1.98-2.00 (m, 2H), and 0.82 (t, 6H, J = 7.2 Hz). MS (ESI) m/e [M + 1]$^+$ 325.0. | 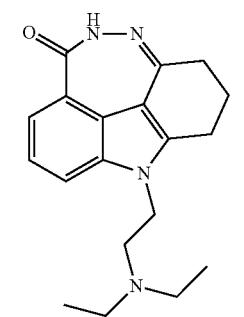 [SMILES: CCN(CC)CCn1c2c3c4c(cccc41)C(=O)NN=C3CCC2] |

| Compound No. | Name | 1H-NMR data LC/MS m/z (M + 1) | Structure |
|---|---|---|---|
| 39 | 10-(2-(dibenzylamino)ethyl)-2,3,5,10-tetrahydro-[1,2]diazepino[3,4,5,6-def]carbazol-6(1H)-one | (DMSO-d₆) δ 9.87 (s, 1H), 7.40 (d, 1H, J = 7.6 Hz), 7.29 (d, 1H, J = 8.4 Hz), 7.06-.19 (m, 10 H), 6.98 (dd, 1H, J = 8.4, 7.6 Hz), 4.18-4.21 (m, 2H), 3.54-3.58 (d, 4H, J = 8.8 Hz), 2.61-2.64 (m, 2H), 2.45-2.47 (m, 2H), 2.27-2.31 (m, 2H), and 1.78-1.81 (m, 2H). MS (ESI) m/e [M + 1]⁺ 449.0. | 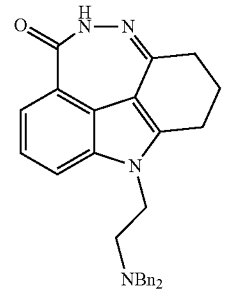 |

Example 7: Synthesis of Compound 40

Compound 40: 10-(2-(dimethylamino)ethyl)-8-fluoro-2,2-dimethyl-2,3,5,10-tetrahydro-[1,2]diazepino[3,4,5,6-def]carbazol-6(1H)-one

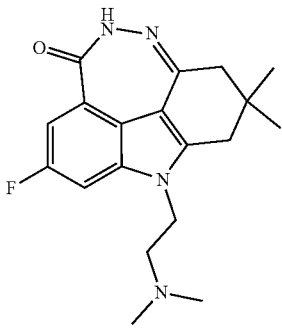 [SMILES: CN(C)CCn1c2c3c4c(cc(F)cc41)C(=O)NN=C3CC(C)(C)C2]

Compound 40 was prepared from 8-fluoro-2,2-dimethyl-2,3,5,10-tetrahydro-[1,2]diazepino[3,4,5,6-def]carbazol-6(1H)-one and N,N-dimethylamino-2-chloroethane according to the procedures similar to those for Compound 28. ¹H NMR (DMSO-d6) δ 10.1 (s, 1H), 7.56 (dd, 1H, J=9.6, 1.8 Hz), 7.21 (dd, 1H, J=10.2, 1.8 Hz), 4.22 (m, 2H), 2.74 (s, 2H), 2.51 (m, 2H), 2.26 (s, 2H), 2.17 (s, 6H), and 1.06 (s, 6H). MS (ESI) m/e [M+1]⁺ 343.

Example 8: Synthesis of Compound 41

Compound 41: 2,2-dimethyl-10-(oxiran-2-ylmethyl)-2,3,5,10-tetrahydro-[1,2]diazepino[3,4,5,6-def]carbazol-6(1H)-one

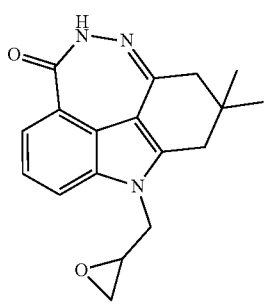 [SMILES: CC1(C)CC2=NNC(=O)c3cccc4c3c2c(n4CC2CO2)C1]

Compound 41 was prepared from 2,2-dimethyl-2,3,5,10-tetrahydro-[1,2]diazepino[3,4,5,6-def]carbazol-6(1H)-one and 2-(chloromethyl)oxirane according to the procedures similar to those for Compound 28. ¹H NMR (DMSO-d6) δ 9.96 (s, 1H), 7.65 (d, 1H, J=8.4 Hz), 7.49 (d, 1H, J=7.8 Hz), 7.18 (dd, 1H, J=8.4, 7.8 Hz), 4.60-4.63 (m, 1H), 4.21-4.24 (m, 1H), 3.27-3.29 (m, 1H), 2.76-2.77 (m, 1H), 2.75 (s, 2H), 2.46-2.48 (m, 1H), 2.26 (s, 2H), and 0.92 (s, 6H). MS (ESI) m/e [M+1]⁺ 310.

Example 9: Synthesis of Compound 42

Compound 42: 2,3,4,9-Tetrahydro-2,4,9,10-tetraazacyclohepta[def]fluoren-8(1H)-one

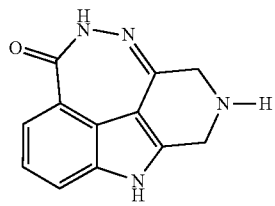 [SMILES: O=C1NN=C2CNCc3[nH]c4cccc1c4c32]

A mixture of Compound 20 (34 mg, 0.1 mmol) and palladium (10%) on carbon (10 mg) in 10 mL of methanol was stirred at RT under a balloon of hydrogen for 5 h. The mixture was then filtered through a pad of celite. The catalyst cake was washed with methanol. The filtrate was concentrated. The resulting residue was purified by HPLC to give the target product as formic acid salt (white solid) (13 mg, 50%). ¹H NMR (DMSO-d6) δ 11.7 (s, 1H), 9.86 (s, 1H), 7.40-7.45 (m, 2H), 7.09 (t, 1H, J=8.0 Hz), 3.94 (s, 2H), 3.41 (s, 2H).MS (ESI) m/e [M+1]⁺ 227.

Example 10: Synthesis of Compound 43

Compound 43: 6-Fluoro-2,3,4,9-tetrahydro-2,4,9,10-tetraazacyclohepta[def]fluoren-8(1H)-one

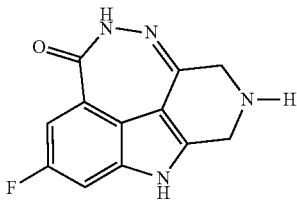 [SMILES: O=C1NN=C2CNCc3[nH]c4cc(F)cc1c4c32]

Compound 43 was prepared from Compound 21 and palladium (10%) on carbon according to the procedures similar to those for Compound 42. $^1$H NMR (DMSO-d6) δ 11.8 (s, 1H), 10.04 (s, 1H), 7.29 (dd, 1H, J=10.0, 1.6 Hz), 7.11 (dd, 1H, J=10.4, 1.6 Hz), 3.93 (s, 2H), 3.45 (s, 2H). MS (ESI) m/e [M+1]$^+$ 245.

Example 11: Synthesis of Compound 44

Compound 44: 2-Methyl-2,3,4,9-tetrahydro-2,4,9,10-tetraazacyclohepta[def]fluoren-8(1H)-one

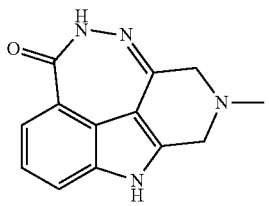 [SMILES: CN1CC2=NNC(=O)c3cccc4[nH]c(c2c34)C1]

Step 1: Methyl 2-methyl-4-oxo-2,3,4,9-tetrahydro-1H-pyrido[3,4-b]indole-5-carboxylate

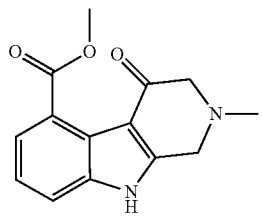 [SMILES: COC(=O)c1cccc2[nH]c3c(c12)C(=O)CN(C)C3]

Methyl 4-oxo-2,3,4,9-tetrahydro-1H-pyrido[3,4-b]indole-5-carboxylate (0.04 g, 0.016 mmol) and NaCNBH$_3$ (2.4 mg, 0.04 mmol) were added to a round bottomed flask, which were then dissolved in MeOH (2 mL), and treated with 0.5 mL of a 27% solution of formaldehyde in water. This mixture was stirred for 2 h, after which, 2N HCl (2 mL) was added, followed by stirring for 15 min. The mixture was taken to pH=11 by addition of concentrated, aqueous NaOH and extracted with methylene chloride (3×10 mL). The combined organic layers were washed with brine, dried (Na$_2$SO$_4$), and concentrated. The crude product was used in the next step without further purification.

Step 2: 2-Methyl-2,3,49-tetrahydro-2,4,9,10-tetraazacyclohepta[def]fluoren-8(1H)-one

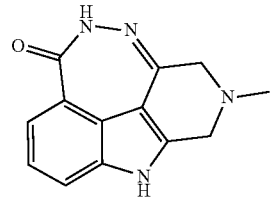 [SMILES: CN1CC2=NNC(=O)c3cccc4[nH]c(c2c34)C1]

Compound 44 was prepared from Methyl 2-methyl-4-oxo-2,3,4,9-tetrahydro-1H-pyrido[3,4-b]indole-5-carboxylate and hydrazine hydrate according to the procedure similar to that for Compound 1. $^1$H NMR (DMSO-d6) δ 11.7 (s, 1H), 9.87 (s, 1H), 7.43 (d, 1H, J=8.0 Hz), 7.39 (d, 1H, J=7.6 Hz), 7.14 (dd, 1H, J=8.0, 7.6 Hz), 3.70 (s, 2H), 3.13 (s, 2H), and 2.39 (s, 3H). MS (ESI) m/e [M+1]$^+$ 241.

Example 12: Synthesis of Compound 45

Compound 45: 2-Isopropyl-2,3,4,9-tetrahydro-2,4,9,10-tetraazacyclohepta[def]fluoren-8(1H)-one

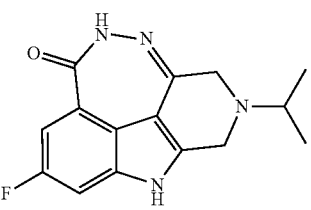 [SMILES: CC(C)N1CC2=NNC(=O)c3cc(F)cc4[nH]c(c2c34)C1]

Compound 45 was prepared from methyl 4-oxo-2,3,4,9-tetrahydro-H-pyrido[3,4-b]indole-5-carboxylate and acetone according to the procedures similar to those for Compound 44. $^1$H NMR (DMSO-d6) δ 11.7 (s, 1H), 9.83 (s, 1H), 7.43 (d, 1H, J=8.4 Hz), 7.38 (d, 1H, J=7.6 Hz), 7.08 (dd, 1H, J=8.4, 7.6 Hz), 3.78 (s, 2H), 3.26 (s, 2H), 2.93-2.96 (m, 1H), 1.04 (d, 6H, J=6.4 Hz). MS (ESI) m/e [M+1]$^+$ 269.

Example 13: Synthesis of Compound 46

Compound 46: 6-Fluoro-2-isopropyl-2,3,4,9-tetrahydro-2,4,9,10-tetraazacyclohepta[def]fluoren-8(1H)-one

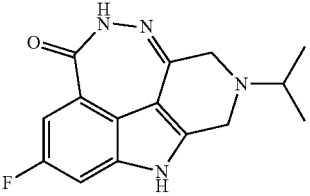 [SMILES: CC(C)N1CC2=NNC(=O)c3cc(F)cc4[nH]c(c2c34)C1]

Compound 46 was prepared from methyl 7-fluoro-4-oxo-2,3,4,9-tetrahydro-1H-pyrido[3,4-b]indole-5-carboxylate and acetone according to the procedures similar to those for Compound 44. $^1$H NMR (DMSO-d6) δ 11.8 (s, 1H), 10.1 (s, 1H), 7.35 (dd, 1H, J=2.4, 9.6 Hz), 7.18 (dd, 1H, J=2.4, 10.2

Hz), 3.82 (s, 2H), 3.32 (s, 2H), 2.98-3.00 (m, 1H), 1.09 (d, 6H, J=7.2 Hz). MS (ESI) m/e [M+1]+ 287.

Example 14: Synthesis of Compound 47

Compound 47: 2-(cyclopropanecarbonyl)-2,3,4,9-tetrahydro-2,4,9,10-tetraazacyclohepta[def]fluoren-8(1H)-one

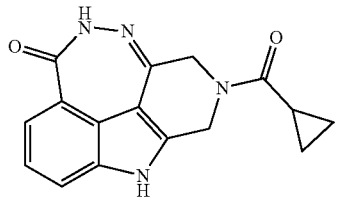 [SMILES: O=C1NN=C2CN(C(=O)C3CC3)Cc3[nH]c4cccc1c4c32]

Step 1: Methyl 2-(cyclopropanecarbonyl)-4-oxo-2,3,4,9-tetrahydro-H-pyrido[3,4-b]indole-5-carboxylate

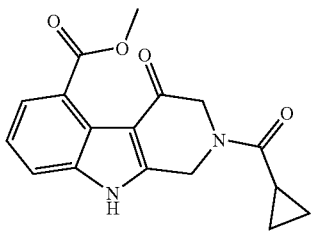 [SMILES: COC(=O)c1cccc2[nH]c3c(c12)C(=O)CN(C(=O)C1CC1)C3]

To a solution of methyl 4-oxo-2,3,4,9-tetrahydro-1H-pyrido[3,4-b]indole-5-carboxylate (0.21 g, 0.82 mmol) and cyclopropanecarbonyl chloride (0.074 mL, 0.82 mmol) in CH$_2$Cl$_2$ (10 mL) was added DIPEA (0.143 mL) at 0° C., and the mixture was stirred at −5° C. for 1.0 h. Then the solvent was evaporated to give the crude product, which was purified by Pre-TLC to give the title compound (170 mg). MS (ESI) m/e [M+1]+ 313.

Step 2: 2-(cyclopropanecarbonyl)-2,3,4,9-tetrahydro-2,4,9,10-tetraazacyclohepta[def]fluoren-8(1H)-one Compound 47 was prepared from methyl 2-(cyclopropanecarbonyl)-4-oxo-2,3,4,9-tetrahydro-1H-pyrido[3,4-b]indole-5-carboxylate and hydrazine hydrate according to the procedure similar to that for Compound 1. $^1$H NMR (DMSO-d6) δ 11.9 (s, 1H), 10.0 (s, 1H), 7.47-7.53 (m, 2H), 7.17 (dd, 1H, J=7.2, 7.8 Hz), 4.89 (s, 2H), 4.35 (s, 2H), 2.08-2.11 (m, 1H), and 0.78-0.79 (m, 4H). MS (ESI) m/e [M+1]+ 295.

Example 15: Synthesis of Compound 48

Compound 48: 2-(cyclopropanecarbonyl)-4-(2-(dimethylamino)ethyl)-2,3,4,9-tetrahydro-2,4,9,10-tetraazacyclohepta[def]fluoren-8(1H)-one

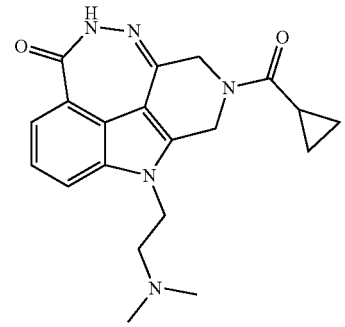 [SMILES: CN(C)CCn1c2c3c4c(cccc41)C(=O)NN=C3CN(C(=O)C1CC1)C2]

Compound 48 was prepared from 2-(cyclopropanecarbonyl)-2,3,4,9-tetrahydro-2,4,9,10-tetraazacyclohepta[def]fluoren-8(1H)-one and N,N-dimethylamino-2-chloroethane according to the procedures similar to those for Compound 28. $^1$H NMR (DMSO-d6) δ 10.0 (s, 1H), 7.67 (d, 1H, J=8.4 Hz), 7.51 (d, 1H, J=7.8 Hz), 7.23 (dd, 1H, J=8.4, 7.8 Hz), 5.22 (s, 1H), 4.98 (s, 1H), 4.55 (s, 1H), 4.28-4.35 (m, 3H), 2.58-2.62 (m, 2H), 2.19 (s, 6H), 2.09-2.13 (m, 1H), and 0.79 (s, 4H). MS (ESI) m/e [M+1]+ 366.

Example 16: Synthesis of Compound 49

Compound 49: 2-(cyclopropanecarbonyl)-6-fluoro-2,3,4,9-tetrahydro-2,4,9,10-tetraazacyclohepta[def]fluoren-8(1H)-one

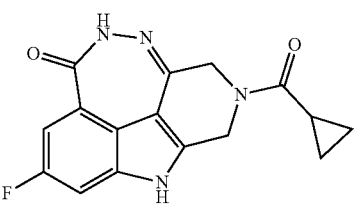 [SMILES: O=C1NN=C2CN(C(=O)C3CC3)Cc3[nH]c4cc(F)cc1c4c32]

Compound 49 was prepared from methyl 7-fluoro-4-oxo-2,3,4,9-tetrahydro-1H-pyrido[3,4-b]indole-5-carboxylate and cyclopropanecarbonyl chloride according to the procedures similar to those for Compound 47. $^1$H NMR (DMSO-d6) δ 9.64 (s, 1H), 6.80-7.08 (m, 2H), 4.95 (s, 1H), 4.74 (s, 1H), 4.40 (s, 1H), 4.20 (s, 1H), 2.03-2.07 (m, 1H), and 0.75 (s, 4H). MS (ESI) m/e [M+1]+ 313.

Example 17: Synthesis of Compound 50

Compound 50: 2-(Cyclopropanecarbonyl)-4-(2-(dimethylamino)ethyl)-6-fluoro-2,3,4,9-tetrahydro-2,4,9,10-tetraazacyclohepta[def]fluoren-8(1H)-one

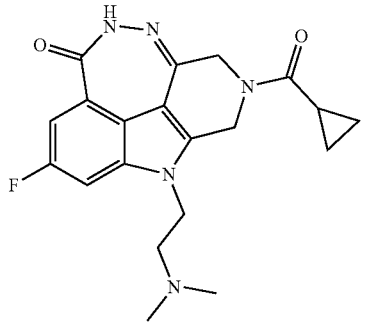 [SMILES: CN(C)CCn1c2c3c4c(cc(F)cc41)C(=O)NN=C3CN(C(=O)C1CC1)C2]

Compound 50 was prepared from 2-(cyclopropanecarbonyl)-6-fluoro-2,3,4,9-tetrahydro-2,4,9,10-tetraazacyclohepta[def]fluoren-8(1H)-one and N,N-dimethylamino-2-chloroethane according to the procedures similar to those for Compound 28. $^1$H NMR (DMSO-d6) δ 10.0 (s, 1H), 7.66 (dd, 1H, J=2.4, 9.6 Hz), 7.26 (dd, 1H, J=2.4, 10.2 Hz), 5.21 (s, 1H), 4.96 (s, 1H), 4.55 (s, 1H), 4.27-4.36 (m, 3H), 2.56-2.59 (m, 2H), 2.18 (s, 6H), 2.11-2.13 (m, 1H), and 0.79 (s, 4H). MS (ESI) m/e [M+1]$^+$ 384.

Example 18: Synthesis of Compound 51

Compound 51: 2-Pivaloyl-2,3,4,9-tetrahydro-2,4,9,10-tetraazacyclohepta[def]fluoren-8(1H)-one

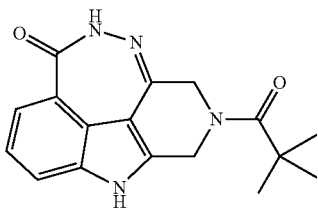 [SMILES: CC(C)(C)C(=O)N1CC2=NNC(=O)c3cccc4[nH]c(c2c34)C1]

Compound 51 was prepared from methyl 4-oxo-2,3,4,9-tetrahydro-1H-pyrido[3,4-b]indole-5-carboxylate and pivaloyl chloride according to the procedures similar to those for Compound 47. $^1$H NMR (DMSO-d6) δ 9.63 (s, 1H), 7.27-7.47 (m, 2H), 6.96 (s, 1H), 4.89 (s, 2H), 4.33 (s, 2H), and 1.24 (s, 9H). MS (ESI) m/e [M+1]$^+$ 311.

Example 19: Synthesis of Compound 52

Compound 52: 6-Fluoro-2-pivaloyl-2,3,4,9-tetrahydro-2,4,9,10-tetraazacyclohepta[def]fluoren-8(1H)-one

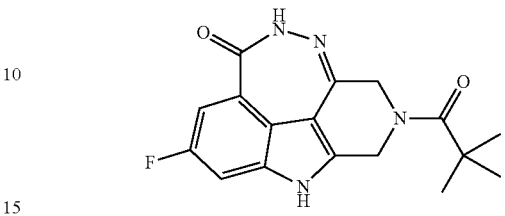

Compound 52 was prepared from methyl 7-fluoro-4-oxo-2,3,4,9-tetrahydro-1H-pyrido[3,4-b]indole-5-carboxylate and pivaloyl chloride according to the procedures similar to those for Compound 47. $^1$H NMR (DMSO-d6) δ 11.9 (s, 1H), 10.2 (s, 1H), 7.45 (dd, 1H, J=2.4, 9.6 Hz), 7.22 (dd, 1H, J=2.4, 10.2 Hz), 4.92 (s, 2H), 4.42 (s, 2H), and 1.24 (s, 9H). MS (ESI) m/e [M+1]$^+$329.

Example 20: Synthesis of Compound 53

Compound 53: 2-Cyclohexyl-2,3,4,9-tetrahydro-2,4,9,10-tetraazacyclohepta[def]fluoren-8(1H)-one

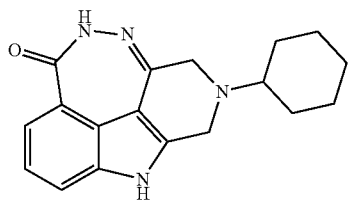 [SMILES: O=C1NN=C2CN(C3CCCCC3)Cc3[nH]c4cccc1c4c32]

Compound 53 was prepared from methyl 4-oxo-2,3,4,9-tetrahydro-1H-pyrido[3,4-b]indole-5-carboxylate and cyclohexanone according to the procedures similar to those for Compound 44. $^1$H NMR (DMSO-d6) δ 11.7 (s, 1H), 9.86 (s, 1H), 7.47 (d, 1H, J=7.8 Hz), 7.42 (d, 1H, J=7.8 Hz), 7.12 (t, 1H, J=7.8 Hz), 3.91 (s, 2H), 3.38 (s, 2H), 2.50-2.56 (m, 1H), 1.58-1.84 (m, 4H), and 1.11-1.31 (m, 6H). MS (ESI) m/e [M+1]$^+$ 309.

Example 21: Synthesis of Compound 54

Compound 54: 2-(3,3-dimethylbutyl)-2,3,4,9-tetrahydro-2,4,9,10-tetraazayclohepta[def]fluoren-8(1H)-one

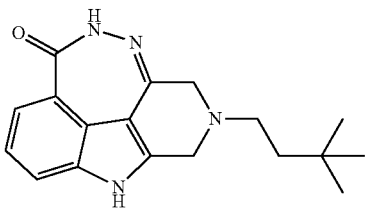 [SMILES: CC(C)(C)CCN1CC2=NNC(=O)c3cccc4[nH]c(c2c34)C1]

Compound 54 was prepared from 2,3,4,9-tetrahydro-2,4,9,10-tetraazacyclohepta[def]fluoren-8(1H)-one and 3,3-dimethylbutanal according to the procedures similar to those for Compound 44. ¹H NMR (DMSO-d6) δ 11.9 (s, 1H), 9.89 (s, 1H), 7.48 (d, 1H, J=7.8 Hz), 7.43 (d, 1H, J=7.2 Hz), 7.13 (dd, 1H, J=7.2, 7.8 Hz), 3.81 (br s, 2H), 3.29 (br s, 2H), 2.57-2.58 (m, 2H), 1.43-1.46 (m, 2H), and 0.91 (s, 9H). MS (ESI) m/e [M+1]⁺ 311.

Example 22: Synthesis of Compound 55

Compound 55: 6-Fluoro-2-methyl-2,3,4,9-tetrahydro-2,4,9,10-tetraazacyclohepta[def]fluoren-8(1H)-one

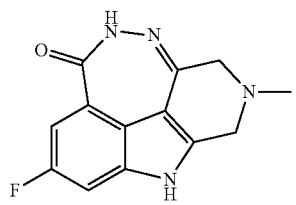 [SMILES: CN1CC2=NNC(=O)c3cc(F)cc4[nH]c(c2c34)C1]

Compound 55 was prepared from methyl 2-bromo-5-fluoro-3-aminobenzoate and benzyl 3,5-dioxopiperidine-1-carboxylate according to the procedures similar to those for Compound 44. ¹H NMR (DMSO-d6) δ 11.9 (s, 1H), 10.1 (s, 1H), 7.36 (dd, 1H, J=1.8, 9.6 Hz), 7.20 (dd, 1H, J=1.8, 10.2 Hz), 3.75 (s, 2H), 3.24 (s, 2H), 2.44 (s, 3H). MS (ESI) m/e [M+1]⁺ 259.

Example 23: Synthesis of Compound 56

Compound 56: 2-Propyl-2,3,4,9-tetrahydro-2,4,9,10-tetraazacyclohepta[def]fluoren-8(1H)-one

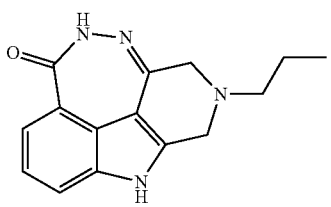 [SMILES: CCCN1CC2=NNC(=O)c3cccc4[nH]c(c2c34)C1]

Compound 56 was prepared from methyl 4-oxo-2,3,4,9-tetrahydro-1H-pyrido[3,4-b]indole-5-carboxylate and propionaldehyde according to the procedures similar to those for Compound 44. ¹H NMR (DMSO-d6) δ 11.7 (s, 1H), 9.92 (s, 1H), 7.47 (d, 1H, J=7.8 Hz), 7.43 (d, 1H, J=7.8 Hz), 7.13 (t, 1H, J=7.8 Hz), 3.81 (s, 2H), 3.28 (s, 2H), 2.50-2.55 (m, 2H), 1.51-1.54 (m, 2H), and 0.89 (t, 3H, J=7.8 Hz). MS (ESI) m/e [M+1]⁺ 269.

Example 24: Synthesis of Compound 57

Compound 57: 6-Fluoro-2-propyl-2,3,4,9-tetrahydro-2,4,9,10-tetraazacyclohepta[def]fluoren-8(1H)-one

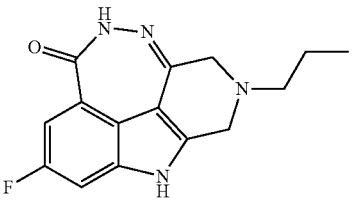 [SMILES: CCCN1CC2=NNC(=O)c3cc(F)cc4[nH]c(c2c34)C1]

Compound 57 was prepared from methyl 2-bromo-5-fluoro-3-aminobenzoate and benzyl 3,5-dioxopiperidine-1-carboxylate according to the procedures similar to those for Compound 44. ¹H NMR (DMSO-d6) δ 11.8 (s, 1H), 10.1 (s, 1H), 7.36 (dd, 1H, J=1.8, 9.0 Hz), 7.19 (dd, 1H, J=1.8, 10.2 Hz), 3.80 (s, 2H), 3.30 (s, 2H), 2.50-2.54 (m, 2H), 1.50-1.54 (m, 2H), and 0.89 (t, 3H, J=7.8 Hz). MS (ESI) m/e [M+1]⁺ 287.

Example 25: Synthesis of Compound 58

Compound 58: 2-Ethyl-6-fluoro-2,3,4,9-tetrahydro-2,4,9,10-tetraazacyclohepta[def]fluoren-8(1H)-one

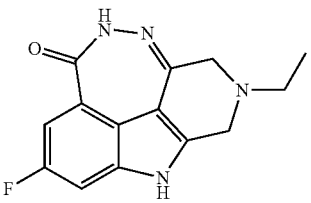 [SMILES: CCN1CC2=NNC(=O)c3cc(F)cc4[nH]c(c2c34)C1]

Compound 58 was prepared from methyl 2-bromo-5-fluoro-3-aminobenzoate and benzyl 3,5-dioxopiperidine-1-carboxylate according to the procedures similar to those for Compound 44. ¹H NMR (DMSO-d₆) δ 11.8 (s, 1H), 10.1 (s, 1H), 7.35 (dd, 1H, J=2.4, 9.6 Hz), 7.19 (dd, 1H, J=2.4, 10.2 Hz), 3.80 (s, 2H), 3.30 (s, 2H), 2.60-2.64 (m, 2H), and 1.09 (t, 3H, J=7.2 Hz). MS (ESI) m/e [M+1]⁺ 273.

Example 26: Synthesis of Compound 59

Compound 59: 2-Butyl-6-fluoro-2,3,4,9-tetrahydro-2,4,9,10-tetraazacyclohepta[def]fluoren-8(1H)-one

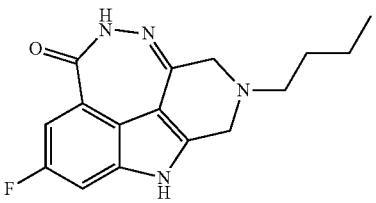 [SMILES: CCCCN1CC2=NNC(=O)c3cc(F)cc4[nH]c(c2c34)C1]

Compound 59 was prepared from methyl 2-bromo-5-fluoro-3-aminobenzoate and benzyl 3,5-dioxopiperidine-1-carboxylate according to the procedures similar to those for Compound 44. $^1$H NMR (DMSO-d$_6$) δ 11.8 (s, 1H), 10.1 (s, 1H), 7.36 (dd, 1H, J=2.4, 9.6 Hz), 7.19 (dd, 1H, J=2.4, 10.2 Hz), 3.80 (s, 2H), 3.30 (s, 2H), 2.54-2.57 (m, 2H), 1.47-1.50 (m, 2H), 1.30-1.34 (m, 2H), and 0.91 (t, 3H, J=7.2 Hz). MS (ESI) m/e [M+1]$^+$ 301.

Example 27: Synthesis of Compound 60

Compound 60: 2-(2-(dimethylamino)ethyl)-2,3,4,9-tetrahydro-2,4,9,10-tetraazacyclohepta[def]fluoren-8(1H)-one

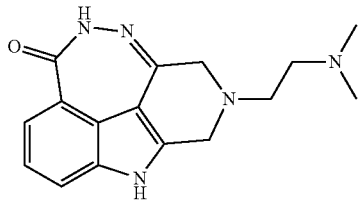 [SMILES: CN(C)CCN1CC2=NNC(=O)c3cccc4[nH]c(c2c34)C1]

Step 1: Methyl 2-(2-(dimethylamino)ethyl)-4-oxo-2,3,4,9-tetrahydro-H-pyrido[3,4-b]indole-5-carboxylate

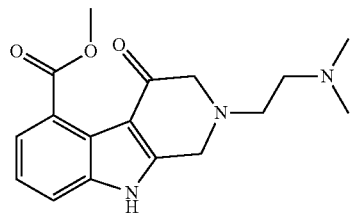 [SMILES: COC(=O)c1cccc2[nH]c3c(c12)C(=O)CN(CCN(C)C)C3]

Methyl 4-oxo-2,3,4,9-tetrahydro-1H-pyrido[3,4-b]indole-5-carboxylate (183 mg, 0.75 mol) was dissolved in DMF (20 ml) and 2-chloro-N,N-dimethylethanamine hydrochloride (107 mg, 0.75 mmol), and K$_2$CO$_3$ (207 mg, 1.5 mmol) were subsequently added. The reaction was stirred at 50° C. until the starting material was disappeared. The reaction mixture was then diluted with CH$_2$C$_{12}$ (15 ml) and washed with water three times. The organic layer was dried with MgSO$_4$. Evaporation of most of the solvent and the crude product was purified by chromatography column on silica gel (elution with CH$_2$Cl$_2$/MeOH/NH$_3$.H$_2$O) to provide 0.09 g of methyl 2-(2-(dimethylamino)ethyl)-4-oxo-2,3,4,9-tetrahydro-1H-pyrido[3,4-b]indole-5-carboxylate. MS (ESI) m/e [M+1]$^+$ 316.

Step 2: 2-(2-(dimethylamino)ethyl)-2,3,4,9-tetrahydro-2,4,9,10-tetraazacyclohepta[def]fluoren-8(1H)-one

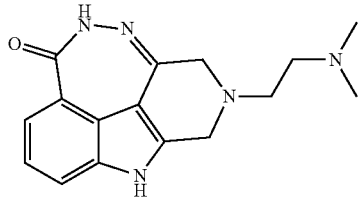 [SMILES: CN(C)CCN1CC2=NNC(=O)c3cccc4[nH]c(c2c34)C1]

Compound 60 was prepared from methyl 2-(2-(dimethylamino)ethyl)-4-oxo-2,3,4,9-tetrahydro-1H-pyrido[3,4-b]indole-5-carboxylate and hydrazine hydrate according to the procedure similar to that for Compound 1. $^1$H NMR δ 9.92 (s, 1H), 7.60 (d, 1H, J=8.4 Hz), 7.46 (d, 1H, J=7.8 Hz), 7.13 (dd, 1H, J=8.4, 7.8 Hz), 4.20-4.22 (m, 2H), 4.03 (s, 2H), 3.41 (s, 2H), 2.51-2.54 (m, 2H), and 2.18 (s, 6H). MS (ESI) m/e [M+1]$^+$ 298.

Example 28: Synthesis of Compound 61

Compound 61: 2-(2-(Dimethylamino)ethyl)-6-fluoro-2,3,4,9-tetrahydro-2,4,9,10-tetraazacyclohepta[def]fluoren-8(1H)-one

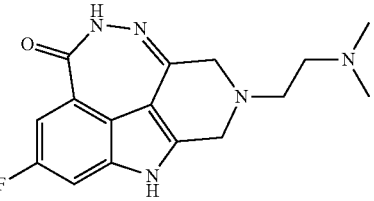

Compound 61 was prepared from methyl 2-bromo-5-fluoro-3-aminobenzoate and benzyl 3,5-dioxopiperidine-1-carboxylate according to the procedures similar to those for Compound 60. $^1$H NMR δ 10.1 (s, 1H), 7.58 (dd, 1H, J=1.8, 10.2 Hz), 7.21 (dd, 1H, J=1.8, 10.2 Hz), 4.20-4.22 (m, 2H), 4.03 (s, 2H), 3.42 (s, 2H), 2.51-2.54 (m, 2H), and 2.19 (s, 6H). MS (ESI) m/e [M+1]$^+$ 316.

Example 29: Synthesis of Compound 62

Compound 62: 2-(2-amino-2-methylpropanoyl)-2,3,4,9-tetrahydro-2,4,9,10-tetraazacyclohepta[def]fluoren-8(1H)-one

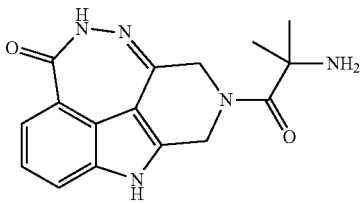 [SMILES: CC(C)(N)C(=O)N1CC2=NNC(=O)c3cccc4[nH]c(c2c34)C1]

Step 1: methyl 2-(2-(((benzyloxy)carbonyl)amino)-2-methylpropanoyl)-4-oxo-2,3,4,9-tetrahydro-1H-pyrido[3,4-b]indole-5-carboxylate

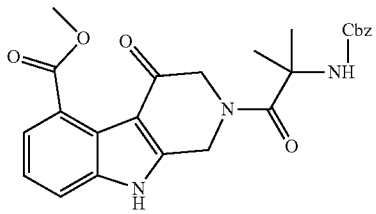 [SMILES: COC(=O)c1cccc2[nH]c3c(c12)C(=O)CN(C(=O)C(C)(C)NC(=O)OCc1ccccc1)C3]

A solution of HATU (86 mg) in DMF (2 ml) was added to a mixture of methyl 4-oxo-2,3,4,9-tetrahydro-1H-pyrido[3,4-b]indole-5-carboxylate (36 mg), 2-(((benzyloxy)carbonyl)amino)-2-methylpropanoic acid (21 mg), diisopropylethylamine (58) and DMF (8 ml) and the resultant mixture was stirred at ambient temperature for 16 hours. The DMF was evaporated to give methyl 2-(2-(((benzyloxy)carbonyl)amino)-2-methylpropanoyl)-4-oxo-2,3,4,9-tetrahydro-1H-pyrido[3,4-b]indole-5-carboxylate which was used in the next step without further purification.

Step 2: benzyl (2-methyl-1-oxo-1-(8-oxo-8,9-dihydro-2,4,9,10-tetraazacyclohepta[def]fluoren-2(1H,3H,4H)-yl)propan-2-yl)carbamate

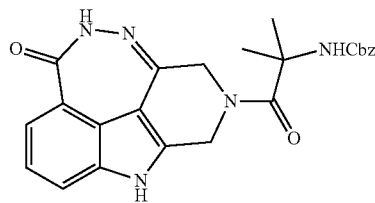 [SMILES: CC(C)(NC(=O)OCc1ccccc1)C(=O)N1CC2=NNC(=O)c3cccc4[nH]c(c2c34)C1]

The target product was prepared from 2-(2-(((benzyloxy)carbonyl)amino)-2-methylpropanoyl)-4-oxo-2,3,4,9-tetrahydro-1H-pyrido[3,4-b] indole-5-carboxylate and hydrazine hydrate according to the procedure similar to that for Compound 1. $^1$H NMR (DMSO-d$_6$) δ 11.8 (s, 1H), 10.2 (s, 1H), 7.18-7.55 (m, 8H), 4.82-4.91 (m, 4H), 4.43-4.55 (m, 2H), 1.25 (s, 6H). MS (ESI) m/e [M+1]$^+$ 446.

Step 3: 2-(2-amino-2-methylpropanoyl)-2,3,4,9-tetrahydro-2,4,9,10-tetraazacyclohepta[def]fluoren-8(1H)-one

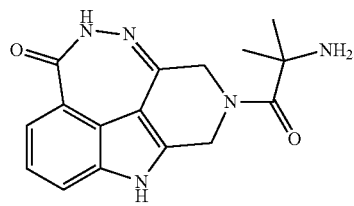 [SMILES: CC(C)(N)C(=O)N1CC2=NNC(=O)c3cccc4[nH]c(c2c34)C1]

Compound 62 was prepared from benzyl (2-methyl-1-oxo-1-(8-oxo-8,9-dihydro-2,4,9,10-tetraazacyclohepta[def]fluoren-2(1H,3H,4H)-yl)propan-2-yl)carbamate and Pd/C (10%) according to the procedure similar to that for Compound 42. $^1$H NMR (DMSO-d$_6$) δ 11.8 (s, 1H), 9.99 (s, 1H), 7.48 (d, 1H, J=8.0 Hz), 7.43 (d, 1H, J=7.2 Hz), 7.13 (dd, 1H, J=8.0, 7.2 Hz), 5.29-5.31 (m, 2H), 4.69-4.75 (m, 2H), 1.26 (s, 6H). MS (ESI) m/e [M+1]$^+$ 312.

Example 30: Synthesis of Compound 63

Compound 63: (S)-tert-butyl (1-oxo-1-(8-oxo-8,9-dihydro-2,4,9,10-tetraazacyclohepta[def] fluoren-2 (1H,3H,4H)-yl)-3-phenylpropan-2-yl)carbamate

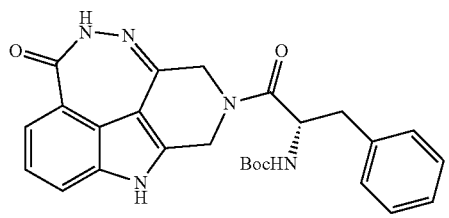 [SMILES: CC(C)(C)OC(=O)N[C@@H](Cc1ccccc1)C(=O)N1CC2=NNC(=O)c3cccc4[nH]c(c2c34)C1]

Compound 63 was prepared from 2,3,4,9-tetrahydro-2,4,9,10-tetraazacyclohepta[def]fluoren-8(1 H)-one and (S)-2-((tert-butoxycarbonyl)amino)-3-phenylpropanoic acid to the procedure similar to that for Compound 62. $^1$H NMR (DMSO-d$_6$) δ 11.8 (s, 1H), 10.0 (s, 1H), 7.51 (d, 1H, J=8.0 Hz), 7.05-7.47 (m, 7H), 4.96-5.02 (m, 1H), 4.25-4.81 (m, 4H), 2.62-2.88 (m, 2H), 1.27 (s, 6H), and 1.16 (s, 3H). MS (ESI) m/e [M+1]$^+$ 474.

Example 31: Synthesis of Compound 64

Compound 64: (S)-2-(2-amino-3-phenylpropanoyl)-2,3,4,9-tetrahydro-2,4,9,10-tetraazacyclohepta[def] fluoren-8(1H)-one

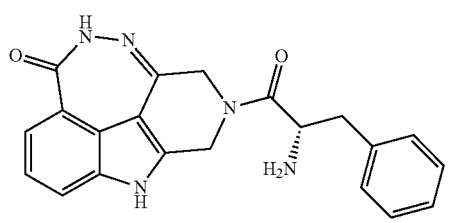 [SMILES: N[C@@H](Cc1ccccc1)C(=O)N1CC2=NNC(=O)c3cccc4[nH]c(c2c34)C1]

Compound 64 was prepared from Compound 63 with hydrogen chloride according to the procedure similar to that for Compound 62. $^1$H NMR (DMSO-d$_6$) δ 11.9 (s, 1H), 10.1 (s, 1H), 7.48 (d, 1H, J=8.0 Hz), 7.48-7.52 (m, 2H), 7.10-7.20 (m, 6H), 4.93-4.96 (m, 3H), 4.18-4.25 (m, 2H), 4.00-4.03 (m, 2H), 2.78-2.85 (m, 1H), and 2.61-2.65 (m, 1H). MS (ESI) m/e [M+1]$^+$ 374.

Example 32: Synthesis of Compound 65

Compound 65: 2-(2-amino-2-methylpropanoyl)-6-fluoro-2,3,4,9-tetrahydro-2,4,9,10-tetraazacyclohepta[def]fluoren-8(1H)-one

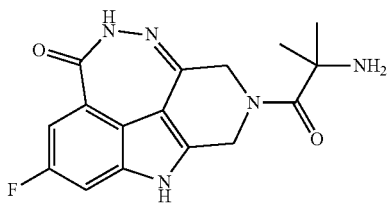 [SMILES: CC(C)(N)C(=O)N1CC2=NNC(=O)c3cc(F)cc4[nH]c(c2c34)C1]

Compound 65 was prepared from methyl 2-bromo-5-fluoro-3-aminobenzoate and benzyl 3,5-dioxopiperidine-1-carboxylate according to the same procedures similar to those for Compound 62. $^1$H NMR (DMSO-$d_6$) δ 12.1 (s, 1H), 10.2 (s, 1H), 7.40 (dd, 1H, J=1.8, 10.2 Hz), 7.20 (dd, 1H, J=1.8, 10.2 Hz), 5.25 (s, 2H), 4.75 (s, 1H), and 1.32 (s, 6H). MS (ESI) m/e [M+1]$^+$ 330.

Example 33: Synthesis of Compound 66

Compound 66: 5,10-Bis(2-hydroxyethyl)-2,2-dimethyl-2,3,5,10-tetrahydro-[1,2]diazepino[3,4,5,6-def]carbazol-6(1H)-one

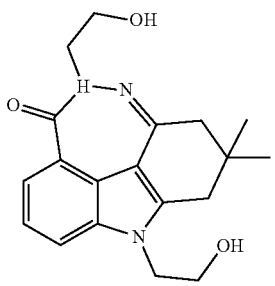

To a solution of 2,2-dimethyl-2,3,5,10-tetrahydro-[1,2]diazepino[3,4,5,6-def]carbazol-6(1H)-one (100 mg, 0.39 mmol) in dry DMF (8 mL) was added NaH (47 mg, 1.95 mmol) under ice bath. The reaction was stirred at 0° C. for 40 minutes. 2-(2-Bromoethoxy)tetrahydro-2H-pyran (194 mg, 1.17 mmol) was added to the mixture at 0° C. and the reaction was stirred at room temperature for 6 hours. Then water (100 mL) was added to the mixture, extracted with DCM (50 mL×3) and EA (50 mL×3). The organic layers were combined, washed with brine and dried over Na$_2$SO$_4$. The organic phase was concentrated to provide crude product. Then the crude product was dissolved in MeOH (15 mL), p-TSA.H$_2$O (100 mg, 0.52 mmol) was added to the solution and the mixture was stirred at room temperature for 16 hours. Water (150 mL) was added to the mixture, extracted with EA (50 mL×3). The combined organic layers were washed with saturated aqueous NaHCO$_3$ and brine, dried over Na$_2$SO$_4$, and concentrated The residue was purified by Pre-TLC (DCM/MeOH=10/1) to provide 40 mg (30%) of 5,10-bis(2-hydroxyethyl)-2,2-dimethyl-2,3,5,10-tetrahydro-[1,2]diazepino[3,4,5,6-def]carbazol-6(1H)-one as yellow solid. $^1$H NMR (DMSO-$d_6$) δ 7.57 (m, 2H), 7.15 (dd, 1H, J=7.2, 8.4 Hz), 4.88 (t, 1H, J=5.4 Hz), 4.61 (t, 1H, J=6.0 Hz), 4.21 (t, 2H, J=5.4 Hz), 3.94 (t, 2H, J=6.6 Hz), 3.94 (t, 2H, J=6.6 Hz), 3.63-3.68 (m, 2H), 2.77 (s, 2H), 2.28 (s, 2H), and 1.08 (s, 6H). MS (ESI) m/e [M+1]$^+$ 342.2.

Example 34: Synthesis of Compound 67

Compound 67: 10-(2-hydroxyethyl)-2,2-dimethyl-2,3,5,10-tetrahydro-[1,2]diazepino[3,4,5,6-def]carbazol-6(1H)-one

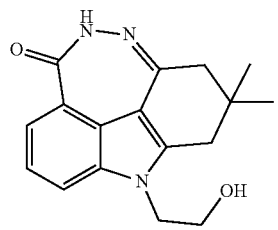 [SMILES: CC1(C)CC2=NNC(=O)c3cccc4c3c2c(n4CCO)C1]

To a solution of 2,2-dimethyl-2,3,5,10-tetrahydro-[1,2]diazepino[3,4,5,6-def]carbazol-6(1H)-one (100 mg, 0.39 mmol) in dry DMF (8 mL) was added 2-(2-bromoethoxy)tetrahydro-2H-pyran (194 mg, 1.17 mmol). K$_2$CO$_3$ (215 mg, 1.6 mmol) was added and the mixture was heated at 70° C. for 11.5 hours. Then water (100 mL) was added to the mixture, which was then extracted with EA (50 mL×3). The organic layers were combined, washed with brine, dried over Na$_2$SO$_4$, and concentrated to provide crude yellow oil. Then MeOH (15 mL) was added to the residue, followed by the addition of p-TSA.H$_2$O (100 mg, 0.52 mmol), and the mixture was stirred at room temperature for 1 hour. Water (100 mL) was added to the mixture, extracted with EA (50 mL×3). The organic layers were combined, washed with saturated aqueous NaHCO$_3$ and brine, dried over Na$_2$SO$_4$, and concentrated The residue was purified by chromatography column on silica gel (elution with hexane/ethyl acetate) to give 80 mg (69% yield) of 10-(2-hydroxyethyl)-2,2-dimethyl-2,3,5,10-tetrahydro-[1,2]diazepino[3,4,5,6-def]carbazol-6(1H)-one as yellow solid. $^1$H NMR (DMSO-$d_6$) δ 9.89 (s, 1H), 7.58 (d, 1H, J=8.4 Hz), 7.47 (d, 1H, J=7.2 Hz), 7.15 (dd, 1H, J=7.2, 8.4 Hz), 4.88 (t, 1H, J=5.4 Hz), 4.21 (t, 2H, J=5.4 Hz), 3.65-3.68 (m, 1H), 2.76 (s, 2H), 2.25 (s, 2H), and 1.07 (s, 6H). MS (ESI) m/e [M+1]$^+$ 298.1.

Example 35: Synthesis of Compound 68

Compound 68: (R)-10a-methyl-7,8,9,10,10a,11-hexahydro-5,6,7a,11-tetraazacyclohepta[def]cyclopenta[a]fluoren-4(5H)-one

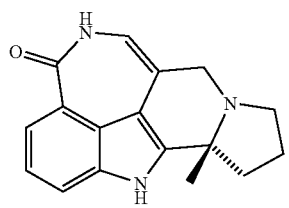 [SMILES: C[C@]12CCCN1CC1=CNC(=O)c3cccc4[nH]c2c1c34]

Step 1: (R)-methyl 2-(1-(benzyloxycarbonyl)-2-methylpyrrolidin-2-yl)-1H-indole-4-carboxylate

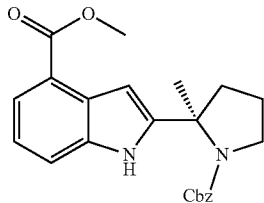 [SMILES: COC(=O)c1cccc2[nH]c([C@@]3(C)CCCN3C(=O)OCc3ccccc3)cc12]

To a suspension of tetrakis(triphenylphosphine)palladium (0)(1.72 g, 1.5 mmol) and CuI (0.29 g, 1.5 mmol) in 54 mL of toluene were added methyl 3-amino-2-bromobenzoate (2.3 g, 10 mmol), (R)-benzyl 2-ethynyl-2-methylpyrrolidine-1-carboxylate (3.0 g, 12 mmol), and TEA (7 mL, 50 mmol). The mixture was stirred for 18 h at 100° C. under nitrogen atmosphere. After cooling, water (20 mL) was added. The mixture was extracted with EtOAc (3×20 mL) and the combined organic layers were washed with brine (20 mL) and dried over $MgSO_4$. The mixture was filtered, and the filtrate was evaporated to dryness. The residue was purified by column chromatography on silica gel using $CH_2Cl_2$ as eluent to provide 2.31 g of (R)-benzyl 2-((2-amino-6-(methoxycarbonyl)phenyl)ethynyl)-2-methylpyrrolidine-1-carboxylate.

To a refluxing solution of (R)-benzyl 2-((2-amino-6-(methoxycarbonyl)phenyl)ethynyl)-2-methylpyrrolidine-1-carboxylate (1.1 g, 2.8 mmol) and dibromoethane (5.21 g, 2.8 mmol) in ethanol (20 mL) was added zinc powder (1.43 g, 22 mmol) in one portion. After refluxing for 8 h, the reaction mixture was filtered and the filtrate was concentrated to 3 mL, which was poured into water (15 mL). The reaction mixture was extracted with EA (20 mL×3). The combined extracts were dried over sodium sulfate, filtered, and evaporated to give pale brown oil, which was chromatographed over silica gel elution with hexane: ethyl acetate (5:1) to give the (R)-methyl 2-(1-(benzyloxycarbonyl)-2-methylpyrrolidin-2-yl)-1H-indole-4-carboxylate and (307 mg, 0.78 mmol). $^1$H NMR ($CDCl_3$-d) δ 10.3 (s, 1H), 7.83 (d, 1H, J=7.8 Hz), 7.53 (d, 1H, J=7.8 Hz), 7.29-7.35 (m, 5H), 7.16 (t, 1H, J=7.8 Hz), 6.96 (s, 1H), 5.15 (s, 2H), 3.95 (s, 3H), 3.56-3.59 (m, 2H), 2.83-2.85 (m, 1H), 2.03-2.07 (m, 2H), and 1.84-1.93 (m, 4H).MS (ESI) m/e [M+1]$^+$ 393.0.

Step 2: (R)-methyl 2-(2-methylpyrrolidin-2-yl)-1H-indole-4-carboxylate

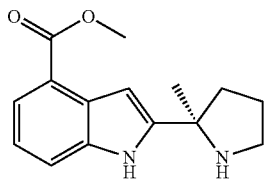 [SMILES: COC(=O)c1cccc2[nH]c([C@@]3(C)CCCN3)cc12]

A stirred mixture of (R)-methyl 2-(1-(benzyloxycarbonyl)-2-methylpyrrolidin-2-yl)-1H-indole-4-carboxylate (307 mg, 0.78 mol), methanol (10 mL), and 10% palladium on carbon (50 mg) was treated with a balloon-pressure of hydrogen at room temperature. After 2 hours, the mixture was filtered through Celite and the filtrate was concentrated to give (R)-methyl 2-(2-methylpyrrolidin-2-yl)-1H-indole-4-carboxylate (190 mg, 94%). $^1$H NMR ($CDCl_3$-d1) δ 10.9 (s, 1H), 7.86 (d, 1H, J=7.8 Hz), 7.63 (d, 1H, J=7.8 Hz), 7.24 (t, 1H, J=7.8 Hz), 7.14 (s, 1H), 3.96 (s, 3H), 3.40-3.43 (m, 1H), 3.12-3.15 (m, 1H), 2.78-2.81 (m, 1H), 2.23-2.26 (m, 3H), and 1.94 (s, 3H).MS (ESI) m/e [M+1]$^+$ 259.0.

Step 3: (R)-methyl 2-(1-(2-methoxy-2-oxoethyl)-2-methylpyrrolidin-2-yl)-1H-indole-4-carboxylate

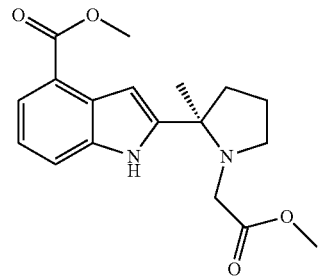 [SMILES: COC(=O)CN1CCC[C@]1(C)c1cc2c(C(=O)OC)cccc2[nH]1]

(R)-Methyl 2-(2-methylpyrrolidin-2-yl)-1H-indole-4-carboxylate (190 mg, 0.74 mmol) was dissolved in $CH_3CN$ (25 ml) and methylbromoacetate (250 mg, 1.6 mmol). DIPEA (350 mg, 2.7 mmol) was then added. The reaction mixture was stirred at room temperature for about 20 hours. The reaction mixture was then diluted with $CH_2Cl_2$ (15 ml) and washed with water three times. The organic layer was dried with $MgSO_4$ and concentrated to give 146 mg of(R)-methyl 2-(1-(2-methoxy-2-oxoethyl)-2-methylpyrrolidin-2-yl)-1H-indole-4-carboxylate. $^1$H NMR ($CDCl_3$-d) δ 7.85 (d, 1H, J=7.8 Hz), 7.13-7.29 (m, 3H), 4.92 (s, 2H), 3.95 (s, 3H), 3.70 (s, 3H), 3.56-3.62 (m, 2H), 1.95-2.06 (m, 4H), and 1.94 (s, 3H).MS (ESI) m/e [M+1]$^+$ 331.0.

Step 4: (R)-methyl 11 b-methyl-6-oxo-2,3,5,6,11,11 b-hexahydro-1H-indolizino[8,7-b]indole-7-carboxylate

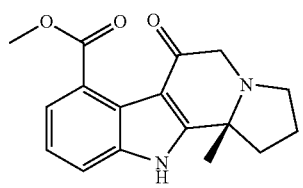 [SMILES: COC(=O)c1cccc2[nH]c3c(c12)C(=O)CN1CCC[C@]31C]

In a 25-mL flask, (R)-methyl 2-(1-(2-methoxy-2-oxoethyl)-2-methylpyrrolidin-2-yl)-1H-indole-4-carboxylate (146 mg, 0.44 mmol) was treated with anhydrous $MeSO_3H$ (10 mL). The flask was fitted with a reflux condenser and heated to 60° C. for 1 h. Then, the reaction mixture was cooled in an ice-bath and diluted with distilled water (2.0 mL). The pH of the solution was increased to pH-10 by the addition of saturated aq. $NaHCO_3$. The reaction mixture was then extracted with EtOAc (3×20 mL), and the organic extracts were washed with brine (1×20 mL), dried over $Na_2SO_4$, filtered, and concentrated. The residue was purified by flash chromatography (20 to 60% EtOAc/hexanes) to give (R)-methyl 11b-methyl-6-oxo-2,3,5,6,11,11 b-hexahydro-1H-indolizino[8,7-b]indole-7-carboxylate (58 mg 44%).MS (ESI) m/e [M+1]$^+$ 299.0.

Step 5: (R)-10a-methyl-7,8,9,10,10,11a,11-hexahydro-5,6,7a,11-tetraazacyclohepta[def]cyclopenta[a]fluoren-4(5H)-one

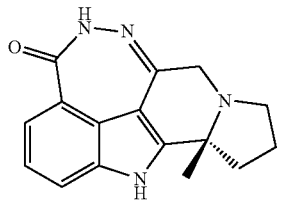 [SMILES: C[C@]12CCCN1CC1=NNC(=O)c3cccc4[nH]c2c1c34]

A solution of compound (R)-methyl 11 b-methyl-6-oxo-2,3,5,6,11,11b-hexahydro-1H-indolizino[8,7-b]indole-7-carboxylate (58 mg, 0.19 mmol), acetic acid (0.4 mL), and hydrazine hydrate (0.2 mL) in methanol (10 mL) was heated at reflux. After 7 h, the reaction was cooled and water (5 mL) was added. The mixture was extracted with EtOAc (3×5 mL) and the combined organic layers were washed with brine (10 mL) and dried over MgSO$_4$. The mixture was filtered, evaporated to dryness, and the residue was purified by Pre-TLC using CH$_2$Cl$_2$ as eluent to give 40 mg of (R)-10a-methyl-7,8,9,10,10a,11-hexahydro-5,6,7a,11-tetraazacyclohepta[def]cyclopenta[a]fluoren-4(5H)-one. $^1$H NMR (DMSO-d$_6$) δ 12.9 (s, 1H), 10.6 (s, 1H), 7.50-7.52 (m, 2H), 7.12 (t, 1H, J=7.8 Hz), 3.24-3.26 (m, 1H), 2.91 (d, 1H, J=18.4 Hz), 2.37-2.38 (m, 1H), 2.30-2.32 (m, 1H), 2.20-2.21 (m, 1H), 1.95-1.96 (m, 1H), 1.41-1.43 (m, 1H), 1.34 (s, 3H), and 1.18-1.19 (m, 1H). MS (ESI) m/e [M+1]$^+$ 281.0.

Example 36: Synthesis of Compound 69

Compound 69: (R)-2-fluoro-10a-methyl-7,8,9,10,11a,11-hexahydro-5,6,7a,11-tetraazacyclohepta[def]cyclopenta[a]fluoren-4(5H)-one

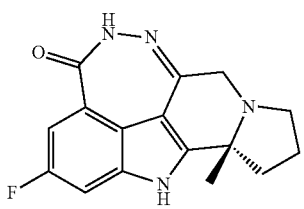 [SMILES: C[C@]12CCCN1CC1=NNC(=O)c3cc(F)cc4[nH]c2c1c34]

Step 1: Methyl 2-bromo-5-fluoro-3-(2,2,2-trifluoroacetamido)benzoate

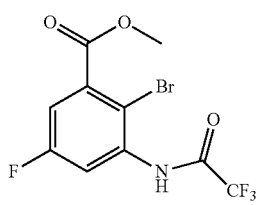 [SMILES: COC(=O)c1cc(F)cc(NC(=O)C(F)(F)F)c1Br]

To a solution of methyl 3-amino-2-bromo-5-fluorobenzoate (25.0 g, 100 mmol) and K$_2$CO$_3$ (42.0 g, 302 mmol) in DCM (250 mL) were added 2,2,2-trifluoroacetic anhydride (249.0 g, 1.197 mol) at 5 -10° C. under nitrogen atmosphere. The mixture was stirred for overnight at 25° C. The reaction mixture was diluted with DCM, washed with H$_2$O (200 mL×2) and saturated NaHCO$_3$aq (200 mL×2), dried over anhydrous Na$_2$SO$_4$, and concentrated to give 34.0 g (98%) of methyl 2-bromo-5-fluoro-3-(2,2,2-trifluoroacetamido)benzoate as white solid. $^1$H NMR (CDCl$_3$-d1) 6 8.87 (s, 1H), 8.36 (d, 1H, J=6.4 Hz), 7.43 (d, 1H, J=5.2 Hz), 3.98 (s, 3H).

Step 2: (R)-benzyl 2-((4-fluoro-2-(methoxycarbonyl)-6-(2,2,2trifluoroacetamido)phenyl)ethynyl)-2-methylpyrrolidine-1-carboxylate

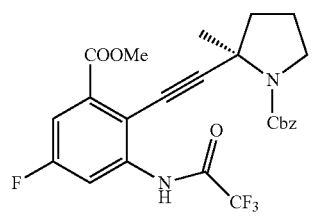 [SMILES: COC(=O)c1cc(F)cc(NC(=O)C(F)(F)F)c1C#C[C@@]1(C)CCCN1C(=O)OCc1ccccc1]

A mixture of methyl 2-bromo-5-fluoro-3-(2,2,2-trifluoroacetamido)benzoate (27.52 g, 80 mmol), (PPh$_3$)$_2$PdCl$_2$ (2.8 g, 4 mmol), (R)-benzyl 2-ethynyl-2-methylpyrrolidine-1-carboxylate (19.44 g, 80 mmol), copper(I) iodide (764 mg, 4 mmol) and tetramethylguanidine (27.6 g, 240 mmol) in DMF (200 mL) was heated at 80° C. with nitrogen protection system for 16 hours. The cooled reaction mixture was diluted with EA (3×200 mL) and water (800 mL). The organic layer was separated, washed with water (2×200 mL), dried (Na$_2$SO$_4$), and concentrated. The remaining residue was chromatographed on silica gel, eluted with gradient 0-30% EtOAc in hexane to give the product (R)-benzyl 2-((4-fluoro-2-(methoxycarbonyl)-6-(2,2,2trifluoroacetamido)phenyl)ethynyl)-2-methylpyrrolidine-1-carboxylate (21 g, 53%) as white solid. $^1$H NMR (DMSO-d1) δ 11.01 (s, 1H), 7.64-7.77 (m, 1H), 7.36 (m, 5H), 7.19-7.31 (m, 1H), 5.04-5.12 (m, 2H), 3.85 (s, 3H), 3.44-3.47 (m, 2H), 2.0-2.29 (m, 2H), 1.90-1.97 (m, 2H), and 1.69 (s, 3H). MS (ESI) m/e [M+1]$^+$ 507.0.

Step 3: (R)-methyl 6-fluoro-2-(2-methyl-1-(2,2,2-trifluoroacetyl)pyrrolidin-2-yl)-1H-indole-4-carboxylate

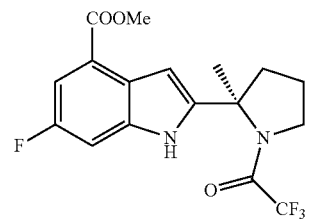

To a solution of (R)-benzyl 2-((4-fluoro-2-(methoxycarbonyl)-6-(2,2,2trifluoroacetamido)phenyl)ethynyl)-2-methylpyrrolidine-1-carboxylate(5.0 g, 10 mmol) in toluene was added zinc(II) bromide(11.25 g, 50 mmol) at room temperature. The reaction mixture was heated at 80° C. with nitrogen protection system for 15 hours. The solvent was removed under reduced pressure, and the residue was treated with DCM (500 mL) and water (800 mL). The organic layer was separated, washed with water (2×200 mL), dried (Na$_2$SO$_4$), and concentrated. The remaining residue was chromatographed on silica gel, eluted with gradient 0-50% EtOAc in hexane to give the product(R)-methyl 6-fluoro-2-(2-methyl-1-(2,2,2-trifluoroacetyl)pyrrolidin-2-yl)-1H-indole-4-carboxylate (1.9 g, 51%) as yellow solid. $^1$H NMR (CDCl$_3$-d1) δ 9.97 (s, 1H), 7.62 (d, H, J=10.2 Hz), 7.27 (d, 1H, J=9.6 Hz), 7.05 (d, 1H, J=1.2 Hz), 3.98 (s, 3H), 3.86-3.88 (m, 2H), 2.91-2.96 (m, 1H), 2.25-2.28 (m, 1H), 2.12-2.16 (m, 2H), and 1.99 (s, 3H). MS (ESI) m/e [M+1]$^+$ 507.0.

Step 4: (R)-methyl 6-fluoro-2-(2-methylpyrrolidin-2-yl)-1H-indole-4-carboxylate

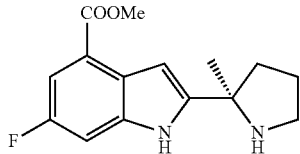 [SMILES: COC(=O)c1cc(F)cc2[nH]c([C@@]3(C)CCCN3)cc12]

To a solution of (R)-methyl 6-fluoro-2-(2-methyl-1-(2,2,2-trifluoroacetyl)pyrrolidin-2-yl)-1H-indole-4-carboxylate (1.0 g, 1.9 mmol) in MeOH was added NaBH$_4$ (706 mg, 11.4 mmol) at room temperature. The reaction mixture was refluxed for 4 hours with nitrogen protection system. The solvent was removed under reduced pressure. The residue was dissolved in DCM (200 mL), which was washed with water (200 mL) and brine (200 mL), dried over Na$_2$SO$_4$, and concentrated to give the desire product as yellow oil. (R)-methyl 6-fluoro-2-(2-methylpyrrolidin-2-yl)-1H-indole-4-carboxylate (727 mg, 98%). $^1$H NMR (CD$_3$OD-d1) δ 7.50 (dd, 1H, J=10.2, 2.4 Hz), 7.32 (d, 1H, J=9.0, 2.4 Hz), 6.93 (s, 1H), 3.97 (s, 3H), 3.03-3.12 (m, 2H), 2.27-2.32 (m, 1H), 1.88-1.98 (m, 3H), and 1.60 (s, 3H). MS (ESI) m/e [M+1]$^+$ 276.0.

Step 5: (R)-Methyl 6-fluoro-2-(1-(2-methoxy-2-oxoethyl)-2-methylpyrrolidin-2-yl)-1H-indole-4-carboxylate

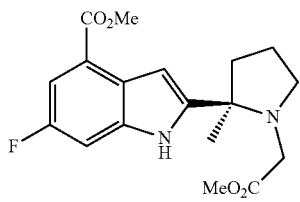 [SMILES: COC(=O)CN1CCC[C@]1(C)c1cc2c(C(=O)OC)cc(F)cc2[nH]1]

To a stirred mixture of (R)-methyl 6-fluoro-2-(2-methylpyrrolidin-2-yl)-1H-indole-4-carboxylate (1.0, 1.27 mol), CH$_3$CN (50 ml) and methylbromoacetate (0.58 g, 3.82 mmol) was added DIPEA (0.82 g, 6.35 mmol). The reaction mixture was stirred at room temperature for about 20 hours. The reaction mixture was then diluted with CH$_2$Cl$_2$ (15 ml) and washed with water three times. The organic layer was dried with MgSO$_4$ and concentrated to give 0.85 g of (R)-methyl 6-fluoro-2-(1-(2-methoxy-2-oxoethyl)-2-methylpyrrolidin-2-yl)-1H-indole-4-carboxylate. $^1$H NMR (CD$_3$OD-d4) δ 7.47 (dd, 1H, J=2.4, 12.0 Hz), 7.27 (dd, 1H, J=2.4, 9.0 Hz), 6.89 (s, 1H), 3.95 (s, 3H), 3.66-3.68 (m, 1H), 3.64 (s, 3H), 3.16-3.17 (m, 2H), 2.72-2.75 (m, 1H), 1.88-2.02 (m, 4H), and 1.44 (s, 3H).MS (ESI) m/e [M+1]$^+$ 349.0.

Step 6: (R)-methyl 9-fluoro-11 b-methyl-6-oxo-2,3,5,6,11,11b-hexahydro-1H-indolizino[8,7-b]indole-7-carboxylate

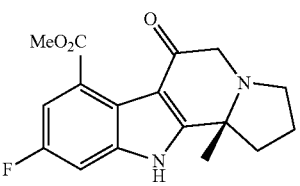 [SMILES: COC(=O)c1cc(F)cc2[nH]c3c(c12)C(=O)CN1CCC[C@]31C]

In a 25-mL flask, (R)-methyl 6-fluoro-2-(1-(2-methoxy-2-oxoethyl)-2-methylpyrrolidin-2-yl)-1H-indole-4-carboxylate (100 mg) was treated with anhydrous MeSO$_3$H (6 mL). The flask was fitted with a reflux condenser and heated at 60° C. for 1 h. Then, the reaction mixture was cooled in an ice-bath and diluted with distilled water (6.0 mL). The pH of the solution was increased to pH-10 by the addition of saturated aq. NaHCO$_3$. The reaction mixture was then extracted with EtOAc (3×5 mL). Theorganic extracts were combined and washed with brine (1×5 mL), dried over Na$_2$SO$_4$, filtered, and concentrated. The residue was purified by Pre-TLC to give (R)-methyl 9-fluoro-11 b-methyl-6-oxo-2,3,5,6,11,11b-hexahydro-1H-indolizino[8,7-b]indole-7-carboxylate(30 mg). $^1$H NMR (CDCl$_3$-d) δ 7.14-7.224 (m, 2H), 4.03 (s, 3H), 3.81-3.84 (m, 1H), 3.57-3.59 (m, 1H), 3.22-3.24 (m, 1H), 2.92-2.94 (m, 1H), 2.39-2.40 (m, 1H), 2.16-2.17 (m, 1H), 1.93-1.94 (m, 1H), 1.63 (s, 3H), and 1.56-1.57 (m, 1H).MS (ESI) m/e [M+1]$^+$ 317.0.

Step 7: (R)-2-fluoro-10a-methyl-7,8,9,10,10a,11-hexahydro-5,6,7a,11-tetraazacyclohepta[def]cyclopenta[a]fluoren-4(5H)-one

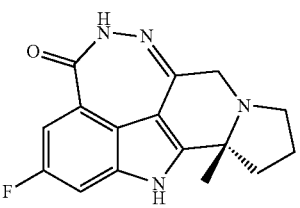 [SMILES: C[C@]12CCCN1CC1=NNC(=O)c3cc(F)cc4[nH]c2c1c34]

A solution of compound (R)-methyl 9-fluoro-11b-methyl-6-oxo-2,3,5,6,11,11 b-hexahydro-1H-indolizino[8,7-b]indole-7-carboxylate (90 mg), acetic acid (0.54 g), and hydrazine hydrate (0.28 g) in methanol (30 mL) was heated at reflux. After 5 h, the reaction was cooled and water (5 mL) was added. The mixture was extracted with EtOAc (3×5 mL). The combined organic layers were washed with brine (10 mL) and driedover MgSO$_4$. The mixture was filtered, and the filtrate was evaporated to dryness, and the residue was purified by Pre-TLC using CH$_2$Cl$_2$ as eluent to give 80 mg of(R)-2-fluoro-10a-methyl-7,8,9,10,10a,11-hexahydro-5,6,7a,11-tetraazacyclohepta[def]cyclopenta[a]fluoren-4 (5H)-one. $^1$H NMR (DMSO-d$_6$) δ 11.9 (s, 1H), 10.2 (s, 1H), 7.30 (d, 1H, J=9.6 Hz), 7.20 (d, 1H, J=10.2 Hz), 3.76 (d, 1H, J=16.4 Hz), 3.34 (d, 1H, J=16.4 Hz), 2.99-3.02 (m, 1H), 2.54-2.58 (m, 1H), 2.35-2.40 (m, 1H), 1.90-1.94 (m, 1H), 1.73-1.75 (m, 1H), 1.48 (s, 3H), and 1.43-1.45 (m, 1H). MS (ESI) m/e [M+1]$^+$ 299.

Biological Activity

PARP-1 Enzymatic Assay

PARP-1 enzymatic assay was conducted using a method modified from HT F Homogeneous PARP Inhibition Assay Kit (Trevigen). 8.8 nM PARP-1 was pre-incubated with different concentrations of compounds in a buffer containing 100 mM Tris-HCl pH 8.0, 100 mM NaCl, 20 mM MgCl2, and 1% DMSO for 30 min at RT. The auto-PARylation reaction was initiated by addition of 500 nM NAD and 20 ng/ul activated DNA (Sigma) and incubated at RT for 40 min. The remaining NAD was detected by incubation with cycling assay solution containing 1% ethanol, 0.30 U/ml alcohol dehydrogenase, 25 uM resazurin, and 0.25 U/ml diaphorase for 50 min at RT. The concentration of NAD is proportional to the fluorescence signal at Ex540 nm/Em 590 nm. The IC$_{50}$s were calculated based on residual enzyme activity (the rate of NAD decrease) in presence of increasing concentrations of compounds.

PARP-2 and PARP-3 Enzymatic Assay

PARP-2 and PARP-3 enzymatic assays were conducted using commercial PARP-2/PARP-3 Chemiluminescent Assay Kit (BPS Biosciences) and the protocols with the kits. Briefly, histones were coated in a high binding plate first, and incubated with PARP-2 or PARP-3, and increasing concentrations of compounds for 0.5h. Then, biotinylated NAD and activated DNA were added to the wells. The biotinylated PARylation product was measured by adding streptavidin-HRP and HRP substrates which produce chemiluminescence. The IC$_{50}$s were calculated based on residual enzyme activity in presence of increasing concentrations of compounds.

Tankyrase-2 Enzymatic Assay

Tankyrase-2 enzymatic assay was conducted using commercial Tankyrase-2 Chemiluminescent Assay Kit (BPS Biosciences) and the protocol with the kit. GST-fused tankyrase-2 (recombinant protein expressed and purified from Bacluovirus) were coated on a GSH-precoated plate first, and incubated with increasing concentrations of compounds for 0.5 h. Then, biotinylated NAD was added to the wells. The biotinylated auto-PARylation product was measured by adding streptavidin-HRP and HRP substrates which produce chemiluminescence. The IC$_{50}$s were calculated based on residual enzyme activity in presence of increasing concentrations of compounds.

PARylation Assay.

HeLa cells were seeded into a 96-wellplate with clear bottom and black wall at an initial concentration of 5000cells/well in culture medium (100 μL of DMEM containing 10% FBS, 0.1 mg/mL penicillin-streptomycin, and 2 mML-glutamine). The plates were incubated for 4 h at 37° C. under 5% $CO_2$ atmosphere, and then compounds were added with serial dilutions over eight points over a 0.01 nM-10 μM final concentration range in 0.1% DMSO/culture medium. The plate was then incubated for 18 h at 37° C. in 5% $CO_2$. Then DNA damage was provoked by addition of 60 μL of $H_2O_2$ solution in PBS (final concentration 200 μM). As a negative control, cells untreated with $H_2O_2$ were used. The plate was kept at 37° C. for 5 min. Then the medium was gently removed by plate inversion, and the cells were fixed by addition of ice-cold MeOH (100 μL/well) and kept at −20° C. for 20 min. After removal of the fixative by plate inversion and washing 10 times with PBS (120 μL), the detection buffer (50 μL/well, containing PBS, Tween (0.1%), and BSA (1 mg/mL)) together with the primary PAR mAb (Alexis ALX-804-220, 1:2000), the secondary anti-mouse Alexa Fluor 488 antibody (MolecularProbes A11029, 1:2000), and nuclear dye DAPI (Molecular Probes D3571, 150 nM) were added. Following overnight incubation at 4° C. in the dark, removal of the solution, and washing 6 times with PBS (120 μL), the plate was read on an ArrayScan VTI (ThermoFisher). Monitoring for PAR polymer was by detection of Alexa488 at XF100_485_20, exposure time of 0.05 s, and identification of the nuclei was by tracking DAPI with XF100_386_23, exposure time of 0.01 s. The mean of total intensity of cells was calculated by measuring the average of total intensity of nuclei over the total number of DAPI-labeled nuclei. The EC50 was determined on the basis of the residual enzyme activity in the presence of increasing PARPi concentration.

Compounds 1-69 as disclosed herein were tested and found to inhibit PARP, such as PARP-1, PARP-2, PARP-3, and Tankyrase-2, with IC$_{50}$ values ranging from subnanomolar to 10 micromolar.

| | | | | | |
|---|---|---|---|---|---|
| | | | | | IC50s and EC50s (nM) |
| Compound | PARP-1 IC50 | PARP-2 IC50 | PARP-3 IC50 | Tankyrase-2 IC50 | PARP PARylation EC50 |
| 1 | 10 | 1.9 | 199 | 140 | 3.6 |

-continued
| | | | IC50s and EC50s (nM) | | |
|---|---|---|---|---|---|
| Compound | PARP-1 IC50 | PARP-2 IC50 | PARP-3 IC50 | Tankyrase-2 IC50 | PARP PARylation EC50 |
| 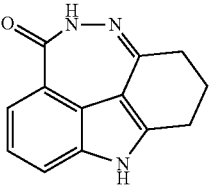<br>2 | 6.7 | 1.3 | | 154 | 3.1 |
| 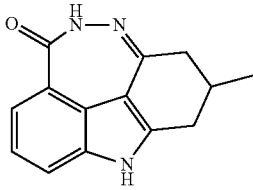<br>3 | 7.6 | 1.7 | | 143 | 4.6 |
| 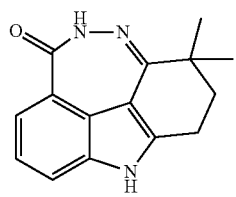<br>4 | 18.6 | | | 1050 | 46.7 |
| 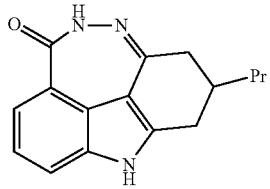<br>5 | 6.3 | 1.6 | | 164 | 10.1 |
| 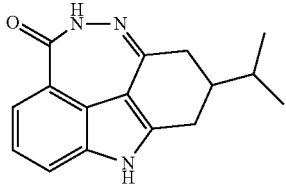<br>6 | 6 | 1.1 | | 80 | 3.9 |

-continued

| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 7 | 6 | 0.8 | | 102 | 5.5 |
| 8 | 6.5 | | | | 3.5 |
| 9 | 5.2 | | 136 | 203 | 1.7 |
| 10 | 5.8 | | | | 12.4 |
| 11 | 3.3 | | | 29 | 2.4 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 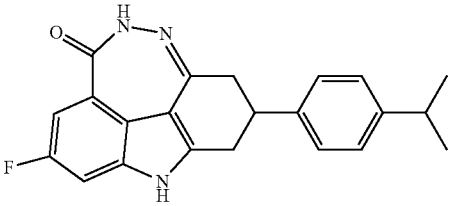 12 | 25.6 | | | | 26.6 |
| 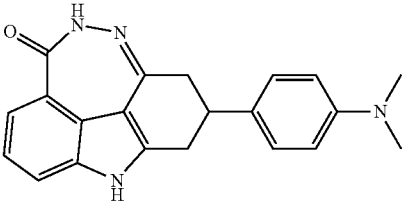 13 | 19.8 | | | | 77.6 |
| 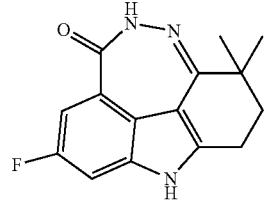 14 | 5.2 | 0.7 | | | |
| 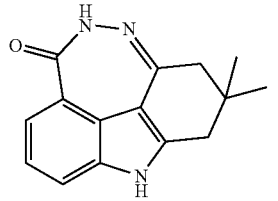 15 | 6.3 | 0.6 | | 832 | 2.9 |
| 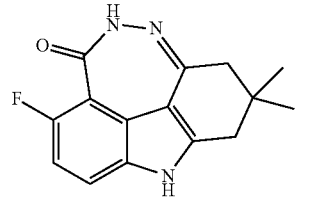 16 | 9.1 | 0.7 | | | 4.8 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 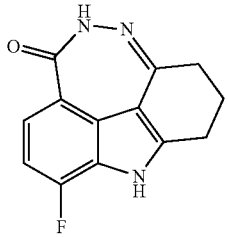 17 | 24 | | | | 15 |
| 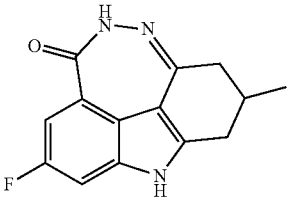 18 | 6.0 | | | | |
| 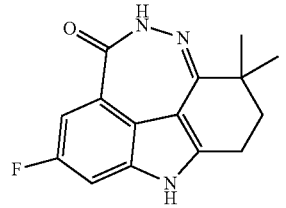 19 | 5.2 | 0.7 | | | |
| 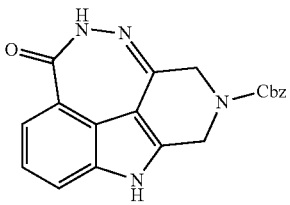 20 | 8.9 | 0.5 | | | 7.3 |
| 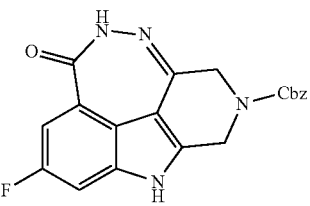 21 | 7.0 | 0.3 | | | 14 |

-continued

| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 22 | 15.8 | | | | 75 |
| 23 | 15.2 | | | | 207 |
| 24 | >1000 | | | | |
| 25 | >1000 | | | | >1000 |
| 26 | 11.4 | 0.9 | | | 4.5 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 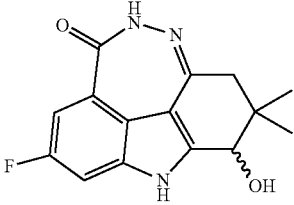<br>27 | 11 | | | | 4.4 |
| 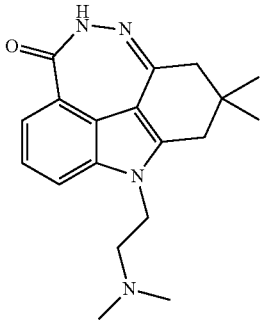<br>28 | 5.5 | | | 1300 | 4.9 |
| 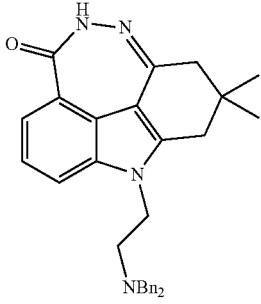<br>29 | >1000 | | | | 630 |
| 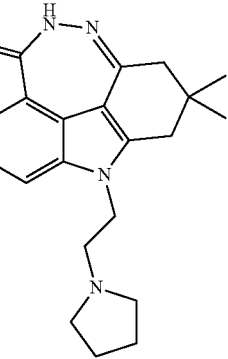<br>30 | 6.6 | | | 1500 | 8.1 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 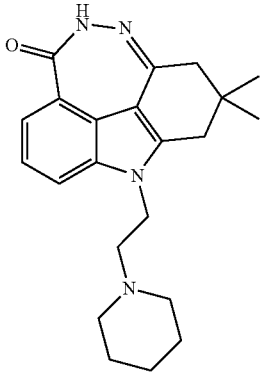<br>31 | 2.9 | 0.2 | >20000 | 700 | 3.2 |
| 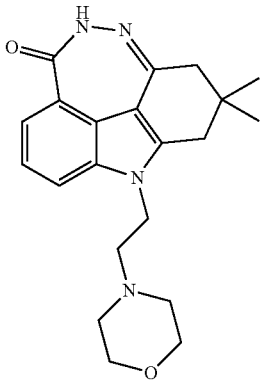<br>32 | 190 | | | | 1590 |
| 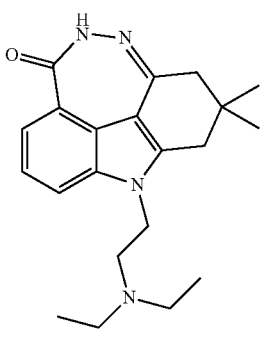<br>33 | 3.3 | 0.3 | 11000 | 2400 | 12 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 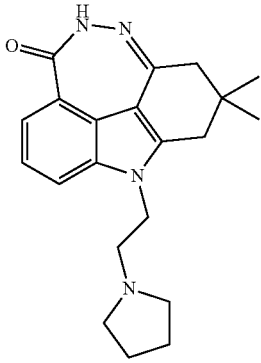  34 | 11 | | | 150 | 33 |
| 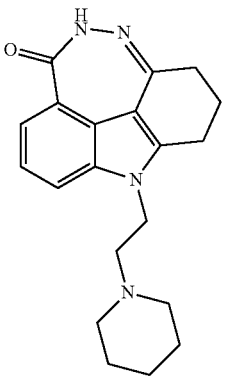  35 | 10 | | | 130 | 23 |
| 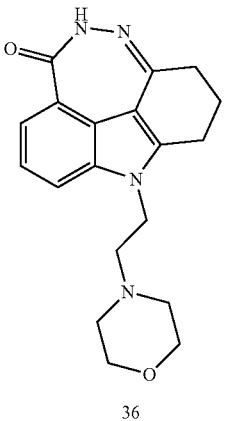 [SMILES: O=C1NN=C2CCCc3c2c2c1cccc2n3CCN1CCOCC1]  36 | 350 | | | | 1510 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 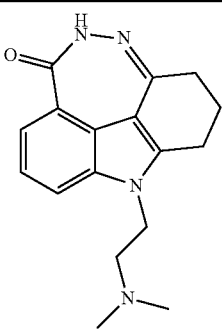<br>37 | 15 | | | | 22 |
| 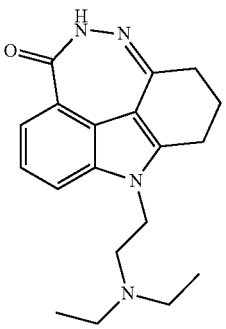<br>38 | 16 | | | | 30 |
| 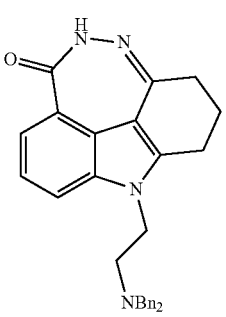<br>39 | 800 | | | | 2010 |
| 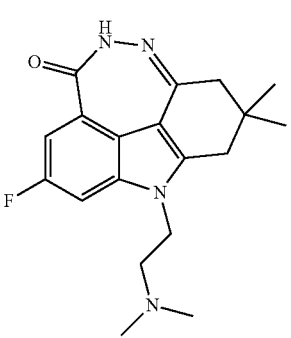<br>40 | 6.5 | | | 480 | 2.4 |

-continued

| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 41 | 27 | 21 | 1000 | | 2.3 |
| 42 | 10 | | | | 6.9 |
| 43 | 8.5 | | | | 8.0 |
| 44 | 16 | | | | 24 |
| 45 | 7.1 | 0.8 | 760 | 1200 | 3.8 |

-continued

IC50s and EC50s (nM)

| Compound | PARP-1 IC50 | PARP-2 IC50 | PARP-3 IC50 | Tankyrase-2 IC50 | PARP PARylation EC50 |
|---|---|---|---|---|---|
| 46 | 5.1 | | | | 1.4 |
| 47 | 3.3 | 0.3 | 180 | | 6.9 |
| 48 | 11 | | | | 6.0 |
| 49 | 2.3 | | | | 1.4 |
| 50 | 18 | | | | 21 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 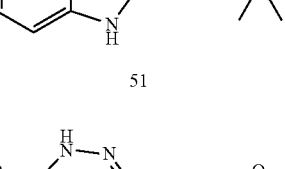<br>51 | 11 | 1.3 | 660 | | 9.6 |
| 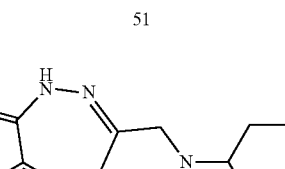<br>51 | 7.3 | | | | 13.5 |
| 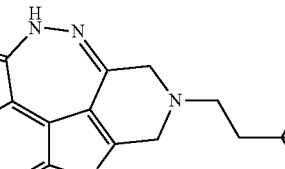<br>53 | 9.2 | | | | 20 |
| 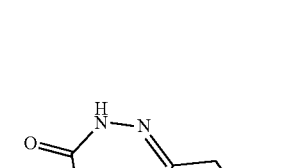<br>54 | 14 | | | | 23 |
| 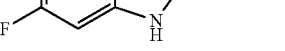<br>55 | 5.7 | | | | 4.3 |

-continued

| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 56 | 8.3 | | | | 6.4 |
| 57 | 4.5 | | | | 3.4 |
| 58 | 4.8 | | | | 1.5 |
| 59 | 3.8 | | | | 2.0 |
| 60 | 27 | | | | 68.5 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 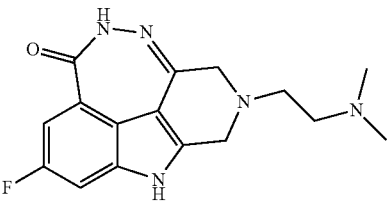<br>61 | 38 | | | | 42 |
| 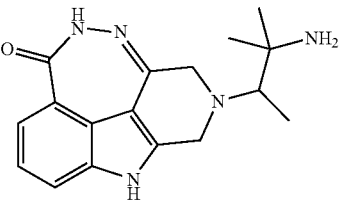<br>62 | 7.2(2.6) | 1.0 | 18 | 3800 | 4.0 |
| 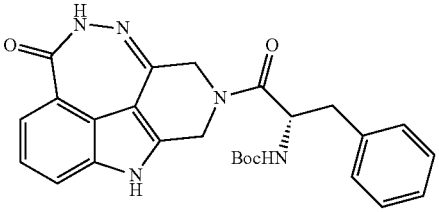<br>63 | 100 | | | | 235 |
| 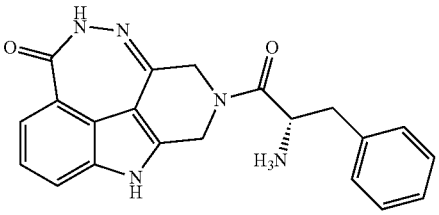<br>64 | 33 | | | | 46 |
| 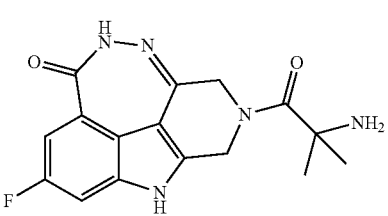<br>65 | 12 | | | | 2.9 |

-continued
| | IC50s and EC50s (nM) | | | | |
|---|---|---|---|---|---|
| Compound | PARP-1 IC50 | PARP-2 IC50 | PARP-3 IC50 | Tankyrase-2 IC50 | PARP PARylation EC50 |
| 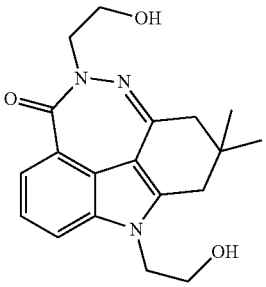 66 | 1900 | | | | |
| 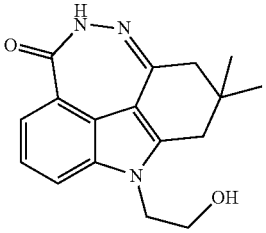 67 | 23 | | | | 247 |
| 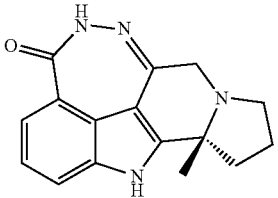 68 | 1.1 | 0.4 | | 1220 | 0.6 |
| 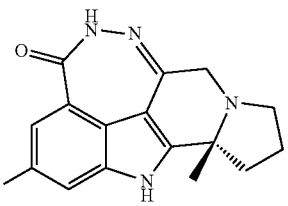 69 | 0.9 | 0.5 | 185 | 766 | 0.6 |

What is claimed is:

1. An oral dosage form comprising a compound of Formula (I) or a stereoisomer or a pharmaceutically acceptable salt thereof, in an amount effective to inhibit PARP:

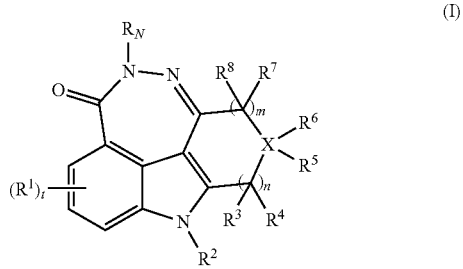

wherein:
- $R_N$ is selected from hydrogen, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
- X is selected from C, N, O, or S;
- m and n, which may be the same or different, are each an integer of 0, 1, 2, or 3;
- t is an integer of 0, 1, 2, or 3;
- $R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
- $R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
- $R^3$, $R^4$, $R^5$, $R^6$, $R^7$ and $R^8$, which may be the same or different, are each independently selected from hydrogen, halogen, $—NR^9R^{10}$, $—OR^9$, oxo, $—COR^9$, $—CO_2R^9$, $—CONR^9R^{10}$, $—NR^9CONR^{10}R^{11}$, $—NR^9CO_2R^{10}$, $—NR^9SO_2R^{10}$, $—SO_2R^9$, alkyl, alkenyl, cycloalkyl, aryl, heterocyclyl, alkynyl, or heteroaryl, wherein each of the alkyl, alkenyl, alkynyl, cycloalkyl, aryl, heterocyclyl, and heteroaryl is independently optionally substituted with at least one substituent $R^{12}$;
- or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) they are attached, form a 3- to 8-membered saturated, partially or fully unsaturated ring having 0, 1 or 2 heteroatoms independently selected from $—NR^{13}—$, $—O—$, $—S—$, $—SO—$ or $—SO_2-$, and said ring is optionally substituted with at least one substituent $R^{12}$;
- provided that
  - when X is O, $R^5$ and $R^6$ are absent,
  - when X is N, $R^6$ is absent,
  - when X is S, $R^5$ and $R^6$ are absent, or at least one of $R^5$ and $R^6$ is oxo,
  - when one of $R^3$ and $R^4$ is oxo, the other is absent,
  - when one of $R^7$ and $R^8$ is oxo, the other is absent, and
  - when X is C and one of $R^5$ and $R^6$ is oxo, the other is absent;
- $R^9$, $R^{10}$, and $R^{11}$, which may be the same or different, are each selected from hydrogen, alkyl, alkenyl, alkynyl, cycloalkyl, heterocyclyl, aryl, or heteroaryl, wherein each of the alkyl, alkenyl, alkynyl, cycloalkyl, heterocyclyl, aryl, or heteroaryl is independently optionally substituted with at least one substituent $R^{12}$;
- $R^{12}$ is selected from CN, halogen, haloalkyl, $NO_2$, $—NR'R''$, $—OR'$, oxo, $—COR'$, $—CO_2R'$, $—CONR'R''$, $—NR'CONR''R'''$, $—NR'CO_2R''$, $—NR'SO_2R''$, $—SO_2R'$, alkyl, alkenyl, alkynyl, cycloalkyl, heterocyclyl, aryl, or heteroaryl, wherein $R'$, $R''$, and $R'''$ are independently selected from hydrogen, haloalkyl, alkyl, arylalkyl, alkenyl, alkynyl, cycloalkyl, heterocyclyl, aryl, or heteroaryl, or ($R'$ and $R''$), and/or ($R''$ and $R'''$) together with the atoms to which they are attached, form a 3- to 8-membered saturated, partially or fully unsaturated ring having 0, 1 or 2 additional heteroatoms independently selected from $—NR^{13}—$, $—O—$, $—S—$, $—SO—$ or $—SO_2-$; and
- $R^{13}$ is selected from hydrogen, alkyl, cycloalkyl, aryl, heteroaryl, or heterocyclyl,
- wherein the cycloalkyl is a hydrocarbon group selected from saturated or partially unsaturated cyclic hydrocarbon groups, comprising monocyclic, bicyclic or tricyclic groups, and comprising from 3 to 12 carbon atoms;
- wherein the heteroaryl is a group selected from:
  - 5- to 7-membered aromatic, monocyclic rings comprising at least one heteroatom selected from N, O, or S, with the remaining ring atoms being carbon;
  - 8- to 12-membered bicyclic rings comprising at least one heteroatom selected from N, O, or S, with the remaining ring atoms being carbon and wherein at least one ring is aromatic and at least one heteroatom is present in the aromatic ring; and
  - 11- to 14-membered tricyclic rings comprising at least one heteroatom selected from N, O, or S, with the remaining ring atoms being carbon and wherein at least one ring is aromatic and at least one heteroatom is present in an aromatic ring; and
- wherein the heterocyclyl is a ring selected from 4- to 12-membered monocyclic, bicyclic or tricyclic, saturated or partially unsaturated rings, comprising at least one carbon atoms in addition to at least one heteroatom selected from oxygen, sulfur, or nitrogen;
- and a pharmaceutically acceptable carrier.

2. The oral dosage form of claim 1, wherein $R_N$ is hydrogen or alkyl, wherein the alkyl is optionally substituted with at least one of hydroxyl or $C_1$-$C_{12}$ alkoxyl.

3. The oral dosage form of claim 1, wherein X is C or N.

4. The oral dosage form of claim 1, wherein m and n are each 1 or 2.

5. The oral dosage form of claim 1, wherein t is 0 or 1.

6. The oral dosage form of claim 1, wherein $R^2$ is hydrogen or alkyl.

7. The oral dosage form of claim 1, wherein $R^3$, $R^4$, $R^5$, $R^6$, $R^7$ and $R^8$, which may be the same or different, are each independently selected from hydrogen, $—OR^9$, $—COR^9$, $—CO_2R^9$, alkyl, cycloalkyl, or aryl.

8. The oral dosage form of claim 1, wherein the compound is a compound of Formula (II):

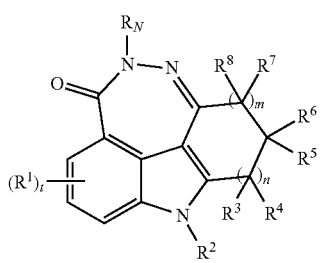

(II)

or a stereoisomer or a pharmaceutically acceptable salt thereof,
wherein:
$R_N$ is selected from hydrogen, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
m and n, which may be the same or different, are each an integer of 0, 1, 2, or 3;
t is an integer of 0, 1, 2, or 3;
$R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
$R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
$R^3$, $R^4$, $R^5$, $R^6$, $R^7$ and $R^8$, which may be the same or different, are each independently selected from hydrogen, halogen, —$NR^9R^{10}$, —$OR^9$, oxo, —$COR^9$, —$CO_2R^9$, —$CONR^9R^{10}$, —$NR^9CONR^{10}R^{11}$, —$NR^9CO_2R^{10}$, —$NR^9SO_2R^{10}$, —$SO_2R^9$, alkyl, alkenyl, alkynyl, cycloalkyl, aryl, heterocyclyl, alkynyl, or heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) to which they are attached, form a 3- to 8-membered saturated, partially or fully unsaturated ring having 0, 1 or 2 heteroatoms independently selected from —$NR^{13}$—, —O—, —S—, —SO— or —$SO_2$-, and said ring is optionally substituted with at least one substituent $R^{12}$, provided that
when one of $R^3$ and $R^4$ is oxo, the other is absent,
when one of $R^7$ and $R^8$ is oxo, the other is absent, and
when one of $R^5$ and $R^6$ is oxo, the other is absent;
$R^9$, $R^{10}$, and $R^{11}$, which may be the same or different, are each selected from hydrogen, alkyl, alkenyl, alkynyl, cycloalkyl, heterocyclyl, aryl, or heteroaryl, wherein each of the alkyl, alkenyl, alkynyl, cycloalkyl, heterocyclyl, aryl, or heteroaryl is independently optionally substituted with at least one substituent $R^{12}$;

$R^{12}$ is selected from CN, halogen, haloalkyl, $NO_2$, —NR'R", —OR', oxo, —COR', —$CO_2R'$, —CONR'R", —NR'CONR"R"', —NR'$CO_2R"$, —NR'$SO_2R"$, —$SO_2R'$, alkyl, alkenyl, alkynyl, cycloalkyl, heterocyclyl, aryl, or heteroaryl, wherein R', R", and R"' are independently selected from hydrogen, haloalkyl, alkyl, arylalkyl, alkenyl, alkynyl, cycloalkyl, heterocyclyl, aryl, or heteroaryl, or (R' and R"), and/or (R" and R"') together with the atoms to which they are attached, form a 3- to 8-membered saturated, partially or fully unsaturated ring having 0, 1 or 2 additional heteroatoms independently selected from —$NR^{13}$—, —O—, —S—, —SO— or —$SO_2$-; and
$R^{13}$ is selected from hydrogen, alkyl, cycloalkyl, aryl, heteroaryl, or heterocyclyl.

9. The oral dosage form of claim 8, wherein:
$R_N$ is selected from hydrogen or alkyl, wherein the alkyl is optionally substituted with at least one of hydroxyl or $C_1$-$C_{12}$ alkoxyl;
m and n are each 1 or 2;
t is 0 or 1;
$R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
$R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, or heteroaryl;
$R^3$, $R^4$, $R^5$, $R^6$, $R^7$ and $R^8$, which may be the same or different, are each independently selected from hydrogen, —$OR^9$, —$COR^9$, —$CO_2R^9$, alkyl, cycloalkyl, or aryl,
or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) to which they are attached, form a 3- to 8-membered saturated, partially or fully unsaturated ring having 0, 1 or 2 heteroatoms independently selected from —$NR^{13}$-, —O—, —S—, —SO— or —$SO_2$-;
$R^9$ and $R^{10}$, which may be the same or different, are each selected from hydrogen, alkyl, alkenyl, alkynyl, cycloalkyl, heterocyclyl, aryl, or heteroaryl; and
$R^{13}$ is selected from hydrogen, alkyl, cycloalkyl, aryl, heteroaryl, or heterocyclyl.

10. The oral dosage form of claim 1, wherein the compound is a compound of Formula (III):

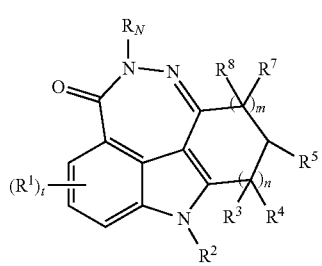

(III)

or a stereoisomer or a pharmaceutically acceptable salt thereof, wherein:
  $R_N$ is selected from hydrogen, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
  m and n, which may be the same or different, are each an integer of 0, 1, 2, or 3;
  t is an integer of 0, 1, 2, or 3;
  $R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
  $R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
  $R^3$, $R^4$, $R^5$, $R^7$ and $R^8$, which may be the same or different, are each independently selected from hydrogen, halogen, $-NR^9R^{10}$, $-OR^9$, oxo, $-COR^9$, $-CO_2R^9$, $-CONR^9R^{10}$, $-NR^9CONR^{10}R^{11}$, $-NR^9CO_2R^{10}$, $-NR^9SO_2R^{10}$, $-SO_2R^9$, alkyl, alkenyl, cycloalkyl, aryl, heterocyclyl, alkynyl, or heteroaryl, wherein each of the alkyl, alkenyl, alkynyl, cycloalkyl, aryl, heterocyclyl, or heteroaryl is independently optionally substituted with at least one substituent $R^{12}$, or ($R^3$ and $R^4$), and/or ($R^4$ and $R^5$), and/or ($R^5$ and $R^7$), and/or ($R^7$ and $R^8$), together with the atom(s) they are attached, form a 3- to 8-membered saturated, partially or fully unsaturated ring having 0, 1 or 2 heteroatoms independently selected from $-NR^{13}-$, $-O-$, $-S-$, $-SO-$, or $-SO_2$-, and said ring is optionally substituted with at least one substituent $R^{12}$,
  provided that
    when one of $R^3$ and $R^4$ is oxo, the other is absent, and when one of $R^7$ and $R^8$ is oxo, the other is absent;
  $R^9$, $R^{10}$, and $R^{11}$, which may be the same or different, are each selected from hydrogen, alkyl, alkenyl, alkynyl, cycloalkyl, heterocyclyl, aryl, or heteroaryl, wherein each of the alkyl, alkenyl, alkynyl, cycloalkyl, heterocyclyl, aryl, and heteroaryl is independently optionally substituted with at least one substituent $R^{12}$;
  $R^{12}$ is selected from CN, halogen, haloalkyl, $NO_2$, $-NR'R''$, $-OR'$, oxo, $-COR'$, $-CO_2R'$, $-CONR'R''$, $-NR'CONR''R'''$, $-NR'CO_2R''$, $-NR'SO_2R''$, $-SO_2R'$, alkyl, alkenyl, alkynyl, cycloalkyl, heterocyclyl, aryl, or heteroaryl, wherein R', R'', and R''' are independently selected from hydrogen, haloalkyl, alkyl, arylalkyl, alkenyl, alkynyl, cycloalkyl, heterocyclyl, aryl, or heteroaryl, or (R' and R''), and/or (R'' and R''') together with the atoms to which they are attached, form a 3- to 8-membered saturated, partially or fully unsaturated ring having 0, 1 or 2 additional heteroatoms independently selected from $-NR^{13}-$, $-O-$, $-S-$, $-SO-$ or $-SO_2$-; and $R^{13}$ is selected from hydrogen, alkyl, cycloalkyl, aryl, heteroaryl, or heterocyclyl.

11. The oral dosage form of claim 10, wherein:
  $R_N$ is hydrogen or alkyl, wherein the alkyl is optionally substituted with at least one of hydroxyl or $C_1$-$C_{12}$ alkoxyl;
  X is C or N;
  m and n are each 1 or 2;
  t is 0 or 1;
  $R^1$, at each occurrence, is independently selected from halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, or heteroaryl;
  $R^2$ is hydrogen or alkyl;
  $R^3$, $R^4$, $R^5$, $R^7$ and $R^8$, which may be the same or different, are each independently selected from hydrogen, $-OR^9$, $-COR^9$, $-CO_2R^9$, alkyl, cycloalkyl, or aryl, or ($R^3$ and $R^4$), and/or ($R^4$ and $R^5$), and/or ($R^5$ and $R^7$), and/or ($R^7$ and $R^8$), together with the atom(s) they are attached, form a 3- to 8-membered saturated, partially or fully unsaturated ring having 0, 1 or 2 heteroatoms independently selected from $-NR^{13}$-, $-O-$, $-S-$, $-SO-$, or $-SO_2$-;
  $R^9$ and $R^{10}$, which may be the same or different, are each selected from hydrogen, alkyl, alkenyl, alkynyl, cycloalkyl, heterocyclyl, aryl, or heteroaryl; and
  $R^{13}$ is selected from hydrogen, alkyl, cycloalkyl, aryl, heteroaryl, or heterocyclyl.

12. The oral dosage form of claim 1, wherein the compound is

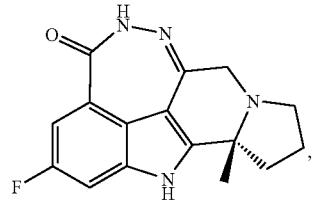 [SMILES: C[C@]12CCCN1CC1=NNC(=O)c3cc(F)cc4[nH]c2c1c34]

or a stereoisomer or a pharmaceutically acceptable salt thereof.

13. The oral dosage form of claim 1, wherein the compound is selected from the group consisting of:

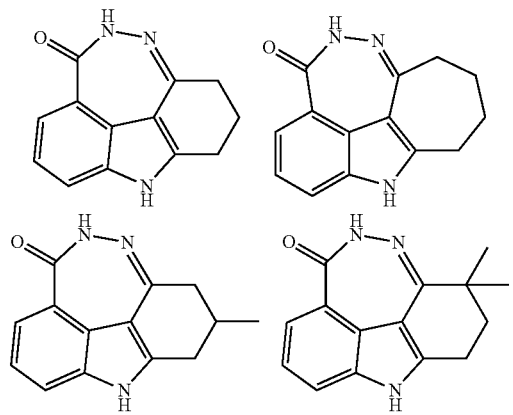

117
-continued
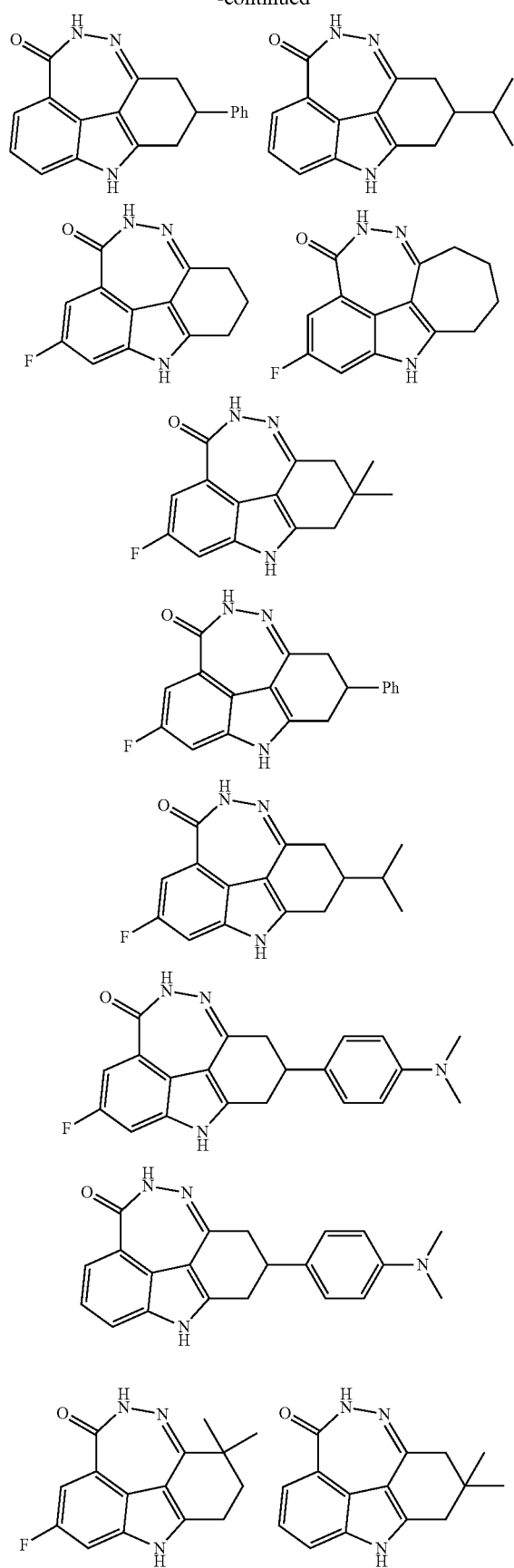
118
-continued
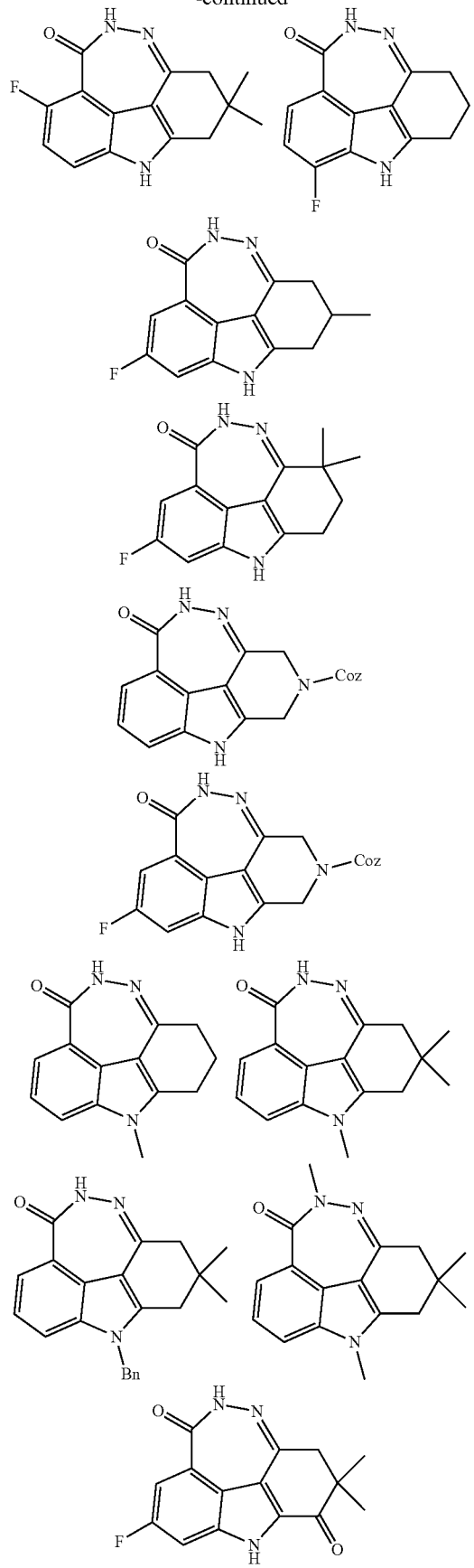

119
-continued
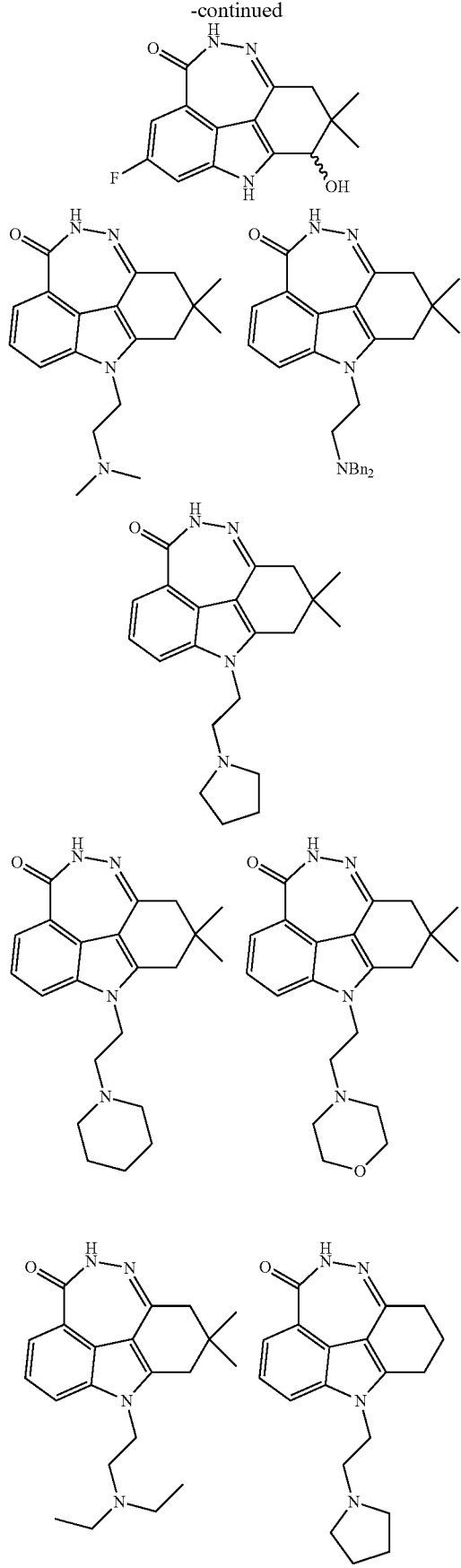
120
-continued
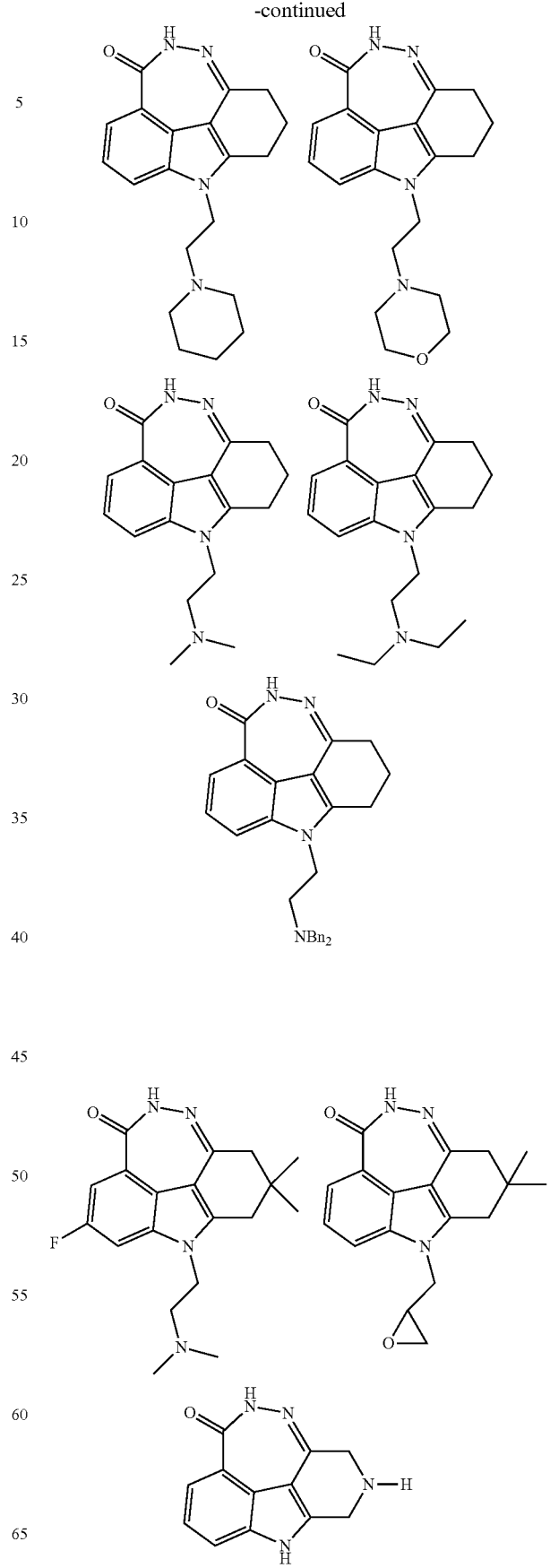

121
-continued
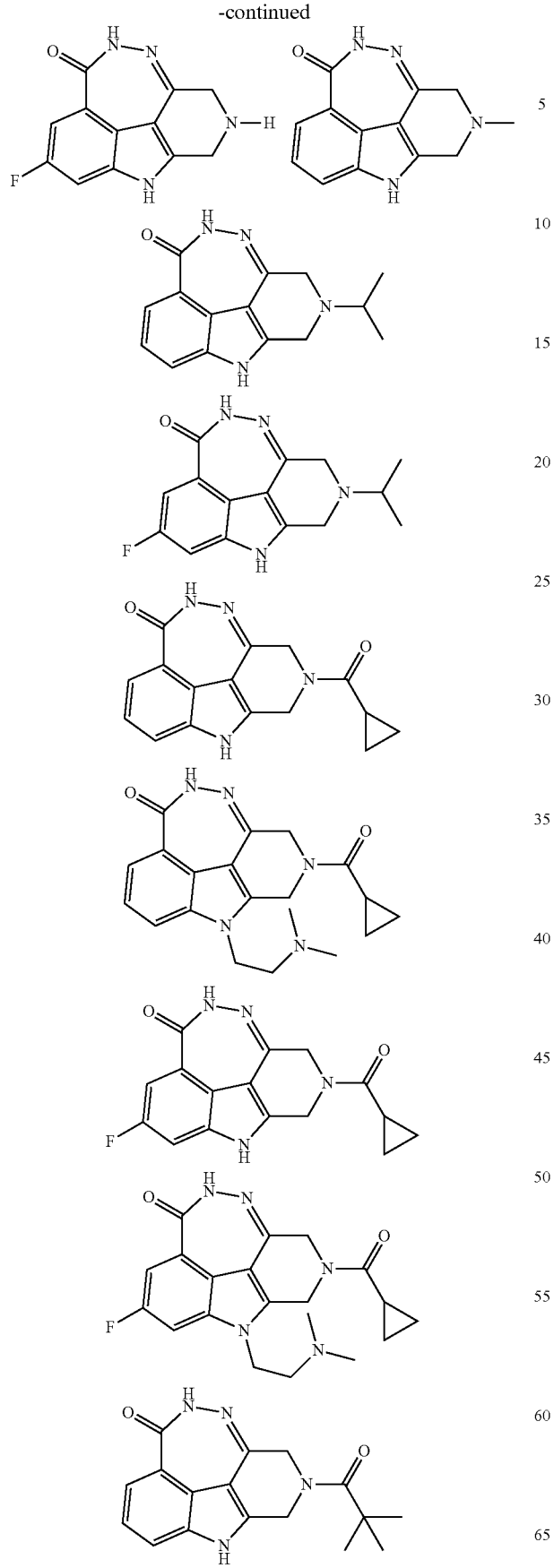
122
-continued
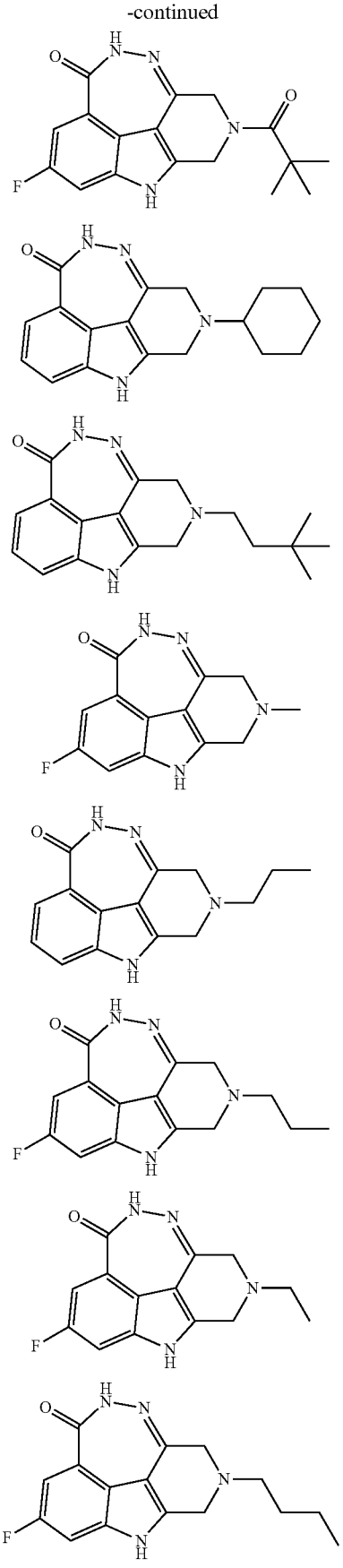

-continued

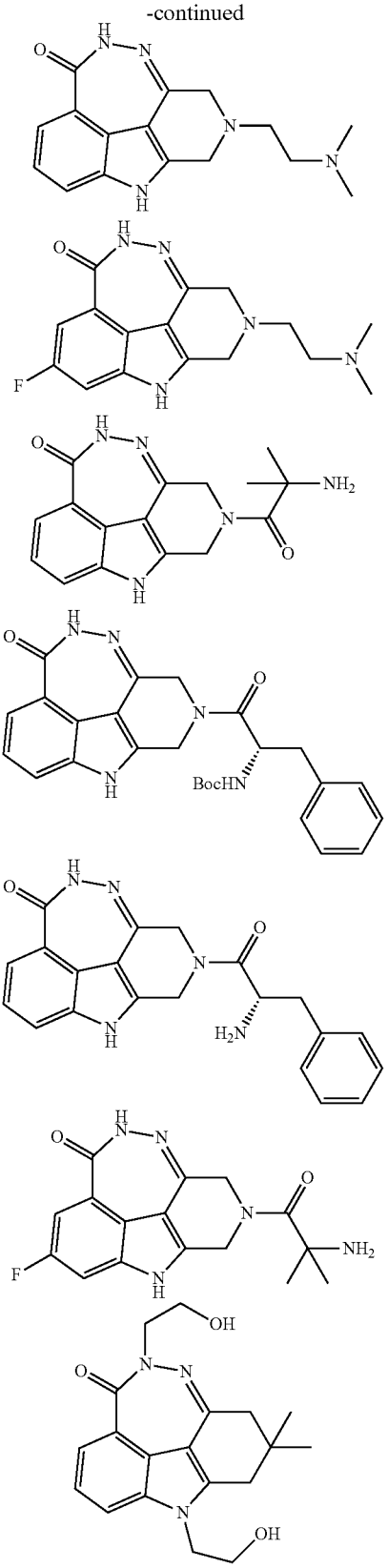

-continued

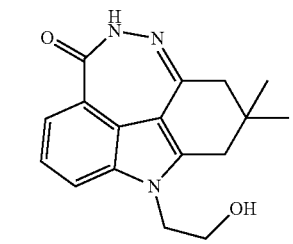

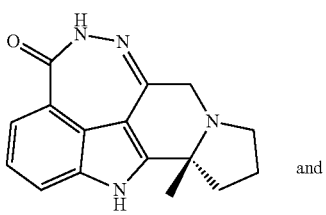

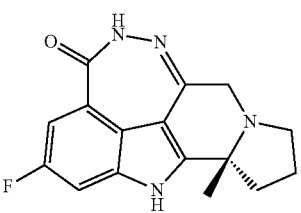

and

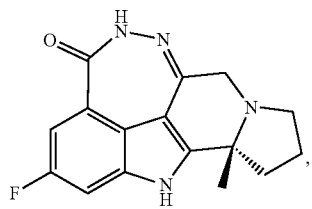 [SMILES: C[C@]12CCCN1CC1=NNC(=O)c3cc(F)cc4[nH]c2c1c34]

or a stereoisomer thereof or a pharmaceutically acceptable salt thereof.

14. The oral dosage form of claim 1, wherein the dosage form is a tablet or a capsule.

15. The oral dosage form of claim 1, wherein the compound is

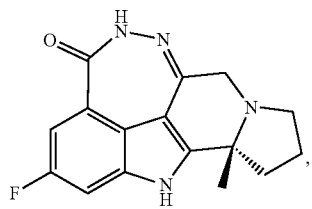 [SMILES: C[C@]12CCCN1CC1=NNC(=O)c3cc(F)cc4[nH]c2c1c34]

or a stereoisomer or a pharmaceutically acceptable salt thereof.

16. The oral dosage form of claim 14, wherein the dosage form comprises about 10 mg to about 500 mg of the compound.

17. The oral dosage form of claim 15, wherein the dosage form comprises about 10 mg to about 500 mg of the compound.

* * * * *

UNITED STATES PATENT AND TRADEMARK OFFICE
CERTIFICATE OF CORRECTION

PATENT NO.         : 10,501,467 B2
APPLICATION NO.    : 16/135512
DATED              : December 10, 2019
INVENTOR(S)        : Changyou Zhou et al.

It is certified that error appears in the above-identified patent and that said Letters Patent is hereby corrected as shown below:

In the Claims

In Claim 1 at Column 112, Line 7, please replace:
"cyclyl, aryl, or heteroaryl is independently optionally"
With:
-- cyclyl, aryl, and heteroaryl is independently optionally --.

In Claim 10 at Column 115, Lines 33-34, please replace:
"alkyl, alkenyl, alkynyl, cycloalkyl, aryl, heterocyclyl, or heteroaryl is independently optionally sub-"
With:
-- alkyl, alkenyl, alkynyl, cycloalkyl, aryl, heterocyclyl, and heteroaryl is independently optionally sub- --.

In Claim 13 at Column 118, Lines 26-33, please replace:

" 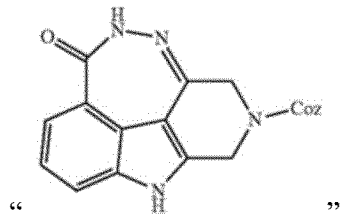 "

With:

-- 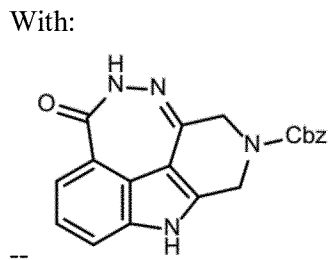 --.

Signed and Sealed this
Fifth Day of May, 2020

Andrei Iancu
*Director of the United States Patent and Trademark Office*

CERTIFICATE OF CORRECTION (continued)
U.S. Pat. No. 10,501,467 B2

In Claim 13 at Column 118, Lines 34-41, please replace:

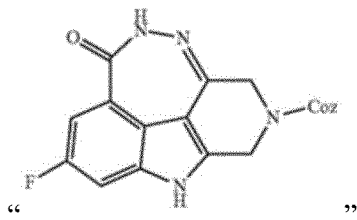

" "

With:

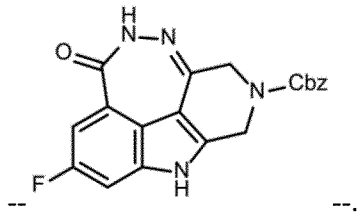

-- --.

In Claim 15 at Column 124, Lines 40-41, please replace:
"The oral dosage form of claim 1, wherein the compound is"
With:
-- The oral dosage form of claim 14, wherein the compound is --.